United States Patent
Munzert et al.

(10) Patent No.: US 8,058,270 B2
(45) Date of Patent: Nov. 15, 2011

(54) DIHYDROPTERIDINONES FOR THE TREATMENT OF CANCER DISEASES

(75) Inventors: Gerd Munzert, Ulm (DE); Martin Steegmaier, Reutlingen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 393 days.

(21) Appl. No.: 12/120,740

(22) Filed: May 15, 2008

(65) Prior Publication Data

US 2008/0221099 A1 Sep. 11, 2008

Related U.S. Application Data

(63) Continuation of application No. 11/188,926, filed on Jul. 25, 2005, now abandoned.

(30) Foreign Application Priority Data

Aug. 14, 2004 (EP) .................................... 04019359

(51) Int. Cl.
- A61K 31/54 (2006.01)
- A61K 31/535 (2006.01)
- A01N 43/58 (2006.01)
- C07D 417/00 (2006.01)

(52) U.S. Cl. .................. 514/228.5; 514/234.2; 514/249; 514/250; 544/61; 544/118; 544/231; 544/251; 544/238

(58) Field of Classification Search ............... 514/228.5, 514/234.2, 249, 250; 544/61, 118, 231, 251, 544/238

See application file for complete search history.

(56) References Cited

U.S. PATENT DOCUMENTS

| | | | |
|---|---|---|---|
| 4,957,922 A | 9/1990 | Lammens et al. |
| 5,167,949 A | 12/1992 | Ferrand et al. |
| 5,198,547 A | 3/1993 | Bailey et al. |
| 5,424,311 A | 6/1995 | Billhardt-Troughton et al. |
| 5,698,556 A | 12/1997 | Chan |
| 6,096,924 A | 8/2000 | Studer et al. |
| 6,156,766 A | 12/2000 | Arita et al. |
| 6,174,895 B1 | 1/2001 | Kleinman |
| 6,605,255 B2 | 8/2003 | Kroll et al. |
| 6,806,272 B2 | 10/2004 | Bauer et al. |
| 6,861,422 B2 | 3/2005 | Hoffmann et al. |
| 6,875,868 B2 | 4/2005 | Bonnert et al. |
| 7,238,807 B2 | 7/2007 | Duran et al. |
| 7,241,889 B2 | 7/2007 | Hoffmann et al. |
| 7,332,491 B2 | 2/2008 | Grauert et al. |
| 7,371,753 B2 | 5/2008 | Stadtmueller et al. |
| 7,414,053 B2 | 8/2008 | Grauert et al. |
| 7,439,358 B2 | 10/2008 | Linz et al. |
| 7,547,780 B2 | 6/2009 | Grauert et al. |
| 7,625,899 B2 | 12/2009 | Hoffmann et al. |
| 7,626,019 B2 | 12/2009 | Duran et al. |
| 7,629,460 B2 | 12/2009 | Grauert et al. |
| 7,700,769 B2 | 4/2010 | Grauert et al. |
| 7,723,517 B2 | 5/2010 | Grauert et al. |
| 7,728,134 B2 | 6/2010 | Linz et al. |
| 7,750,152 B2 | 7/2010 | Hoffman et al. |
| 7,759,347 B2 | 7/2010 | Hoffmann |
| 7,759,485 B2 | 7/2010 | Linz et al. |
| 7,807,831 B2 | 10/2010 | Grauert et al. |
| 7,816,530 B2 | 10/2010 | Grauert |

(Continued)

FOREIGN PATENT DOCUMENTS

| | | |
|---|---|---|
| CA | 2458699 A1 | 3/2003 |
| CA | 2517020 A1 | 9/2004 |
| CA | 2517010 A1 | 11/2004 |
| CA | 2576290 A1 | 2/2006 |
| EP | 143478 A1 | 6/1985 |

(Continued)

OTHER PUBLICATIONS

Eschenbach, J. Nat. Cancer Inst., vol. 94, No. 11,790-792, Jun. 5, 2002.*

Ohio Department of Health; Brain & Other Central Nervous System Cancer in Ohio, 1997-2001; Sep. 2004; pp. 1-4.

Voskoglou-Nomikos et al; Clincial Predictive Value of the in Vitro Cell Line, Human Xenograft, and Mouse Allograft Preclinical Cancer Models; Clinical Cancer Research; Sep. 15, 2003; vol. 9; pp. 4227-4239.

(Continued)

*Primary Examiner* — Brandon Fetterolf
*Assistant Examiner* — Shirley V Gembeh
(74) *Attorney, Agent, or Firm* — Michael P. Morris; Anthony P. Bottino

(57) ABSTRACT

Disclosed is the use of a compound of general Formula (1),

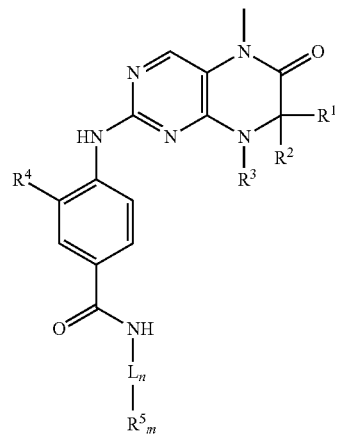

optionally in form of its tautomers, racemates, enantiomers, diastereomers and the mixtures thereof and optionally in form of the pharmacologically acceptable acid addition salts, solvates, hydrates, polymorphs, physiologically functional derivatives or prodrugs thereof, for the preparation of a pharmaceutical composition for the treatment of diseases characterized by abnormal cell proliferation in a human or non-human mammalian body by inhibition of polo like kinases as mitotic regulators.

5 Claims, No Drawings

U.S. PATENT DOCUMENTS

| | | |
|---|---|---|
| 2002/0183292 A1 | 12/2002 | Pairet et al. |
| 2002/0183293 A1 | 12/2002 | Banerjee et al. |
| 2003/0130286 A1 | 7/2003 | Denny et al. |
| 2004/0029885 A1 | 2/2004 | Bauer et al. |
| 2004/0147524 A1 | 7/2004 | Bauer et al. |
| 2004/0176380 A1 | 9/2004 | Hoffmann et al. |
| 2005/0014760 A1 | 1/2005 | Hoffmann et al. |
| 2005/0014761 A1 | 1/2005 | Hoffmann et al. |
| 2005/0148501 A1 | 7/2005 | Palmer et al. |
| 2005/0159414 A1 | 7/2005 | Nickolaus et al. |
| 2005/0165010 A1 | 7/2005 | Nickolaus et al. |
| 2006/0004014 A1 | 1/2006 | Hoffmann et al. |
| 2006/0009457 A1 | 1/2006 | Hoffmann et al. |
| 2006/0025411 A1 | 2/2006 | Hoffmann et al. |
| 2006/0035902 A1 | 2/2006 | Linz et al. |
| 2006/0035903 A1 | 2/2006 | Mohr et al. |
| 2006/0046989 A1 | 3/2006 | Grauert et al. |
| 2006/0047118 A1 | 3/2006 | Stadtmueller et al. |
| 2006/0052383 A1 | 3/2006 | Grauert et al. |
| 2006/0058311 A1 | 3/2006 | Munzert et al. |
| 2006/0074088 A1 | 4/2006 | Munzert et al. |
| 2006/0079503 A1 | 4/2006 | Schwede et al. |
| 2007/0208027 A1 | 9/2007 | Duran et al. |
| 2007/0213528 A1 | 9/2007 | Duran et al. |
| 2007/0213529 A1 | 9/2007 | Duran et al. |
| 2007/0213530 A1 | 9/2007 | Duran et al. |
| 2007/0213531 A1 | 9/2007 | Duran et al. |
| 2007/0213534 A1 | 9/2007 | Duran et al. |
| 2007/0219369 A1 | 9/2007 | Duran et al. |
| 2008/0108812 A1 | 5/2008 | Grauert et al. |
| 2008/0113992 A1 | 5/2008 | Grauert et al. |
| 2008/0171747 A1 | 7/2008 | Hoffman et al. |
| 2008/0177066 A1 | 7/2008 | Linz et al. |
| 2008/0194818 A1 | 8/2008 | Grauert et al. |
| 2008/0221099 A1 | 9/2008 | Munzert et al. |
| 2008/0293944 A1 | 11/2008 | Hoffmann et al. |
| 2008/0319190 A1 | 12/2008 | Grauert et al. |
| 2008/0319192 A1 | 12/2008 | Grauert et al. |
| 2008/0319193 A1 | 12/2008 | Grauert et al. |
| 2009/0018333 A1 | 1/2009 | Grauert et al. |
| 2009/0023733 A1 | 1/2009 | Cage et al. |
| 2009/0030004 A1 | 1/2009 | Linz et al. |
| 2009/0124628 A1 | 5/2009 | Hoffmann et al. |
| 2009/0143379 A1 | 6/2009 | Mohr et al. |
| 2009/0238828 A1 | 9/2009 | Munzert et al. |
| 2009/0280115 A1 | 11/2009 | Maier et al. |
| 2009/0298840 A1 | 12/2009 | Linz et al. |
| 2010/0029642 A1 | 2/2010 | Hoffmann et al. |
| 2010/0249412 A1 | 9/2010 | Linz et al. |
| 2010/0249458 A1 | 9/2010 | Linz et al. |
| 2010/0280037 A1 | 11/2010 | Linz et al. |
| 2010/0324288 A1 | 12/2010 | Hoffmann et al. |

FOREIGN PATENT DOCUMENTS

| | | |
|---|---|---|
| EP | 347146 A2 | 12/1989 |
| EP | 399856 A1 | 11/1990 |
| EP | 429149 A1 | 5/1991 |
| ES | 2287583 | 12/2007 |
| RU | 2002125451 A | 1/2004 |
| WO | 9609045 A1 | 3/1996 |
| WO | 9634867 A1 | 11/1996 |
| WO | 9636597 A1 | 11/1996 |
| WO | 9811893 A1 | 3/1998 |
| WO | 01/19825 A1 | 3/2001 |
| WO | 0170741 A1 | 9/2001 |
| WO | 0178732 A1 | 10/2001 |
| WO | 02057261 A2 | 7/2002 |
| WO | 02076954 A1 | 10/2002 |
| WO | 02076985 A1 | 10/2002 |
| WO | 03020722 A1 | 3/2003 |
| WO | 03093249 A1 | 11/2003 |
| WO | 2004014899 A1 | 2/2004 |
| WO | 2004076454 A1 | 9/2004 |
| WO | 2004093848 A2 | 11/2004 |
| WO | 2005067935 A1 | 7/2005 |
| WO | 2006/018182 A1 | 2/2006 |
| WO | 2006/018221 A1 | 2/2006 |
| WO | 2006018185 A2 | 2/2006 |
| WO | 2006018220 A2 | 2/2006 |
| WO | 2006018221 A1 | 2/2006 |
| WO | 2006021378 A1 | 3/2006 |
| WO | 2007090844 A1 | 8/2007 |
| WO | 2009019205 A1 | 2/2009 |

OTHER PUBLICATIONS

Cecil Textbook of Medicine; 20th Edition; vol. 1; W.B. Saunders Co. 1997; pp. 1004-1009.

Journal of the National Cancer Institute; Jun. 5, 2002; vol. 94; No. 11; pp. 790-792.

ACPS Meeting, Background Information. "Scientific considerations of plymorphism in pharmaceutical solids: abbreviated new drug applications". Oct. 2002.

Ahlenius, T. List of cardiovascular disorder/diseases. Ahlenius, Karolinska Institutet. Stockholm, Sweden. Cardiovascular Diseases, p. 1-34, Apr. 2007.

Ahmad, N. "Polo-like kinase (Plk) 1: a novel target for the treatment of prostate cancer". Dept of Dermatology, Univ. Wisconsin, pp. 3-5.

BBC News/Health, Killer Breast Cancern Therapy Hope, www.newsvote.bbc/co./uk, downloaded Mar. 26, 2009.

Blain, S. W. et al., "Differential interaction of the cyclin-dependent kinase (Cdk) Inhibitor p27KIP with cyclin A-Cdk2 and cyclin D2-Cdk4". The Journal of Biological Chemistry, vol. 272, No. 41, Issue Oct. 10, 1997, pp. 25862-25872.

Dipolar aprotic solvent. Exhibit A, IUPAC Compendium of Chemical Terminology, 2nd Edition, 1997.

Doerwald, F.Z. "Side reactions in organice synthesis". 2005.

Eurasian Opinion, Appln No. 2007/00389/28, Maly Slatoustinsky per., d.10, kv.15, 101000 Moscow, Russia, "EVROMARKPAT", 2007.

Ferrand, G., et al., "Synthesis and potential antiallergic activity of new pteridinones and related compounds". Eur. J. Med. Chem, 31, 1996, pp. 273-280. XP-2246920.

Ghandi, L., et al., "An Open-Label Phase II Trial of the PLK Inhibitor BI 2536 in Patients with Sensitive Relapse Small Cell Lung Cancer". ASCO Meeting 2009.

Giron, G. "Thernal analysis and calorimetric methods in the characterization of plymorphs and solvates". Thermochimica Acta 248, 1995, pp. 1-59.

Goodman-Gilman's "The Pharmacological Basis of Therapeutics". Ninth edition, 1996, pp. 1225-1271.

Ito, Y., et al., "Polo-like kinase 1 (PLK) expression is associated with cell proliferative activity and cdc2 expression in malignant-lymphoma of the thyroid". Anticancer Research, 2004, vol. 24, No. 1, pp. 259-263.

Jaworska, J., et al., "Review of methods for assessing the applicability domains of SARS and QSARA". Sponsor: The European Commission—Joint Research Ctr., Institute for Health and Consumer Protection—ECVAM, Italy, 2004.

Kashima, M. K. et al., "Expression of polo-like kinase (PLK1) in non-Hodgkin's lymphomas". NCBI, PubMed, 2005.

Kimball, S. D. et al., "Cell cycle kinases and checkpoint regulation in cancer". Annual Reports in Medicinal Chemistry, 36, Chapter 14, pp. 139-148.

Leukemia & Lymphoma Society—Disease Information—Lymphoma. www.leukemia-lymphoma.org/all_page?item_id-7030, downloaded Mar. 26, 2009.

Leukemia & Lymphoma Society—Disease Information. www.leukemia-lymphoma.org/all_page?item_id-7026, downloaded Mar. 26, 2009.

Marko, D. et al., "Intracellular localization of 7-benzylamino-6-chloro-2-piperazino-4-pyrrolidino-pteridine in membrane structures impeding the inhibition of cytosolic cyclic AMP-specific phosphodiesterase". Biochemical Pharmacology, 63, 2002, pp. 669-676.

Masuda, Y. et al., "B-Hydroxyisovalerylshikonin induces apoptosis in human leukemia cells by inhibiting the activity of a polo-like kinase 1 (PLK)". 2003, Oncogene, 22, pp. 1012-1023.

MedlinePlus: Bacterial Infections. www.nim.nih.gov/medlineplus/print/bacterialinfections.htm, downloaded Mar. 26, 2009.

MedlinePlus: Viral Infections. www.nim.nih.gov/medlineplus/print/viralinfections.htm, downloaded Mar. 26, 2009.

Merck Manual of Medical Information—Home Edition, Section 17. "Parasitic Infections". Chapter 184, 2003.

Mito, K., et al., "Expression of polo-like kinase (PLK1) in non-Hodgkin's lymphomas". NCBI, PubMed, 2005, Leuk. Lymphoma, 46(2), pp. 251-231.

Nagao, K. et al., "Effect of MX-68 on airway inflammation and hyperresponsiveness in mice and guinea-pigs". Journal of Pharmacy and Pharmacology, JPP 2004, 56, pp. 187-196.

National Institute of Neurological Disorders, Index Stroke, 2006.

National Kidney Foundation: Chronic Kidney Disease (CKD). www.kidney.org/kidneydisease/ckd/index.cfm, downloaded Mar. 26, 2009.

Norman, P. "PDE4 inhibitors". 1999, Ashley Publications Ltd., pp. 1101-1118.

Office Action mailed Dec. 10, 2003 for U.S. Appl. No. 10/226,710, filed Aug. 23, 2002.

Office Action mailed Apr. 28, 2004 for U.S. Appl. No. 10/374,876, filed Feb. 26, 2003.

Organic Chemistry, Grupo Editorial Iberoamerica, Section 13, 3, pp. 301-302, 1983.

Rylander, P.N. "Hydrgenation Methods". 1985, Chapter 13.

Rylander, P.N. "Hydrgenation Methods". 1985, Chapters 3, 4.

Rylander, P.N. "Hydrgenation Methods". 1985, Chapters 8, 9, 10, 11.

Rylander, P.N. "Hydrgenation Methods". 1985, Chapter 5, 6, 7.

Rylander, P.N., "Hydrogenation Methods". 1985, Chapters 1, 2.

Santing, R. E. et al., "Brochodilatory and anti-inflammatory properties of inhaled selective phosphodiesterase inhibitors in a guinea pig model of allergic asthma". European Journal of Pharmacology, 429, 2001, pp. 335-344.

Savelli, F. et al., "Heterotricyclic system Part II—synthesis of new pyrido[1'2':4,5]pyrazino[3,2-d] pyrimidines". Bollettino Chimico Farmaceutico, 131(8), Sep. 1992, pp. 309-312.

Snyder, J. S. et al., "Common bacteria whose susceptibility to antimicrobials is no longer predictable". NCBI, PubMed, 2000, J. Med. Liban, 48, pp. 208-214.

Souillac, P. et al., "Characterization of delivery systems, differential scanning calorimetry". pp. 212-227.

Sugar, A. M. et al., "Comparison of three methods of antifungal susceptibility testing with the proposed NCCLS standard broth macrodilution assay: lack of effect of phenol red". Mycology, Diagn Microbiol. Infect. Dis. 1995, 21—pp. 129-133.

Takai, N. et al., "Polo-like kinases (PLKs) and cancer". Oncogene, 2005, 24, pp. 287-291.

Tenbrink, R. E. et al., "Antagonist, partial agonist, and full agonist imidazo[1,5-a]quinoxaline amides and carbamates acting through the BABA/Benzodiazepine receptor". J. Med. Chem. 1994, 37, pp. 758-768.

Turner, W.W.et al., "Recent advances in the medicinal chemistry of antifungal agents". Current Pharmacutical Design, 1996, 2, pp. 209-224.

Verschuren, E.W. et al., "The cell cycle and how it is steered by Kaposi's sarcoma-associated herpesvirus cyclin". Journal of General Virology, 2004, 85, pp. 1347-1361.

Vippagunta, S. R. et al., "Crystalline solids". Advanced Drug Delivery Reviews, 48, 2001, pp. 3-26.

Viral Defense Foundation. www.viraldefense.org/mission.htm, downloaded Mar. 26, 2009.

Visiting Nurse Association of America. www.vnaa.org/gen/Germ_Protection_Center_Cold_and_Flu_Resources,html, downloaded Mar. 26, 2009.

Wagner, B. et al, "7-Benzylamino-6-chloro-2-piperazino-4-pyrrolidino-pteridine, a potent inhibitor of cAMP-specific phosphodiesterase, enhancing nuclear protein binding to the CRE consensus sequence in human tumour cells", Biochemical Pharmacology, Pergamon, Oxford, GB, pp. 659-668.

Wagner, G. et al., "Synthesis of new phrido[3',2':4,5] thieno '3,2-d] 1,2,3-triazine derivatives as antianaphylactics". Biosciences Dept of the University of Leipzig, Pharmazie (Pharmacy), 48, 19923, vol. 7, pp. 514-518.

Webster's Comprehensive Dictionary, 1996, pp. 1013-1014.

Wolf, D. E.et al., "The structure of rhizopterin". Contribution from the Research Labs of Merck and Co. Inc. Nov. 1947, Journal of American Chem. Soc., vol. 69, pp. 2753-2759. XP002352205.

Chen, J.X. et al., "Parallel differentiated recognition of ketones and acetals". Angewandte Chemie Int. Ed, vol. 37, Issue 1/2, p. 91-93, 1998.

Dyson, G, et al. "The Chemistry of Synthetic Drugs". 1964, p. 12-19.

International Search Report for PCT/EP2005/056291 mailed Mar. 21, 2006.

Jamieson, C. et al., "Application of ReactArray Robotics and Design of Experiments Techniques in Optimisation of Supported Reagent Chemistry". Org. Proc. Res. & Dev., 2002, 6, p. 823-825.

Mashkovkii, M.D., "Medicaments". Moscow, Novaja Volna, 2001, vol. 1, p. 11.

Mashkovskii, M.D. "Drugs", Handbook for Doctors, 1993, Part I, Ch.1, p. 8.

Mayer, SF, et al., "Enzyme-initiated domino (cascase) reactions". Chem. Soc. Rev, 2001, p. 332-339.

McInnes, C. "Inhibitors of polo-like kinase reveal roles in spindle-pole maintenance". Nature Chemical Biology, vol. 2, No. 11, Nov. 2006, p. 608.

Mikhailov, I.B., Principles of Rational Pharmacotherapy. Handbook for clinical pharmacology for students of pediatric and medical faculties of medical high schools, St. Petersburg, Russia, "Foliant", 1999, p. 25.

Neidle, S. ed., "Cancer Drug Design and Discovery", Elsevier/Academic Press, 2008, p. 427-431.

Rocha Lima, C.M. et al. "Randomized phase II trial of gemcitabine plus irinotecan or docetaxel uin stage IIIb or stage IV NSCLC" Annals of Oncology, 15(3), p. 410-418, 2004.

Science, vol. 310, Oct. 21, 2005, p. 409, Chemistry: One After Another.

Steegmaier, M. et al. "BI 2536, a potent and selective inhibitor of polo-like kinase 1, inhibits tumor growth in vivo". Current Biology, 2007, 17(4), p. 316-322.

Stephenson, D.T. et al. "The effects of a selective dopamine D2 receptor agonist on behavioral and pathological outcome in 1-methl-4-phenyl-1,2,3,6-tetrahydropyridine-treated squirrel monkeys". J. Pharmacology and Experimental Therapeutics, vol. 303, No. 2, 2002, p. 1257.

Turner, S., "The Design of Organic Syntheses". Elsevier, 1976, pp. 10 and 149.

Walsh, F. "No "Magic Bullet" Cure for Cancer". BBC News Feb. 1, 2007, http://news.bbc,co.uk/2/health/6310697.stm, downloaded Jul. 6, 2010.

* cited by examiner

DIHYDROPTERIDINONES FOR THE TREATMENT OF CANCER DISEASES

APPLICATION DATA

This application claims benefit of U.S. application Ser. No. 11/188,926 file Jul. 25, 2005 which claims benefit to European Patent application no. EP 04 019 359.1 filed Aug. 14, 2004.

FIELD OF INVENTION

The present invention relates to dihydropteridinones of general Formula (I),

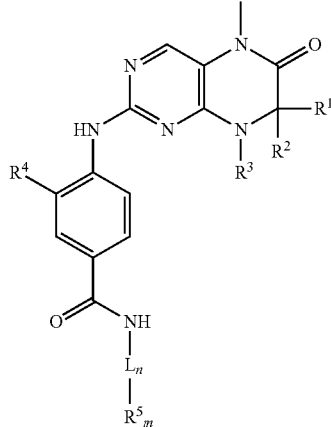

(I)

wherein the groups L, $R^1$, $R^2$, $R^3$, $R^4$ and $R^5$ have the meanings given in the claims and specification, optionally in form of its tautomers, racemates, enantiomers, diastereomers and the mixtures thereof and optionally in form of the pharmacologically acceptable acid addition salts, solvates, hydrates, polymorphs, physiologically functional derivatives or prodrugs thereof, and their use in cancer therapy.

BACKGROUND OF THE INVENTION

Polo-like kinases (PLKs) are serine/threonine kinases that play important roles in regulating processes in the cell cycle. There are four PLKs disclosed in the state of the art, i.e. PLK-1, PLK-2, PLK-3. and PLK-4. PLKs play a role in the regulation of the eukaryotic cell cycle (e.g. regulation of the mitotic machinery in mammalian cells). Especially for PLK-1 a central role with respect to the regulation of mitosis is shown (Glover et al. 1998, *Genes Dev.* 12:3777-87; Qian et al. 2001, *Mol Biol Cell.* 12:1791-9). Overexpression of PLK-1 seems to be strongly associated with neoplastic cells including cancers (WO 2004/014899). Overexpression of PLK1 has been documented for various tumor types such as non-small cell lung cancer, squamous cell carcinomas, breast, ovary or papillary carcinomas as well as colorectal cancers (Wolf et al. 1997, *Oncogene* 14, pages 543-549; Knecht et al. 1999, *Cancer Res.* 59, pages 2794-2797; Wolf et al. 2000, *Pathol Res Pract.* 196, pages 753-759; Weichert et al. 2004, *Br. J. Cancer* 90, pages 815-821; Ito et al. 2004, *Br. J. Cancer* 90, pages 414-418; Takahashi et al. 2003, *Cancer Sci.* 94, pages 148-152).

It is the purpose of the present invention to provide compounds for the treatment of various cancer diseases.

DETAILED DESCRIPTION OF THE INVENTION

The invention relates to the use of compounds of Formula (I),

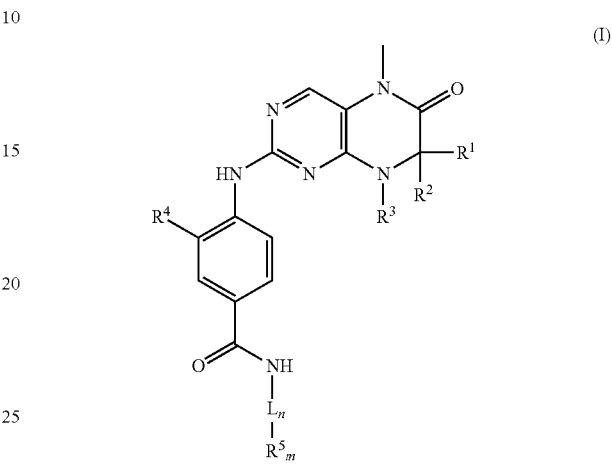

(I)

wherein $R^1$, $R^2$ which may be identical or different, denote hydrogen or optionally substituted $C_1$-$C_6$-alkyl, or $R^1$ and $R^2$ together denote a 2- to 5-membered alkyl bridge which may contain 1 to 2 heteroatoms, $R^3$ denotes hydrogen or a group selected from among optionally substituted $C_1$-$C_{12}$-alkyl, $C_2$-$C_{12}$-alkenyl, $C_2$-$C_{12}$-alkynyl and $C_6$-$C_{14}$-aryl, or a group selected from among optionally substituted and/or bridged $C_3$-$C_{12}$-cycloalkyl, $C_3$-$C_{12}$-cycloalkenyl, $C_7$-$C_{12}$-polycycloalkyl, $C_7$-$C_{12}$-polycycloalkenyl, $C_5$-$C_{12}$-spirocycloalkyl, $C_3$-$C_{12}$-heterocycloalkyl which contains 1 to 2 heteroatoms, and $C_3$-$C_{12}$-heterocycloalkenyl which contains 1 to 2 heteroatoms, or $R^1$ and $R^3$ or $R^2$ and $R^3$ together denote a saturated or unsaturated $C_3$-$C_4$-alkyl bridge which may contain 1 heteroatom, $R^4$ denotes a group selected from among hydrogen, —CN, hydroxy, —$NR_6R_7$ and halogen, or a group selected from among optionally substituted $C_1$-$C_6$-alkyl, $C_2$-$C_6$-alkenyl, $C_2$-$C_6$-alkynyl, $C_1$-$C_5$-alkyloxy, $C_2$-$C_5$-alkenyloxy, $C_2$-$C_5$-alkynyloxy, $C_1$-$C_6$-alkylthio, $C_1$-$C_6$-alkylsulphoxo and $C_1$-$C_6$-alkylsulphonyl, L denotes a linker-selected from among optionally substituted-$C_2$-$C_{10}$-alkyl, $C_2$-$C_{10}$-alkenyl, $C_6$-$C_{14}$-aryl, —$C_2$-$C_4$-alkyl-$C_6$-$C_{14}$-aryl, —$C_6$-$C_{14}$-aryl-$C_1$-$C_4$-alkyl, optionally bridged $C_3$-$C_{12}$-cycloalkyl and heteroaryl which contains 1 or 2 nitrogen atoms, n denotes 0 or 1 m denotes 1 or 2

$R^5$ denotes a group selected from among optionally substituted morpholinyl, piperidinyl, piperazinyl, piperazinylcarbonyl, pyrrolidinyl, tropenyl, $R^8$-diketomethylpiperazinyl, sulphoxomorpholinyl, sulphonylmorpholinyl, thiomorpholinyl, —NR$^8$R$^9$ and azacycloheptyl, R$^6$, R$^7$ which may be identical or different, denote hydrogen or C$_1$-C$_4$-alkyl, and R$^8$, R$^9$ denote unsubstituted nitrogen substituents at R$^5$, which may be identical or different, denote either hydrogen or a group selected from among C$_1$-C$_6$-alkyl, —C$_1$-C$_4$-alkyl-C$_3$-C$_{10}$-cycloalkyl, C$_3$-C$_{10}$-cycloalkyl, C$_6$-C$_{14}$-aryl, —C$_1$-C$_4$-alkyl-C$_6$-C$_{14}$-aryl, pyranyl, pyridinyl, pyrimidinyl, C$_1$-C$_4$-alkyloxycarbonyl, C$_6$-C$_{14}$-arylcarbonyl, C$_1$-C$_4$-alkylcarbonyl, C$_6$-C$_{14}$-arylmethyloxycarbonyl, C$_6$-C$_{14}$-arylsulphonyl, C$_1$-C$_4$-alkylsulphonyl and C$_6$-C$_{14}$-aryl-C$_1$-C$_4$-alkylsulphonyl, optionally in form of its tautomers, racemates, enantiomers, diastereomers and the mixtures thereof and optionally in form of the pharmacologically acceptable acid addition salts, solvates, hydrates, polymorphs, physiologically functional derivatives or prodrugs thereof, for the preparation of a pharmaceutical composition for the treatment of diseases characterized by abnormal cell proliferation in a human or non-human mammalian body by inhibition of polo like kinases as mitotic regulators.

Preferred is the use according to the invention of compounds of Formula (I) wherein R$^1$ to R$^4$, R$^6$ and R$^7$ are as hereinbefore defined, and L denotes a linker selected from among optionally substituted C$_2$-C$_{10}$-alkyl, C$_2$-C$_{10}$-alkenyl, C$_6$-C$_{14}$-aryl, —C$_2$-C$_4$-alkyl-C$_6$-C$_{14}$-aryl, —C$_6$-C$_{14}$-aryl-C$_1$-C$_4$-alkyl, optionally bridged C$_3$-C$_{12}$-cycloalkyl and heteroaryl which contains 1 or 2 nitrogen atoms n denotes 1 m denotes 1 or 2

R$^5$ denotes a group which is bound to L via a nitrogen atom, selected from among optionally substituted morpholinyl, piperidinyl, R$^8$-piperazinyl, pyrrolidinyl, tropenyl, R$^8$-diketomethylpiperazinyl, sulphoxomorpholinyl, sulphonylmorpholinyl, thiomorpholinyl, —NR$^8$R$^9$ and azacycloheptyl, R$^8$, R$^9$ denote unsubstituted nitrogen substituents at R$^5$, which may be identical or different, hydrogen or a group selected from among C$_1$-C$_6$-alkyl, —C$_1$-C$_4$-alkyl-C$_3$-C$_{10}$-cycloalkyl, C$_3$-C$_{10}$-cycloalkyl, C$_6$-C$_{14}$-aryl, —C$_1$-C$_4$-alkyl-C$_6$-C$_{14}$-aryl, pyranyl, pyridinyl, pyrimidinyl, C$_1$-C$_4$-alkyloxycarbonyl, C$_6$-C$_{14}$-arylcarbonyl, C$_1$-C$_4$-alkylcarbonyl, C$_6$-C$_{14}$-arylmethyloxycarbonyl, C$_6$-C$_{14}$-arylsulphonyl, C$_1$-C$_4$-alkylsulphonyl and C$_6$-C$_{14}$-aryl-C$_1$-C$_4$-alkylsulphonyl, optionally in the form of the tautomers, the racemates, the enantiomers, the diastereomers and the mixtures thereof, and optionally the pharmacologically acceptable acid addition salts thereof.

Also preferred is the use according to the invention of compounds of Formula (I), wherein R$^1$ to R$^4$, R$^6$ and R$^7$ are as hereinbefore defined, L denotes a linker selected from among optionally substituted C$_2$-C$_{10}$-alkyl, C$_2$-C$_{10}$-alkenyl, C$_6$-C$_{14}$-aryl, —C$_2$-C$_4$-alkyl-C$_6$-C$_{14}$-aryl, —C$_6$-C$_{14}$-aryl-C$_1$-C$_4$-alkyl, optionally bridged C$_3$-C$_{12}$-cycloalkyl and heteroaryl which contains 1 or 2 nitrogen atoms n denotes 0 or 1 m denotes 1 or 2

R$^5$ denotes a group which is bound to L via a carbon atom, selected from among R$^8$-piperidinyl, R$^8$R$^9$-piperazinyl, R$^8$-pyrrolidinyl, R$^8$-piperazinylcarbonyl, R$^8$-tropenyl, R$^8$-morpholinyl and R$^8$-azacycloheptyl, and R$^8$, R$^9$ denote unsubstituted nitrogen substituents at R$^5$, which may be identical or different, hydrogen or a group selected from among C$_1$-C$_6$-alkyl, —C$_1$-C$_4$-alkyl-C$_3$-C$_{10}$-cycloalkyl, C$_3$-C$_{10}$-cycloalkyl, C$_6$-C$_{14}$-aryl, —C$_1$-C$_4$-alkyl-C$_6$-C$_{14}$-aryl, pyranyl, pyridinyl, pyrimidinyl, C$_1$-C$_4$-alkyloxycarbonyl, C$_6$-C$_{14}$-arylcarbonyl, C$_1$-C$_4$-alkylcarbonyl, C$_6$-C$_{14}$-arylmethyloxycarbonyl, C$_6$-C$_{14}$-arylsulphonyl, C$_1$-C$_4$-alkylsulphonyl and C$_6$-C$_{14}$-aryl-C$_1$-C$_4$-alkylsulphonyl, optionally in the form of the tautomers, the racemates, the enantiomers, the diastereomers and the mixtures thereof, and optionally the pharmacologically acceptable acid addition salts thereof.

Particularly preferred is the use of compounds of Formula (I) wherein

L, m, n and R$^3$ to R$^9$ are as hereinbefore defined, and

R$^1$, R$^2$ which may be identical or different, denote a group selected from among hydrogen, Me, Et, Pr, or R$^1$ and R$^2$ together form a C$_2$-C$_4$-alkyl bridge, optionally in the form of the tautomers, the racemates, the enantiomers, the diastereomers and the mixtures thereof, and optionally the pharmacologically acceptable acid addition salts thereof.

Especially preferred is the use according to the invention of compounds of Formula (I) wherein R$^1$, R$^2$, m, n and R$^5$ to R$^8$ are as hereinbefore defined, and R$^3$ denotes a group selected from among optionally substituted C$_1$-C$_{10}$-alkyl, C$_3$-C$_7$-cycloalkyl, C$_3$-C$_6$-heterocycloalkyl and C$_6$-C$_{14}$-aryl or R$^1$ and R$^3$ or R$^2$ and R$^3$ together denote a saturated or unsaturated C$_3$-C$_4$-alkyl bridge which may contain 1 to 2 heteroatoms, R$^4$ denotes a group selected from among hydrogen, OMe, OH, Me, Et, Pr, OEt, NHMe, NH$_2$, F, CL, Br, O-propargyl, O-butynyl, CN, SMe, NMe$_2$, CONH$_2$, ethynyl, propynyl, butynyl and allyl, and L denotes a linker selected from among optionally substituted phenyl, phenylmethyl, cyclohexyl and branched C$_1$-C$_6$-alkyl, optionally in the form of the tautomers, the racemates, the enantiomers, the diastereomers and the mixtures thereof, and optionally the pharmacologically acceptable acid addition salts thereof.

In a further embodiment, the present invention relates to the use of a compound of Formula (I) according to the invention, wherein the compound is selected from the group consisting of the compounds of Formula (I) shown in the following Table

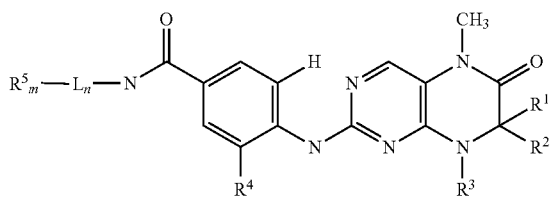
| Ex. | R¹ | R² | Config. R¹ or R² | R³ | R⁴ | $L_n$—$R^5_m$ |
|---|---|---|---|---|---|---|
| 27 | H | X₂—CH₃ | R | X₃ CH(CH₃)₂ | X₄—O—CH₃ | X₅-cyclohexyl-morpholine |
| 44 | H | X₂—CH₃ | R | X₃-cyclopentyl | H | X₅-(1-methylpiperidin-4-yl) |
| 55 | H | X₂—CH₃ | R | X₃-cyclopentyl | CH₃O—X₄ | X₅-CH₂C(CH₃)₂-pyrrolidine |
| 58 | H | X₂—CH₃ | R | X₃-cyclopentyl | CH₃O—X₄ | X₅-C(CH₃)(C₂H₅)CH₂-N(CH₃)₂ |
| 102 | H | X₂—CH₃ | R | X₃-CH(CH₃)₂ | CH₃O—X₄ | X₅-(1-benzylpiperidin-4-yl) |

-continued
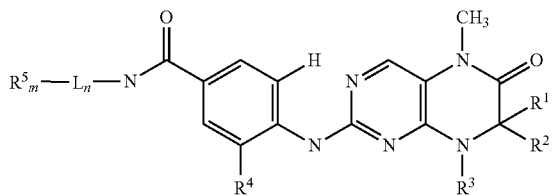
| Ex. | R¹ | R² | Config. R¹ or R² | R³ | R⁴ | Lₙ—R⁵ₘ |
|-----|----|----|------------------|----|----|--------|
| 103 | H | X₂◂CH₃ | R | X₃-cyclopentyl | CH₃O—X₄ | X₅-(4-piperidinyl)-N-benzyl |
| 105 | H | X₂◂CH₃ | R | X₃-cyclopentyl | X₄-O-CH₃ | X₅-cyclohexyl-piperazine-N-CH₂-cyclopropyl |
| 110 | H | X₂–CH₃ | R | X₃-CH(CH₃)₂ | X₄-O-CH₃ | X₅-cyclohexyl-piperazine-N-CH₂-cyclopropyl |
| 115 | H | X₂◂CH₃ | R | X₃-cyclohexyl | CH₃-O-X₄ | X₅-(4-piperidinyl)-N-benzyl |

-continued
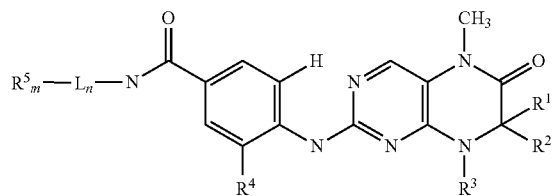
| Ex. | $R^1$ | $R^2$ | Config. $R^1$ or $R^2$ | $R^3$ | $R^4$ | $L_n$—$R^5_m$ |
|---|---|---|---|---|---|---|
| 133 | H | $X_2$—CH$_3$ | R | $X_3$-cyclopentyl | $X_4$-O-CH$_3$ | 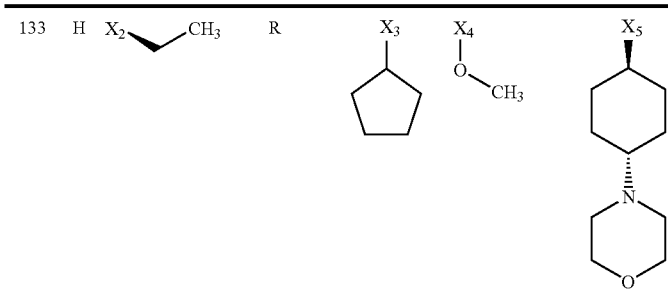 |
| 134 | H | $X_2$—CH$_3$ | R | $X_3$-cyclopentyl | $X_4$-O-CH$_3$ | 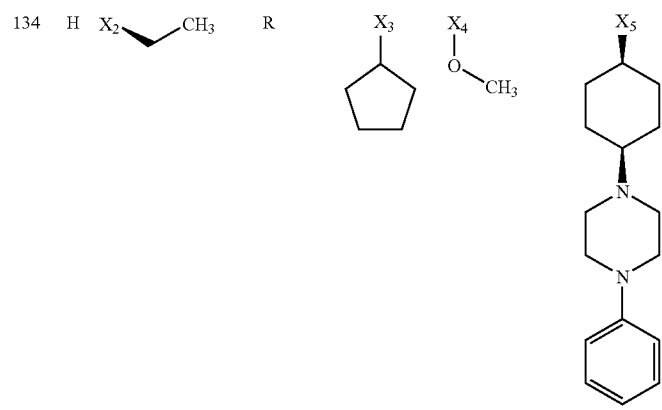 |
| 234 | H | $X_1$—CH$_3$ | R | $X_3$-CH(CH$_3$)$_2$ | $X_4$-O-CH$_3$ | 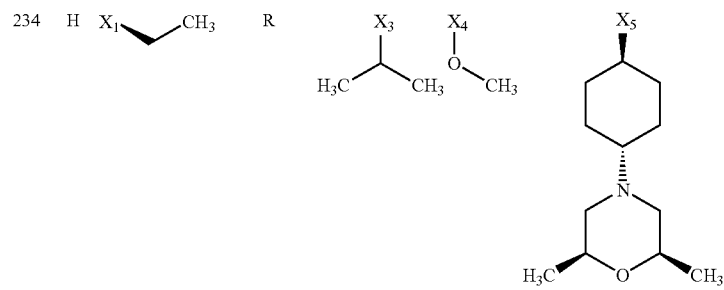 |
| 240 | H | $X_1$—CH$_3$ | R | $X_3$-cyclohexyl | CH$_3$-O-$X_4$ | 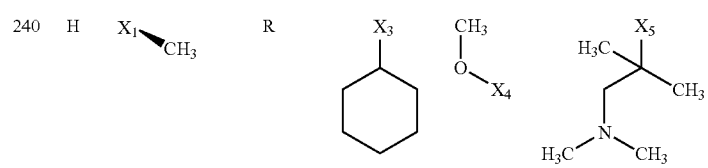 | wherein the abbreviations $X_1$, $X_2$, $X_3$, $X_4$ and $X_5$ used in the Table in each case denote a link to a position in the general Formula shown in the Table instead of the corresponding groups $R^1$, $R^2$, $R^3$, $R^4$ and L-$R^5$.

In a preferred embodiment the invention relates to the use of a compound of Formula (I) according to the invention, wherein the polo-like kinase is PLK-1.

In another preferred embodiment the invention relates to the use of a compound of Formula (I) according to the invention, wherein the disease is characterized by inappropriate cellular proliferation, migration, apoptosis or angiogenesis, preferably by inappropriate cellular proliferation. Inappropriate cell proliferation means cellular proliferation resulting from inappropriate cell growth, from excessive cell division, from cell division at an accelerated rate and/or from inappropriate cell survival.

In another preferred embodiment the invention relates to the use of a compound of Formula (I) according to the invention, wherein the disease is cancer selected from the group consisting of carcinomas, sarcomas, melanomas, myelomas, hematological neoplasias, lymphomas and childhood cancers.

Examples of carcinomas within the scope of the invention include but are not limited to adenocarcinoma (AC), squamous cell carcinoma (SCC) and mixed or undifferentiated carcinomas. Carcinomas within the scope of the invention include but are not limited to the following histologies:
  Head and neck tumours: SCC, AC, transitional cell cancers, mucoepidermoid cancers, undifferentiated carcinomas;
  Central nervous system tumours: Astrocytoma, glioblastoma, meningeoma, neurinoma, schwannoma, ependymoma, hypophysoma, oligodendroglioma, medulloblastoma;
  Bronchial and mediastinal tumours:
    Bronchial tumours:
      Small cell lung cancers (SCLC): oat-cell lung cancer, intermediate cell cancer, combined oat-cell lung cancer;
      Non-small cell lung cancers (NSCLC): SCC, spindle cell carcinoma, AC, bronchioalveolar carcinoma, large cell NSCLC, clear cell NSCLC;
    Mesothelioma;
    Thymoma;
    Thyroid carcinomas: papillary, follicular, anaplastic, medullary;
  Tumours of the gastrointestinal tract:
    Oesophageal cancers: SCC, AC, anaplastic, carcinoid, sarcoma;
    Gastric cancers: AC, adenosquamous, anaplastic;
    Colorectal cancers: AC, including hereditary forms of AC, carcinoid, sarcoma;
    Anal cancers: SCC, transitional epithelial cancer, AC, basal cell carcinoma;
    Pancreatic cancers: AC, including ductal and acinary cancers, papillary, adenosquamous, undifferentiated, tumours of the endocrine pancreas;
    Hepatocellular carcinoma, cholangiocarcinoma, angiosarcoma, hepatoblastoma;
    Biliary carcinomas: AC, SCC, small cell, undifferentiated;
    Gastrointestinal stroma tumours (GIST);
  Gynaecological cancers:
    Breast cancers: AC, including invasive ductal, lobular and medullary cancers, tubular, mucinous cancers, Paget-carcinoma, inflammatory carcinoma, ductal and lobular carcinoma in situ;
    Ovarian cancers: Epithelial tumours, stroma tumours, germ cell tumours, undifferentiated tumours;
    Cervical cancers: SCC, AC, mixed and undifferentiated tumours;
    Endometrial cancers: AC, SCC, mixed, undifferentiated tumours;
    Vulvar cancers: SCC, AC;
    Vaginal cancers: SCC, AC;
  Urinary tract and testicular cancers:
    Testicular cancers: seminoma;
    Non-seminomatous germ cell tumours: teratoma, embryonal cell carcinoma, choriocarcinoma, yolk sac tumour, mixed, Sertoli and Leydig-cell tumours;
    Extragonadal germ cell tumours;
    Prostate cancers: AC, small cell, SCC;
    Renal cell cancers: AC, including clear cell, papillary and chromophobous carcinomas, hereditary forms (e.g. von-Hippel-Lindau syndrome), nephroblastoma;
    Urinary bladder cancers: transitional cell (urothelial) cancers, SCC, AC;
    Urethral cancers: SCC, transitional cell cancers, AC;
    Penile cancers: SCC;
  Tumours of endocrine tissue:
    Thyroid cancers: papillary, follicular, anaplastic, medullary carcinomas, including MEN syndrome;
    Tumours of the endocrine pancreas;
    Carcinoids;
    Pheochromocytoma.

Examples of sarcomas within the scope of the invention include but are not limited to Ewing-sarcoma, osteosarcoma or osteogenic sarcoma, chondrosarcoma, synovial sarcoma, leiomyosarcoma, rhabdomyosarcoma, mesothelial sarcoma or mesothelioma, fibrosarcoma, angiosarcoma or hemangioendothelioma, liposarcoma, glioma or astrocytoma, myxosarcoma, malignant fibrous histiocytoma, mesenchymous or mixed mesodermal tumour, neuroblastoma and clear cell sarcoma.

Examples of melanomas within the scope of the invention include but are not limited to superficial spreading melanoma, nodular and lentigo-maligna melanoma.

Examples of myelomas within the scope of the invention include but are not limited to immunocytoma, plasmocytoma and multiple myeloma.

In another preferred embodiment the invention relates to the use according to the invention, wherein the hematological neoplasia is leukemia.

Further examples of hematologic neoplasias within the scope of the invention include but are not limited to acute or chronic leukemias of myeloid, erythroid or lymphatic origin, myelodysplastic syndromes (MDS) and myeloproliferative syndromes (MPS, such as chronic myelogeneous leukemia, osteomyelofibrosis, polycythemia vera or essential thrombocythemia).

Examples of lymphomas within the scope of the invention include but are not limited to:
  Hodgkin-lymphoma;
  Non-Hodgkin-lymphomas: T- and B-cell lymphomas
    B-cell lymphomas:
      Low and intermediate grade: Chronic lymphocytic leukemia (CLL), prolymphocytic leukemia (PLL), small lymphocytic lymphoma, hairy cell leukemia, plasmacytoid lymphoma, mantle cell lymphoma, follicular lymphoma, marginal zone lymphoma including MALT-lymphoma;

High grade: diffuse large B-cell lymphoma (DLBCL including immunoblastic and centroblastic variants), lymphoblastic, Burkitt's lymphoma;

T-cell lymphomas:
Low grade: T-CLL, T-PLL, Mycosis fungoides, Sezary-syndrome;
High grade: Anaplastic large cell, T-immunoblastic and lymphoblastic.

In another preferred embodiment the invention relates to the use according to the invention, wherein the disease is cancer selected from the group consisting of mixed tumours, undifferentiated tumours and metastases thereof.

Examples of mixed tumours within the scope of the invention include but are not limited to adenosquamous carcinomas, mixed mesodermal tumours, carcinosarcomas and teratocarcinomas.

Examples of undifferentiated, other tumours or metastases thereof within the scope of the invention include but are not limited to undifferentiated tumours, carcinomas of unknown primary (CUP), metastases of unknown primary (MUP) and pheochromocytoma, carcinoids.

In a further embodiment the invention relates to the use of a compound of Formula (I) according to the invention, optionally in form of its tautomers, racemates, enantiomers, diastereomers and the mixtures thereof and optionally in form of the pharmacologically acceptable acid addition salts, solvates, hydrates, polymorphs, physiologically functional derivatives or prodrugs thereof, for the preparation of a pharmaceutical composition for the treatment of autoimmune disorders selected from the group consisting of amyloidosis, systemic lupus erythematosus, rheumatoid arthritis, Crohn's disease, multiple sclerosis, systemic sclerosis (scleroderma), mixed connective tissue disease, Sjögren's syndrome, ankylosing spondylitis, autoimmune vasculitis, Behcet's syndrome, psoriasis, autoimmune arthritis, sarcoidosis and diabetes mellitus.

In a further embodiment the invention relates to the use of a compound of Formula (I) according to the invention, optionally in form of its tautomers, racemates, enantiomers, diastereomers and the mixtures thereof and optionally in form of the pharmacologically acceptable acid addition salts, solvates, hydrates, polymorphs, physiologically functional derivatives or prodrugs thereof, for the preparation of a pharmaceutical composition for the treatment of fungous diseases including but not limited to candidiasis, cryptococcosis, aspergillosis, mucormycosis, tinea, dermatophytosis, histoplasmosis, blastomycosis, coccidiosis, *pneumocystis.*

Homologous genes encoding polo-like kinases have been identified from various eukaryotes ranging from fungi (*S. cerevisiae, S. pombe, C. albicans*), fly (*D. melanogaster*), worms (*C. elegans*) and vertebrates and represent a central mechanism to regulate mitotic progression (Glover et al. 1996, J Cell Biol, 135, pages 1681-1684, Bachewich et al. 2003, Mol Biol Cell 14, pages 2163-2180). Thus, the preferentially local or systemic administration of a therapeutically effective amount of a compound of Formula (I), optionally in form of its tautomers, racemates, enantiomers, diastereomers and the mixtures thereof and optionally in form of the pharmacologically acceptable acid addition salts, solvates, hydrates, polymorphs or physiologically functional derivatives thereof, represents a novel approach for treating fungous diseases.

In a further embodiment the invention relates to a method for treating a disease characterized by abnormal cell proliferation in a human or non-human mammalian body comprising administering to the mammal a therapeutically effective amount of a compound of Formula (I), optionally in form of its tautomers, racemates, enantiomers, diastereomers and the mixtures thereof and optionally in form of the pharmacologically acceptable acid addition salts, solvates, hydrates, polymorphs or physiologically functional derivatives thereof.

In a further embodiment the invention relates to a method for treating patients who suffer from one or more diseases cited above comprising administering to the patient a therapeutically effective amount of a compound of Formula (I), optionally in form of its tautomers, racemates, enantiomers, diastereomers and the mixtures thereof and optionally in form of the pharmacologically acceptable acid addition salts, solvates, hydrates, polymorphs or physiologically functional derivatives thereof.

A method for treating a disease characterized by abnormal cell proliferation in a human or non-human mammalian body by inhibition of polo like kinases as mitotic regulators in a mammal comprises regulating, modulating, binding or inhibiting PLK activity and/or overexpression of PLK or one of the other PLK isoforms, preferably PLK-1

In a further embodiment the invention relates to the use of a compound of Formula (I) according to the invention, optionally in form of its tautomers, racemates, enantiomers, diastereomers and the mixtures thereof and optionally in form of the pharmacologically acceptable acid addition salts, solvates, hydrates, polymorphs or physiologically functional derivatives thereof, wherein the active ingredient is administered orally, enterically, transdermally, intravenously, peritoneally or by injection, preferably intravenously.

Within the meaning of the present invention, a compound of Formula (I), optionally in form of its tautomers, racemates, enantiomers, diastereomers and the mixtures thereof and optionally in form of the pharmacologically acceptable acid addition salts, solvates, hydrates, polymorphs, physiologically functional derivatives or prodrugs thereof, inhibits the proliferation of various human tumor cell lines including but not limited to Saos-2, H4, MDA-MB-435S, MDA-MB453, MCF7, HeLa S3, HCT116, Colo 205, HT29, FaDu, HL-60, K-562, THP-1, HepG2, A549, NCI-H460, NCI-H520, GRANTA-519, Raji, Ramos, BRO, SKOV-3, BxPC-3, Mia CaPa-2, DU145, PC-3, NCI-N87, MES-SA, SK-UT-1B and A431.

The following example illustrates the present invention without restricting its scope.

The activity of 4-[[(7R)-8-cyclopentyl-7-ethyl-5,6,7,8-tetrahydro-5-methyl-6-oxo-2-pteridinyl]amino]-3-methoxy-N-(1-methyl-4-piperidinyl)-benzamide, which is a compound of Formula (I) according to the invention (Exemplified compound Nr. 46 in Table 2) can be determined in cytotoxicity tests on cultivated human tumour cells and/or by FACS analysis where its inhibitory effect on cell cycle progression is monitored. In both test methods, this compound exhibits a good to very good activity (see Table 1).

Alamar Blue™ Cytotoxicity Assays

The Alamar Blue™ assay is designed to measure quantitatively the proliferation of cells by incorporating a fluorometric/colorimetric growth indicator based on the detection of metabolic activity.

Cell culture: The various human tumor cell lines can be purchased from American Type Culture Collection (ATCC) or the German Collection of Microorganisms and Cell Cultures (DSMZ) and cultivated in 75 to 175 $cm^2$ tissue culture flasks in the medium indicated by the supplier. The cells are maintained at 37° C. and 5% $CO_2$ in a humidified atmosphere, with an appropriate split ratio. Logarithmically growing cells are used for the assays.

Assay conditions: On day one of the experiment 1000-4000 cells (in 100 µl medium) are seeded into each well of a sterile 96-well plate. The number of cells used is dependent on the growth rate and size of the cells. Eight wells on each plate are left free to accommodate for controls (4 wells for medium plus reduced AlamarBlue™, and 4 wells for medium plus oxidized AlamarBlue™). The plates are kept in the incubator overnight. On day two of the experiment serial dilutions of the inhibitor are prepared in medium containing 0.1% DMSO. Typical concentrations used are 10, 3, 1, 0.3, 0.1, 0.03, 0.01, 0.003 and 0.001 µM. 100 µl of the dilution (2× concentrate) is added to each well to yield a final volume of 200 µl per well. As controls plain medium and medium containing 0.1% DMSO are added to the designated wells. All data points are done in quadruplicates. The cells are then incubated for 72 h. After this incubation period 20 µl of AlamarBlue™ is added to each well. As a control, 20 µl of reduced AlamarBlue™ (AlamarBlue™ autoclaved for 30 min) is added to 4 wells without cells, and 20 µl of AlamarBlue™ is added to the remaining 4 wells without cells. After 4-5 h of incubation, the plates are measured in a fluorescence spectrophotometer (excitation 530 nm, emission 590 nm, slits 15, integrate time 0.1).

Data analysis: For calculation the mean value from the quadruplicates is taken and the background is subtracted. The 0.1% DMSO value (the mean obtained from 8 wells with cells in medium with 0.1% DMSO but no compound) is taken as 100% control. The data is fitted by iterative calculations using a sigmoidal curve analysis program (Graph Pad Prism version 3.03) with variable Hill slope.

FACS Analysis on PI Stained Tumor Cells

Propidium iodine (PI) binds stoichiometrically to double stranded DNA and thus is a suitable agent to measure the DNA content of cells in order to determine the percentage of cells residing in various cell cycle stages (G0/1-, S- and G2/M-phases), whereas cells in G0 or G1 phase do have a diploid DNA content (2N) cells in G2 and M-phase (mitosis) do have a doubled (4N) DNA content.

Cell culture: The various human tumor cell lines can be purchased from American Type Culture Collection (ATCC) or the German Collection of Microorganisms and Cell Cultures (DSMZ) and cultivated in 75 to 175 cm$^2$ tissue culture flasks in the medium indicated by the supplier. The cells are maintained at 37° C. and 5% $CO_2$ in a humidified atmosphere, with an appropriate split ratio. Logarithmically growing cells are used for the assays.

Assay conditions: On day one of the experiment 1×10$^6$ tumor cells are plated in 15 ml medium onto each 75 cm$^2$ tissue culture flask and the cultures are returned to the incubator. On the next day serial twofold dilutions (100× concentrated) of the inhibitor are prepared in tissue culture medium containing 10% DMSO. 150 µl of the 100× concentrated dilution is added to the 15 ml medium in the flask. As control DMSO is given into a separate flask to yield a final concentration of 0.1%. Typical final concentrations used are 1.6, 08, 0.4, 0.2, 0.1, 0.05, 0.025, 0.0125, 0.00625 µM in medium containing 0.1% DMSO. After 24 hrs of incubation cells are harvested by 2× wash with PBS and subsequent addition of trypsin/EDTA. Trypsinized cells are washed off the plastic with 1% BSA in PBS. Non-adherent cells in the medium and cells in the PBS wash fluids are pelleted together with the trypsinized cells by centrifuging them for 5 min at 1000 rpm at 4° C. The supernatants are discarded and the pellet is washed twice with PBS. After aspiration of the supernatants pellets are resuspended in the residual PBS (~100 µl). For cold fixation, 15 ml test tubes (Falcon) with 5 ml of 80% cold ethanol are prepared and the cell suspension is added slowly and kept for at least 2 h or overnight at minus 20° C. Fixed cells are pelleted, washed once with PBS and the cell pellet is then resuspended in 2 ml of 0.25% Triton X-100 in PBS. After 5 min incubation on ice, 5 ml of PBS is added to each sample and the sample is again centrifuged at 1000 rpm for 5 min at 4° C. The supernatant is discarded and the pellet is resuspended in 0.5 ml propidium iodine (PI) staining solution (0.1% RNase and 10 µg/ml propidium iodium in PBS). The cells are incubated for 20 min in the dark and subsequently transferred to 5 ml polystyrene round-bottom tubes.

Data analysis: Analysis of the DNA content of the cells can be performed using a FACS analyzer equipped with an argon laser (500 mW, emission 488 nm) and the use of the DNA Cell Quest analysis software (Beckton Dickinson). The logarithmic PI fluorescence is determined in a band-pass filter (Beckton Dickinson 585/43). Quantification of the cell populations residing in the individual cell cycle phases (e.g. G0/G1-, S- and G2/M-phases) is done with the ModFit LT software package from Becton Dickinson. An $EC_{50}$ value for cells arrested at the G2/M-phase of the cell cycle is calculated by using a sigmoidal curve analysis program (Graph Pad Prism version 3.03).

TABLE 1

In vitro efficacy data of 4-[[(7R)-8-cyclopentyl-7-ethyl-5,6,7,8-tetrahydro-5-methyl-6-oxo-2-pteridinyl]amino]-3-methoxy-N-(1-methyl-4-piperidinyl)-benzamide

| Tissue origin | Cell lines | Alamar Blue Cytotoxicity Assay EC50 [µM] | FACS Analysis G2M-Arrest EC50 [µM] |
| --- | --- | --- | --- |
| Bone | Saos-2 | 0.008 | 0.011 |
| Brain | H4 | 0.022 | 0.039 |
| Breast | MDA-MB-435S | 0.017 | 0.038 |
|  | MCF7 | 0.009 |  |
| Cervix | HeLa S3 | 0.012 | 0.016 |
| Colon | HCT116 | 0.009 | 0.009 |
|  | Colo 205 | 0.009 |  |
|  | HT29 | 0.004 |  |
| Head and Neck | FaDu | 0.006 | 0.007 |
| Leukemia | HL-60 | 0.014 |  |
|  | THP-1 | 0.009 |  |
| Liver | HepG2 | 0.010 | 0.039 |
| Lung | A549 | 0.006 | 0.014 |
|  | NCI-H460 | 0.014 | 0.032 |
|  | NCI-H520 | 0.010 | 0.018 |
| Lymphoma | GRANTA-519 | 0.005 | 0.012 |
|  | Raji | 0.014 | 0.020 |
| Melanoma | BRO | 0.004 |  |
| Ovary | SKOV-3 | 0.004 | 0.011 |
| Pancreas | BxPC-3 | 0.025 | 0.022 |
|  | Mia CaPa-2 | 0.007 |  |
| Prostate | DU145 | 0.006 |  |
|  | PC-3 | 0.007 | 0.012 |
| Stomach | NCI-N87 | 0.014 |  |
| Uterus | MES-SA | 0.010 |  |
|  | SK-UT-1B | 0.008 |  |
| Vulva | A431 | 0.002 | 0.006 |

A compound of Formula (I), its tautomers, the racemates, the enantiomers, the diastereomers and the mixtures thereof, and optionally the pharmacologically acceptable acid addition salts, solvates, hydrates, polymorphs, physiologically functional derivatives or prodrugs thereof, may be used on their own or combined with other active substances according to the invention, optionally also in conjunction with other pharmacologically active substances.

Suitable pharmaceutical preparations for the use in accordance with the invention include, for example, tablets, capsules, suppositories, solutions, and particularly solutions for injection (s.c., i.v., i.m.) and infusion, syrups, emulsions or dispersible powders. The amount of pharmaceutically active compound in each case should be in the range from 0.1-90 wt. %, preferably 0.5-50 wt. % of the total composition, i.e. in amounts which are sufficient to achieve the dosage range given below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharin, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of preservatives such as p-hydroxybenzoates, or stabilisers such as alkali metal salts of ethylenediamine tetraacetic acid, optionally using emulsifiers and/or dispersants, while if water is used as the diluent organic solvents may optionally be used as solubilisers or auxiliary solvents, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Suitable excipients may be, for example, water, pharmaceutically acceptable organic solvents, such as paraffins (e.g. petroleum fractions), oils of vegetable origin (e.g. groundnut or sesame oil), mono- or polyfunctional alcohols (e.g. ethanol or glycerol), carriers such as e.g. natural mineral powders (e.g. kaolin, clays, talc, chalk), synthetic mineral powders (e.g. highly dispersed silica and silicates), sugar (e.g. glucose, lactose and dextrose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered in the usual way, preferably by oral or transdermal route, particularly preferably by oral route. When administered orally the tablets may, of course, contain additives, such as e.g. sodium citrate, calcium carbonate and dicalcium phosphate together with various additives, such as starch, preferably potato starch, gelatine and the like, in addition to the abovementioned carriers. Lubricants such as magnesium stearate, sodium laurylsulphate and talc may also be used to form tablets. In the case of aqueous suspensions the active substances may be combined with various flavour enhancers or colourings in addition to the abovementioned excipients. For parenteral use, solutions of the active substances may be prepared using suitable liquid carrier materials.

The dosage for intravenous use is 1-2000 mg per hour, preferably between 5-1000 mg per hour.

However, it may optionally be necessary to deviate from the amounts specified, depending on the body weight or method of administration, the individual response to the medication, the nature of the formulation used and the time or interval over which it is administered. Thus, in some cases, it may be sufficient to use less than the minimum quantity specified above, while in other cases the upper limit specified will have to be exceeded. When large amounts are administered it may be advisable to spread them over the day in a number of single doses.

The formulation examples that follow illustrate the present invention without restricting its scope:

EXAMPLES OF PHARMACEUTICAL FORMULATIONS

| A) Tablets | per tablet |
|---|---|
| active substance | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | per tablet |
|---|---|
| active substance | 80 mg |
| lactose | 55 mg |
| corn starch | 190 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium carboxymethyl starch and the magnesium stearate are added and mixed in and the mixture is compressed to form tablets of a suitable size.

| C) Ampoule solution | |
| --- | --- |
| active substance | 50 mg |
| sodium chloride | 50 mg |
| water for injection | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

| D) Further injectable solutions | | | |
| --- | --- | --- | --- |
| Example 1 | | Example 2 | |
| Active substance | 2 mg/ml | Active substance | 10.0000 g |
| Hydrochloric acid 1N | 6.8 µl | Hydrochloric acid 1N | 36.6735 g |
| NaCl | 0.009 g/ml | NaCl | 45.0000 g |
| WFI (water for injection) ad | 1 ml | WFI | 4934.8265 g |
| pH | 4.5 | pH | 4.3 |
| mOsmol/kg | 295 | mOsmol/kg | 300 |
| Example 3 | | Example 4 | |
| Active susbtance | 500 mg | Active susbtance | 0.5 mg |
| Hydrochloric acid 1N | 1.6 ml | Hydrochloric acid 1N | 1.705 µl |
| NaCl | 450.0 mg | NaCl | 9 mg |
| WFI ad | 50 ml | WFI ad | 1 ml |
| pH | 4.0 | pH | 4.8 |
| mOsmol/kg | 290 | mOsmol/kg | 285 |
| Example 5 | | Example 6 | |
| Active susbtance | 1 mg | Active susbtance | 2 mg |
| Hydrochloric acid 1N | 3.6125 µl | Phosphoric acid (85%) | 0.440 µl |
| NaCl | 0.009 g | NaCl | 9 mg |
| WFI ad | 1 ml | WFI ad | 1 ml |
| pH | 4.8 | pH | 4.0 |
| mOsmol/kg | 295 | mOsmol/kg | 298 |
| Example 7 | | Example 8 | |
| Active susbtance | 100 mg | Active susbtance | 10 mg |
| Acetic acid | 16.4 µl | Tartaric acid | 4.32 mg |
| Dextrose | 2.5 g | Mannit | 0.25 g |
| WFI ad | 50 ml | WFI ad | 5 ml |
| pH | 4.4 | pH | 4.0 |
| mOsmol/kg | 305 | mOsmol/kg | 298 |

A process for the manufacture of the compound 4-[[(7R)-8-cyclopentyl-7-ethyl-5,6,7,8-tetrahydro-5-methyl-6-oxo-2-pteridinyl]amino]-3-methoxy-N-(1-methyl-4-piperidinyl)-benzamide is described in WO 03/20722 as well as in WO 04/76454, which are incorporated herein by reference.

However, for the sake of completeness, a process for the manufacture of the compound 4-[[(7R)-8-cyclopentyl-7-ethyl-5,6,7,8-tetrahydro-5-methyl-6-oxo-2-pteridinyl]amino]-3-methoxy-N-(1-methyl-4-piperidinyl)-benzamide is described as well hereinafter. This method is to be understood as an illustration of the invention without restricting it to the subject matter thereof.

Synthesis of 4-[[(7R)-8-cyclopentyl-7-ethyl-5,6,7,8-tetrahydro-5-methyl-6-oxo-2-pteridinyl]amino]-3-methoxy-N-(1-methyl-4-piperidinyl)-benzamide For the synthesis, first of all an intermediate compound Z3 is prepared as described below.

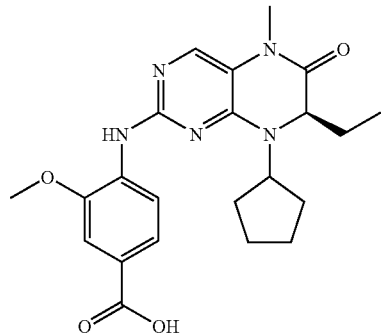

54.0 g (0.52 mol) D-2-aminobutyric acid are suspended in 540 mL methanol and slowly combined with 132 g (1.1 mol) thionyl chloride while cooling with ice. The mixture is refluxed for 1.5 h and then evaporated down. The oil remaining is combined with 540 mL tert-butylmethylether and the colourless crystals formed are suction filtered.

Yield: 78.8 g of a compound Z3a (colourless crystals)

74.2 g of the compound Z3a and 43.5 mL (0.49 mol) cyclopentanone are dissolved in 800 mL dichloromethane. After the addition of 40.0 g (0.49 mol) sodium acetate and 150.0 g (0.71 mol) sodium triacetoxyborohydride at 0° C. the mixture is stirred for 12 h at ambient temperature and then 500 mL of 20% sodium hydrogen carbonate solution are added. The aqueous phase is extracted with dichloromethane. The combined organic phases are washed with water, dried over $MgSO_4$ and evaporated down.

Yield: 85.8 g of a compound Z3b (light yellow oil)

40.0 g of the compound Z3b and 30.0 g (0.22 mol) potassium carbonate are suspended in 600 mL acetone and combined with 45.0 g (0.23 mol) 2,4-dichloro-5-nitropyrimidin in 200 mL acetone while cooling with ice. After 12 h a further 5.0 g 2,4-dichloro-5-nitropyrimidin are added and stirred for 3 h. The reaction mixture is evaporated down, taken up in 800 mL ethyl acetate and 600 mL water and the aqueous phase is extracted with ethyl acetate. The combined organic phases are washed with water, dried over $MgSO_4$ and evaporated down.

Yield: 75.0 g of a compound Z3c (brown oil)

100 g of the compound Z3c are dissolved in 650 mL glacial acetic acid and at 70° C. 20 g of iron powder are added batchwise. The mixture is stirred for 1 h at 70° C., then for 1.5 h at 100° C. and then filtered hot through diatomite (kieselguhr). The reaction mixture is evaporated down, taken up in methanol/dichloromethane, applied to silica gel and purified with ethyl acetate by Soxhlet extraction. The solvent is removed and the residue stirred with methanol.

Yield: 30.0 g of a compound Z3d (light brown crystals)

25.0 g of the compound Z3d and 6.5 mL (0.1 mol) methyl iodide are placed in 250 mL dimethylacetamide and at −10° C. 3.8 g (0.95 mol) sodium hydride as a 60% dispersion in mineral oil is added. It is stirred for 20 min at 0° C., then for 30 min at ambient temperature and finally ice is added. The reaction mixture is evaporated down and combined with 300 mL water. The precipitate formed is suction filtered and washed with petroleum ether.

Yield: 23.0 g of a compound Z3e (colourless solid)

6.0 g of the compound Z3e and 5.1 g (31 mmol) 4-amino-3-methoxybenzoic acid are suspended in 90 mL ethanol and 350 mL water, combined with 3.5 mL concentrated hydrochloric acid and refluxed for 48 h. The reaction mixture is evaporated down, the residue stirred with methanol/diethyl ether and the precipitate formed is suction filtered.

Yield: 6.3 g of a compound Z3 (light beige crystals)

4-[[(7R)-8-cyclopentyl-7-ethyl-5,6,7,8-tetrahydro-5-methyl-6-oxo-2-pteridinyl]amino]-3-methoxy-N-(1-methyl-4-piperidinyl)-benzamide is obtained as described below.

0.15 g of the compound Z3, 0.12 g TBTU, 0.12 mL DIPEA are dissolved in 5 mL dichloromethane and stirred for 30 minutes at 25° C. Then 50 mg 1-methyl-4-aminopiperidin are added and the mixture is stirred for a further 2.5 hours at 25° C. The solution is then extracted with water and then evaporated down. The residue is dissolved in warm ethyl acetate and crystallised from ether and petroleum ether.

Yield: 0.025 g of white crystals. M.p.: 203° C. as the base.

All compounds of Formula (I) according to the invention may be prepared by the synthesis methods A described hereinafter, while the substituents of general Formula (A1) to (A9) have the meanings given hereinbefore. This method is to be understood as an illustration of the invention without restricting it to the subject matter thereof.

Method A

Step 1A

A compound of Formula (A1) is reacted with a compound of Formula (A2) to obtain a compound of Formula (A3) (Diagram 1A). This reaction may be carried out according to WO 00/43369 or WO 00/43372. Compound (A1) is commercially obtainable, for example, from City Chemical LLC, 139 Allings Crossing Road, West Haven, Conn., 06516, USA. Compound (A2) may be prepared by procedures known from the literature: (a) F. Effenberger, U. Burkhart, J. Willfahrt *Liebigs Ann. Chem.* 1986, 314-333; (b) T. Fukuyama, C.-K. Jow, M. Cheung, *Tetrahedron Lett.* 1995, 36, 6373-6374; (c) R. K. Olsen, *J. Org. Chem.* 1970, 35, 1912-1915; (d) F. E. Dutton, B. H. Byung *Tetrahedron Lett.* 1998, 30, 5313-5316; (e) J. M. Ranajuhi, M. M. Joullie *Synth. Commun.* 1996, 26, 1379-1384).

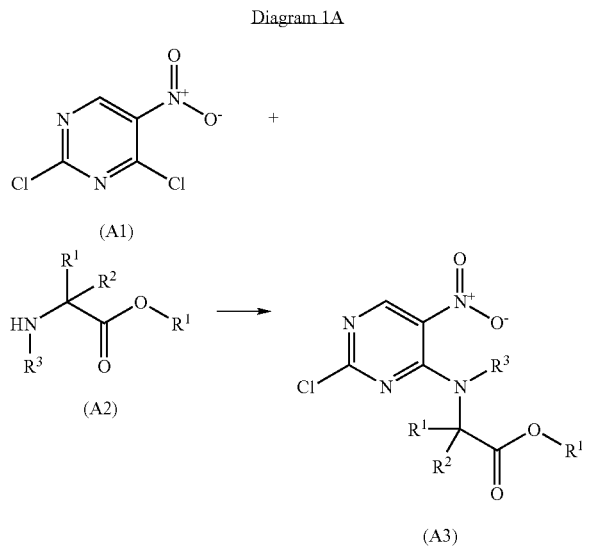

Diagram 1A

In Step 1A, 1 equivalent of the compound (A1) and 1 to 1.5 equivalents, preferably 1.1 equivalents of a base, preferably potassium carbonate, potassium hydrogen carbonate, sodium carbonate or sodium hydrogen carbonate, calcium carbonate, most preferably potassium carbonate, are stirred in a diluent optionally mixed with water, for example acetone, tetrahydrofuran, diethylether, cyclohexane, petroleum ether or dioxane, preferably cyclohexane or diethylether.

At a temperature of 0 to 15° C., preferably 5 to 10° C., 1 equivalent of an amino acid of Formula (A2), dissolved in an organic solvent, for example acetone, tetrahydrofurane, diethylether, cyclohexane or dioxane, is added dropwise. The reaction mixture is heated to a temperature of 18° C. to 30° C., preferably about 22° C., with stirring and then stirred for a further 10 to 24 hours, preferably about 12 hours. Then the diluent is distilled off, the residue is combined with water and the mixture is extracted two to three times with an organic solvent, such as diethylether or ethyl acetate, preferably ethyl acetate. The combined organic extracts are dried and the solvent is distilled off. The residue (compound A3) may be used in Step 2 without any prior purification.

Step 2A

The compound obtained in Step 1A (A3) is reduced at the nitro group and cyclised to form the compound of Formula (A4) (Diagram 2A).

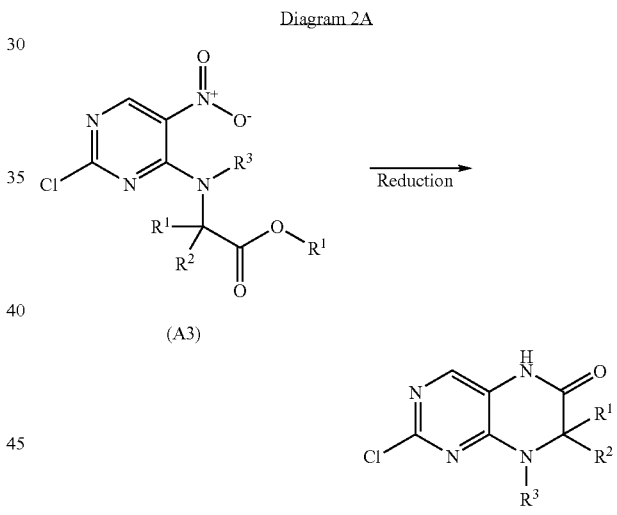

Diagram 2A

In Step 2A, 1 equivalent of the nitro compound (A3) is dissolved in an acid, preferably glacial acetic acid, formic acid or hydrochloric acid, preferably glacial acetic acid, and heated to 50 to 70° C., preferably about 60° C. Then a reducing agent, for example zinc, tin or iron, preferably iron filings, is added to complete the exothermic reaction and the mixture is stirred for 0.2 to 2 hours, preferably 0.5 hours, at 100 to 125° C., preferably at about 117° C. After cooling to ambient temperature the iron salt is filtered off and the solvent is distilled off. The residue is taken up in a solvent or mixture of solvents, for example ethyl acetate or dichloromethane/methanol 9/1 and semisaturated NaCl solution, and filtered through kieselgur, for example. The organic phase is dried and evaporated down. The residue (compound (A4)) may be purified by chromatography or by crystallisation or used as the crude product in Step 3A of the synthesis.

Step 3A

The compound obtained in Step 2A (A4) may be reacted by electrophilic substitution as shown in Diagram 3A to obtain the compound of Formula (A5).

Diagram 3A

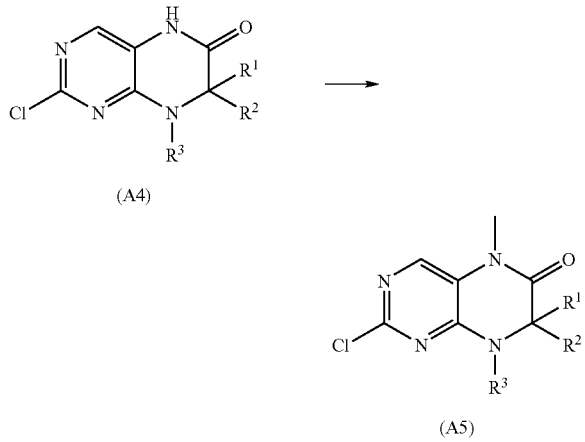

In Step 3A 1 equivalent of the amide of Formula (A4) is dissolved in an organic solvent, for example dimethylformamide or dimethylacetamide, preferably dimethylacetamide, and cooled to about −5 to 5° C., preferably 0° C.

Then 0.9 to 1.3 equivalents of sodium hydride and 0.9 to 1.3 equivalents of a methylating reagent, e.g. methyl iodide, are added. The reaction mixture is stirred for 0.1-3 hours, preferably about 1 hour, at about 0 to 10° C., preferably at about 5° C., and may optionally be left to stand for a further 12 hours at this temperature. The reaction mixture is poured onto ice water and the precipitate is isolated. The residue (compound (A5)) may be purified by chromatography, preferably over silica gel, or by crystallisation, or used as the crude product in step 4A of the synthesis.

Step 4A

The amination of the compound (A5) obtained in Step 3A to yield the compound of Formula (A9) (Diagram 4A) may be carried out using the methods known from the literature, for variants 4.1 A from e.g. (a) M. P. V. Boarland, J. F. W. McOmie *J. Chem. Soc.* 1951, 1218-1221 or (b) F. H. S. Curd, F. C. Rose *J. Chem. Soc.* 1946, 343-348, for variants 4.2 A from e.g. (a) Banks *J. Am. Chem. Soc.* 1944, 66, 1131, (b) Ghosh and Dolly *J. Indian Chem. Soc.* 1981, 58, 512-513 or (c) N. P. Reddy and M. Tanaka *Tetrahedron Lett.* 1997, 38, 4807-4810.

Diagram 4A

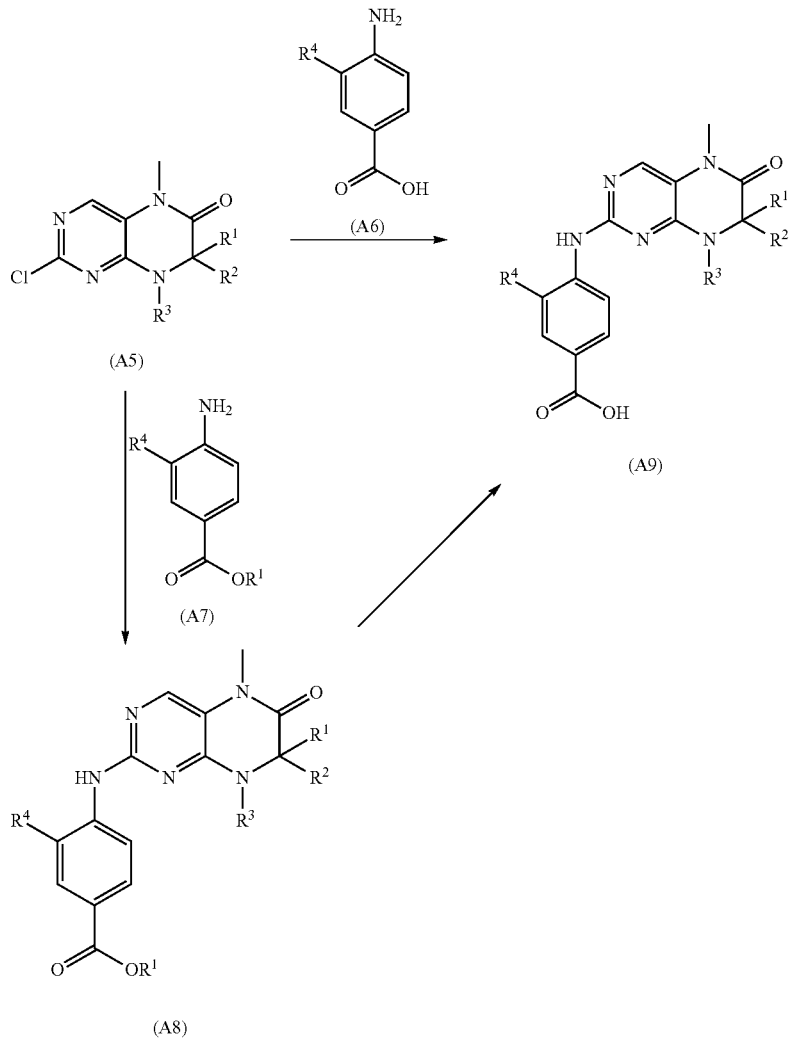

For example, in variant 4.1 A, 1 equivalent of the compound (A5) and 1 to 3 equivalents, preferably about 2 equivalents of the compound (A6) are heated without a solvent or in an organic solvent such as for example sulpholane, dimethylformamide, dimethylacetamide, toluene, N-methylpyrrolidone, dimethylsulphoxide or dioxane, preferably sulpholane, for 0.1 to 4 hours, preferably 1 hour, at 100 to 220° C., preferably at about 160° C. After cooling, the product (A9) is crystallised by the addition of organic solvents or mixtures of solvents, e.g. diethylether/methanol, ethyl acetate, methylene chloride, or diethylether, preferably diethylether/methanol 9/1, or purified by chromatography.

For example, in variant 4.2 A, 1 equivalent of the compound (A5) and 1 to 3 equivalents of the compound (A6) are stirred with acid, for example 1-10 equivalents of 10-38% hydrochloric acid and/or an alcohol, for example ethanol, propanol, butanol, preferably ethanol, at reflux temperature for 1 to 48 hours, preferably about 5 hours. The product precipitated (A9) is filtered off and optionally washed with water, dried and crystallised from a suitable organic solvent.

For example, in variant 4.3 A, 1 equivalent of the compound (A5) and 1 to 3 equivalents of the compound (A7) are dissolved in a solvent, for example toluene or dioxane and combined with a phosphine ligand, for example 2, 2'-bis-(diphenylphosphino)-1,1'-binaphthyl and a palladium catalyst, for example tris(dibenzylidene-acetone)-dipalladium(0) and a base, for example caesium carbonate, and refluxed for 1-24 h, preferably 17 h. The reaction mixture is purified for example over silica gel and the product (A8) is isolated from the solution or obtained by suitable crystallisation. The product (A8) is dissolved in a suitable solvent, for example dioxane and mixed with acid, for example semiconcentrated hydrochloric acid, for example in the ratio of solvent to acid of 3:1. Then the mixture is refluxed for 1-48 h, for example 12 h, and the precipitate formed is isolated. If desired the product (A9) is purified by crystallisation.

Step 5A

Diagram 5A

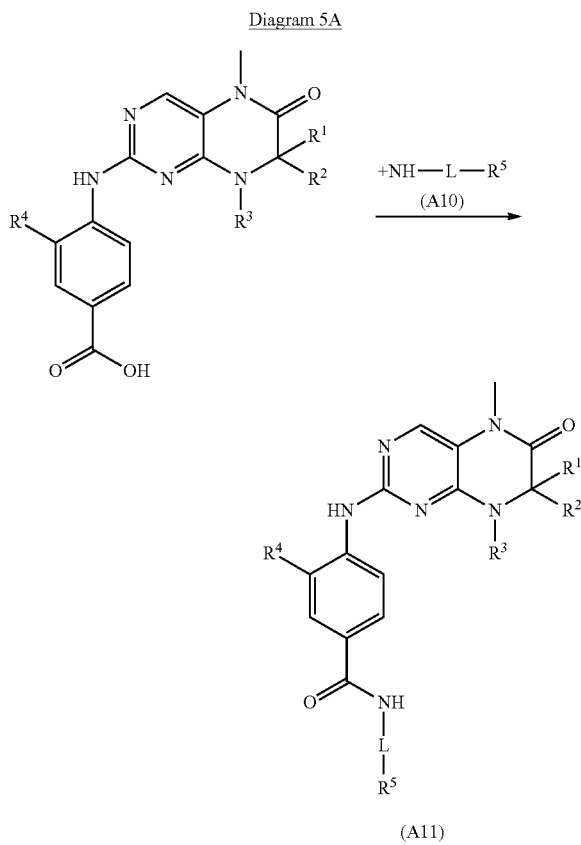

For example, 1 equivalent of the compound (A9) is dissolved with 1 equivalent of an activating reagent, e.g. O-benzotriazolyl-N,N,N',N'-tetramethyluronium tetrafluoroborate (TBTU) and a base, for example 1.5 equivalents of diisopropylethylamine (DIPEA) in an organic diluent, for example dichloromethane, tetrahydrofuran, dimethylformamide, N-methylpyrrolidone, dimethylacetamide, preferably dichloromethane or dimethylformamide. After the addition of 1 equivalent of the amine (A10) the reaction mixture is stirred for 0.1 to 24 hours, preferably about 2 hours at 20° C. to 100° C. The product of Formula (A11) is obtained for example by crystallisation or chromatographic purification.

The compounds of general Formula (I) may be synthesised analogously to the following examples of synthesis. The numbering of the Examples corresponds to the numbering used in Table 2. These Examples are, however, intended only as examples of procedures to illustrate the invention further, without restricting the invention to their subject matter.

The preparation of some intermediate compounds used to synthesise the compounds is also described hereinafter.

Preparation of the Acids

To synthesise the compounds of Examples 94 and 95 of Table 2, first an intermediate compound Z1

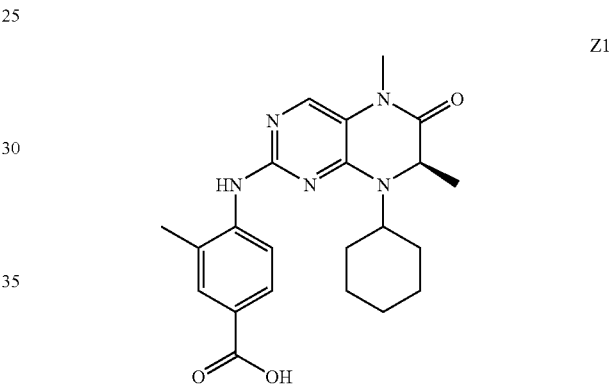

is prepared as described hereinafter.

50.0 g (0.48 mol) of D-alanine methyl ester×HCl and 49.1 g (0.50 mol) cyclohexanone are placed in 300 mL dichloromethane and then combined with 41.0 g (0.50 mol) sodium acetate and 159.0 g (0.75 mol) sodium triacetoxyborohydride. The mixture is stirred overnight and then 300 mL of 10% sodium hydrogen carbonate solution are added. The aqueous phase is extracted with dichloromethane. The combined organic phases are washed with 10% sodium hydrogen carbonate solution, dried over $Na_2SO_4$ and evaporated down.

Yield: 72.5 g of a compound Z1a (clear liquid)

72.5 g of the compound Z1a are placed in 500 mL water and 76.6 g (0.39 mol) of 2,4-dichloro-5-nitropyrimidine in 500 mL diethyl ether are added. At a temperature of −5° C. 100 mL 10% potassium hydrogen carbonate solution are added dropwise. The mixture is stirred for 3 h at −5° C. and for a further 12 h at ambient temperature. The organic phase is separated off and dried over $Na_2SO_4$. On evaporation, the product crystallizes out.

Yield: 48.0 g of a compound Z1b (yellow crystals)

48.0 g of the compound Z1b are dissolved in 350 mL glacial acetic acid and heated to 60° C. 47.5 g of iron powder are added, while the temperature rises to 105° C. The reaction mixture is stirred for three hours at 80° C., then filtered hot through cellulose and evaporated down. The residue is stirred in water and ethyl acetate, suction filtered and the light-grey precipitate is washed with ethyl acetate. The filtrate is washed with dilute ammonia and water, the organic phase is dried over $Na_2SO_4$, filtered through activated charcoal and evaporated down. Some more light-grey solids are obtained.

Yield: 29.5 g of a compound Z1c (light-grey crystals)

32.1 g of the compound Z1c are placed in 300 mL dimethylacetamide and combined with 13 mL (0.2 mol) methyl iodide. At −5° C. 6.4 g (0.16 mol) sodium hydride as a 60% dispersion in mineral oil is added batchwise. After 2 h the reaction mixture is poured onto 800 mL ice water. The precipitate formed is suction filtered and washed with petroleum ether.

Yield: 33.0 g of a compound Z1d (beige crystals)

4.0 g of the compound Z1d and 2.3 g (15 mmol) 4-amino-3-methylbenzoic acid are suspended in 50 mL ethanol and 120 mL water, combined with 2 mL concentrated hydrochloric acid and refluxed for 48 h. The precipitate formed on cooling is suction filtered and washed with water, ethanol and diethyl ether.

Yield: 2.9 g of a compound Z1 (colourless crystals)

To synthesise the compounds Example 188 and Example 203 of Table 2, first of all an intermediate compound Z2

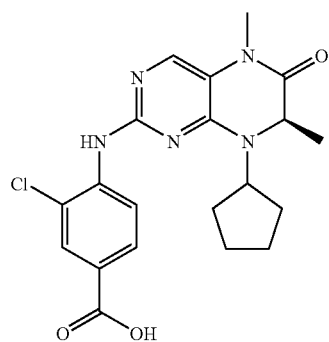

is prepared as described below.

A solution of 128.2 g (0.83 mol) D-alanine ethyl ester×HCl and 71.5 g (0.85 mol) cyclopentanone in 1500 mL dichloromethane is combined with 70.1 (0.85 mol) sodium acetate and 265.6 g (1.25 mol) sodium triacetoxyborohydride. The reaction mixture is stirred for 12 h and then poured into 1.5 L of a 10% sodium hydrogen carbonate solution. The aqueous phase is extracted with dichloromethane. The combined organic phases are dried over $Na_2SO_4$ and evaporated down.

Yield: 143.4 g of a compound Z2a (colourless oil)

66.0 g of the compound Z2a are placed in 500 mL water and combined with 85.0 g (0.44 mol) 2,4-dichloro-5-nitropyrimidine in 500 mL diethyl ether. At −5° C. 100 mL 10% potassium hydrogen carbonate solution are added dropwise and the reaction mixture is stirred for 48 h at ambient temperature. The aqueous phase is extracted with diethyl ether, the combined organic phases are dried over $Na_2SO_4$ and evaporated down. The dark red solid is stirred with petroleum ether and suction filtered.

Yield: 88.0 g of a compound Z2b (yellow crystals)

88.0 g of the compound Z2b are dissolved in 1000 mL glacial acetic acid and at 60° C. combined batchwise with 85 g iron powder, while the temperature rises to 110° C. It is stirred for 1 h at 60° C., then suction filtered hot through cellulose and evaporated down. The brown solid is stirred with 700 mL water and suction filtered.

Yield: 53.3 g of a compound Z2c (light brown crystals)

53.3 g of the compound Z2c are dissolved in 300 mL dimethylacetamide and combined with 13 mL (0.21 mol) methyl iodide. At −5° C. 5.0 g (0.21 mol) sodium hydride as a 60% dispersion in mineral oil are added batchwise. After 12 h the reaction mixture is poured onto 1000 mL ice water and the precipitate formed is suction filtered.

Yield: 40.0 g of a compound Z2d (colourless crystals)

4.0 g of the compound Z2d and 2.8 g (16 mmol) 4-amino-3-chlorbenzoic acid are suspended in 25 mL ethanol and 60 mL water, combined with 3 mL concentrated hydrochloric acid and refluxed for 43 h. The precipitate formed on cooling is suction filtered and washed with water, ethanol and diethyl ether.

Yield: 0.9 g of a compound Z2 (colourless crystals)

To synthesise the compounds of Examples 19, 21, 22, 23, 45, 46, 55, 58, 116, 128, 131, 133, 134, 136, 138, 177, 217, 231, 239, 46, 184, 166 and 187 of Table 2, first of all an intermediate compound Z3

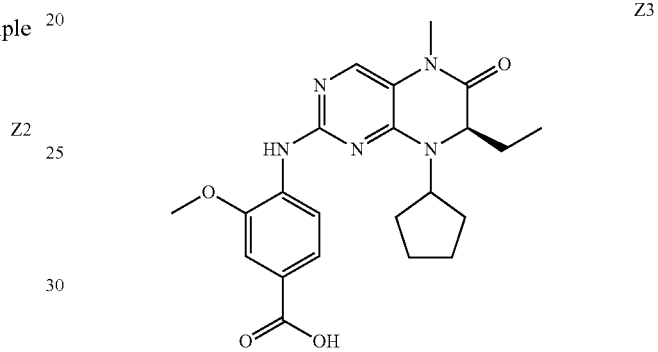

is prepared as described below.

54.0 g (0.52 mol) D-2-aminobutyric acid are suspended in 540 mL methanol and slowly combined with 132 g (1.1 mol) thionyl chloride while cooling with ice. The mixture is refluxed for 1.5 h and then evaporated down. The oil remaining is combined with 540 mL tert-butylmethylether and the colourless crystals formed are suction filtered.

Yield: 78.8 g of a compound Z3a (colourless crystals)

74.2 g of the compound Z3a and 43.5 mL (0.49 mol) cyclopentanone are dissolved in 800 mL dichloromethane. After the addition of 40.0 g (0.49 mol) sodium acetate and 150.0 g (0.71 mol) sodium triacetoxyborohydride at 0° C. the mixture is stirred for 12 h at ambient temperature and then 500 mL of 20% sodium hydrogen carbonate solution are added. The aqueous phase is extracted with dichloromethane. The combined organic phases are washed with water, dried over $MgSO_4$ and evaporated down.

Yield: 85.8 g of a compound Z3b (light yellow oil)

40.0 g of the compound Z3b and 30.0 g (0.22 mol) potassium carbonate are suspended in 600 mL acetone and combined with 45.0 g (0.23 mol) 2,4-dichloro-5-nitropyrimidin in 200 mL acetone while cooling with ice. After 12 h a further 5.0 g 2,4-dichloro-5-nitropyrimidin are added and stirred for 3 h. The reaction mixture is evaporated down, taken up in 800 mL ethyl acetate and 600 mL water and the aqueous phase is extracted with ethyl acetate. The combined organic phases are washed with water, dried over $MgSO_4$ and evaporated down.

Yield: 75.0 g of a compound Z3c (brown oil)

100 g of the compound Z3c are dissolved in 650 mL glacial acetic acid and at 70° C. 20 g of iron powder are added batchwise. The mixture is stirred for 1 h at 70° C., then for 1.5 h at 100° C. and then filtered hot through kieselgur. The reaction mixture is evaporated down, taken up in methanol/ dichloromethane, applied to silica gel and purified with ethyl acetate by Soxhlet extraction. The solvent is removed and the residue stirred with methanol.

Yield: 30.0 g of a compound Z3d (light brown crystals)

25.0 g of the compound Z3d and 6.5 mL (0.1 mol) methyl iodide are placed in 250 mL dimethylacetamide and at −10° C. 3.8 g (0.95 mol) sodium hydride as a 60% dispersion in mineral oil is added. It is stirred for 20 min at 0° C., then for 30 min at ambient temperature and finally ice is added. The reaction mixture is evaporated down and combined with 300 mL water. The precipitate formed is suction filtered and washed with petroleum ether.

Yield: 23.0 g of a compound Z3e (colourless solid)

6.0 g of the compound Z3e and 5.1 g (31 mmol) 4-amino-3-methoxybenzoic acid are suspended in 90 mL ethanol and 350 mL water, combined with 3.5 mL concentrated hydrochloric acid and refluxed for 48 h. The reaction mixture is evaporated down, the residue stirred with methanol/diethyl ether and the precipitate formed is suction filtered.

Yield: 6.3 g of a compound Z3 (light beige crystals)

To synthesise the compound of Examples 81, 82, 93 and 137 of Table 2, first of all an intermediate compound Z4

Z4

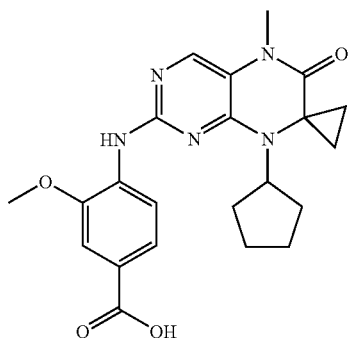

is prepared as described below.

25.0 g (0.19 mol) of ethyl 1-aminocyclopropane-1-carboxylate×HCl and 16.8 g (0.20 mol) of cyclopentanone are dissolved in 300 mL of dichloromethane and combined with 16.4 g (0.20 mol) of sodium acetate and 61.7 g (0.29 mol) of sodium triacetoxyborohydride. It is stirred overnight and the reaction mixture is then poured onto 400 mL of 10% sodium hydrogen carbonate solution. The aqueous phase is extracted with dichloromethane. The combined organic phases are dried over $Na_2SO_4$ and evaporated down.

Yield: 34.5 g of a compound Z4a (colourless oil)

42.5 g (0.22 mol) of 2,4-dichloro-5-nitropyrimidine in 350 mL of diethyl ether are added to a mixture of 34.5 g of the compound Z4a in 350 mL water. At −5° C. the mixture is combined with 80 mL 10% potassium hydrogen carbonate solution and stirred overnight at ambient temperature. The aqueous phase is extracted with diethyl ether. The combined organic phases are dried over $Na_2SO_4$ and evaporated down.

Yield: 53.8 g of a compound Z4b (brown oil)

20.1 g of the compound Z4b are dissolved in 200 mL glacial acetic acid and combined batchwise at 60° C. with 19.1 g iron powder, during which time the temperature rose to 100° C. The mixture is stirred for 3 h at 60° C., then suction filtered through cellulose and evaporated down. The residue is stirred in water and ethyl acetate and the yellow precipitate is suction filtered. The filtrate is washed with dilute ammonia and water, the organic phase dried over $Na_2SO_4$ and evaporated down. After the addition of diethyl ether additional product crystallised out.

Yield: 4.0 g of a compound Z4c (yellow crystals)

7.8 g of the compound Z4c and 2.6 mL (0.04 mol) methyl iodide are dissolved in 100 mL dimethylacetamide and at −5° C. 1.5 g (0.04 mol) sodium hydride are added batchwise as a 60% dispersion in mineral oil. After 2 h the reaction mixture is poured onto ice water and the precipitate formed is suction filtered.

Yield: 7.5 g of a compound Z4d (light brown crystals)

3.0 g of the compound Z4d and 1.9 g (11 mmol) 4-amino-3-methoxybenzoic acid are suspended in 40 mL ethanol and 80 mL water, combined with 2 mL concentrated hydrochloric acid and refluxed for 20 h. A further 0.5 g of 4-amino-3-methoxybenzoic acid are added and refluxed for 48 h. The precipitate formed on cooling is suction filtered and washed with water, ethanol and diethyl ether.

Yield: 2.1 g of a compound Z4 (colourless crystals) m.p.: 222-223° C.

To synthesise the compounds of Examples 162, 43, 53, 161, 202, 211, 215 and 212 of Table 2, first of all an intermediate compound Z5

Z5

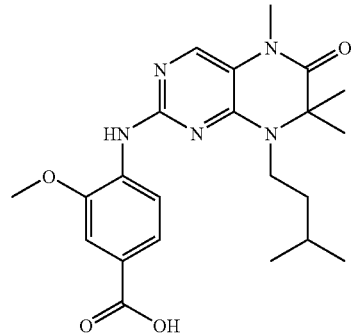

is prepared as described below.

A mixture of 73.4 mL (0.5 mol) ethyl 2-bromoisobutyrate, 87.1 mL (0.75 mol) of 3-methyl-1-butylamine, 82.5 g (0.6 mol) sodium iodide and 76.0 g (0.6 mol) of potassium carbonate in 1000 mL ethyl acetate is refluxed for 3 days. Any salts present are filtered off and the filtrate evaporated down.

Yield: 97.0 g of a compound Z5a (red oil)

49.0 g (0.25 mol) of 2,4-dichloro-5-nitropyrimidine and 38.3 g (0.28 mol) of potassium carbonate are suspended in 500 mL acetone and at 0° C. combined with 93.0 g of the compound Z5a in 375 mL acetone. The reaction mixture is stirred overnight at ambient temperature, filtered and evaporated down. The residue dissolved in ethyl acetate is washed with water and the organic phase dried over $MgSO_4$ and evaporated down.

Yield: 102.7 g of a compound Z5b (brown oil)

22.7 g of the compound Z5b are dissolved in 350 mL glacial acetic acid and at 60° C. combined batchwise with 17.4 g iron powder. After the addition ends the mixture is refluxed for 0.5 h, filtered hot and evaporated down. The residue is taken up in 200 mL dichloromethane/methanol (9:1) and washed with sodium chloride solution. The organic phase is suction filtered through kieselguhr, dried over $MgSO_4$, evaporated down and purified by column chromatography (eluant: ethyl acetate/cyclohexane 1:1).

Yield: 1.9 g of a compound Z5c (colourless crystals)

1.9 g of the compound Z5c are dissolved in 32 mL dimethylacetamide and while cooling with ice combined with 0.3 g (7 mmol) sodium hydride as a 60% dispersion in mineral oil. After 10 min 0.5 mL (7 mmol) methyl iodide are added and stirred for 3 h at ambient temperature. The reaction mixture is evaporated down and combined with water. The precipitate formed is suction filtered and washed with petroleum ether.

Yield: 1.6 g of a compound Z5d (colourless crystals)

14.0 g of the compound Z5d and 10.0 g (0.06 mol) 4-amino-3-methoxybenzoic acid are suspended in 200 mL dioxane and 80 mL water, combined with 10 mL concentrated hydrochloric acid and refluxed for 40 h. The precipitate formed on cooling is suction filtered and washed with water, dioxane and diethyl ether.

Yield: 13.9 g of a compound Z5 (colourless crystals)

To synthesise the compounds of Examples 88, 194, 229 and 89 of Table 2, first of all an intermediate compound Z6

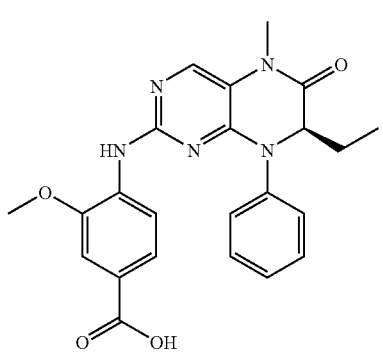

is prepared as described below.

6.0 g (0.06 mol) L-2-aminobutyric acid is placed in 80 mL 0.5 M sulphuric acid and at 0° C. combined with 5.5 g (0.08 mol) sodium nitrite in 15 mL water. The reaction mixture is stirred for 22 h at 0° C., combined with ammonium sulphate and filtered. The filtrate is extracted with diethyl ether and the combined organic dried over $MgSO_4$ and evaporated down.

Yield: 6.0 g of a compound Z6a (yellow oil)

200 mL methanol are combined successively with 65.0 mL (0.89 mol) thionyl chloride and 76.0 g of the compound Z6a in 50 mL methanol while cooling with ice. The resulting mixture is stirred for 1 h at 0° C. and 2 h at ambient temperature and then the methanol and remaining thionyl chloride are eliminated in vacuo at 0° C.

Yield: 40.0 g of a compound Z6b (yellow oil)

30.0 mL (0.17 mol) of trifluoromethanesulphonic acid anhydride are placed in 150 mL dichloromethane and while cooling with ice a solution of 20.0 g of the compound Z6b and 14.0 mL (0.17 mol) pyridine in 50 mL dichloromethane is added within one hour. The mixture is stirred for 2 h at ambient temperature, any salts formed are suction filtered and then washed with 100 mL water. The organic phase is dried over $MgSO_4$ and evaporated down.

Yield: 42.0 g of a compound Z6c (light yellow oil)

42.0 g of the compound Z6c in 200 mL dichloromethane is added dropwise within one hour to a solution of 15.5 mL (0.17 mol) of aniline and 24.0 mL (0.17 mol) of triethylamine in 400 mL dichloromethane while cooling with ice. The mixture is stirred for 1 h at ambient temperature and a further 2 h at 35° C. The reaction mixture is washed with water, dried over $MgSO_4$ and evaporated down. The residue remaining is purified by distillation (95-100° C., $1*10^{-3}$ mbar).

Yield: 14.0 of a compound Z6d (colourless oil)

14.0 g of the compound Z6d and 16.0 g (0.1 mol) potassium carbonate are suspended in 100 mL acetone and at 10° C. combined with 16.0 g (0.08 mol) of 2,4-dichloro-5-nitropyrimidine. The mixture is stirred for 4 h at 40° C., any salts formed are suction filtered and the filtrate evaporated down. The residue is taken up in 300 mL ethyl acetate and washed with water. The organic phase is dried over $MgSO_4$ and evaporated down.

Yield: 31.0 g of a compound Z6e (brown oil)

31.0 g of the compound Z6e are dissolved in 200 mL glacial acetic acid and at 60° C. combined batchwise with 10 g iron powder, during which time the temperature rose to 85° C. The mixture is stirred for a further hour at 60° C., filtered through kieselguhr and evaporated down. The residue is stirred with methanol.

Yield: 4.5 g of a compound Z6f (brown crystals)

At −20° C. 0.6 g (16 mmol) of sodium hydride as a 60% dispersion in mineral oil are added batchwise to a mixture of 4.5 g of the compound Z6f and 1.0 mL (16 mmol) methyl iodide in 100 mL dimethylacetamide. After 1 h the reaction mixture is combined with 50 mL water and evaporated down. The residue is stirred with 200 mL water, the precipitate is suction filtered and washed with petroleum ether.

Yield: 4.5 g of a compound Z6g (colourless crystals)

A suspension of 1.5 g of the compound Z6g and 1.4 g (8 mmol) of methyl 4-amino-3-methoxybenzoate in 30 mL toluene is combined with 0.4 g (0.6 mmol) of 2,2'-bis-(diphenylphosphino)-1,1'-binaphthyl, 0.23 g (0.3 mmol) of tris (dibenzylideneacetone)-dipalladium(0) and 7.0 g (21 mmol) of caesium carbonate and refluxed for 17 h. The reaction mixture is applied to silica gel and purified by column chromatography (eluant: dichloromethane/methanol 9:1).

Yield: 1.7 g of a compound Z6h (yellow crystals)

1.7 g of the compound Z6h are dissolved in 50 mL dioxane, combined with 15 mL of semiconcentrated hydrochloric acid and refluxed for 12 h. After cooling the precipitate formed is suction filtered.

Yield: 1.1 g of a compound Z6 (colourless solid)

To synthesise the compounds of Examples 26, 20, 32, 56, 101, 112 and 209 of Table 2, first of all an intermediate compound Z7

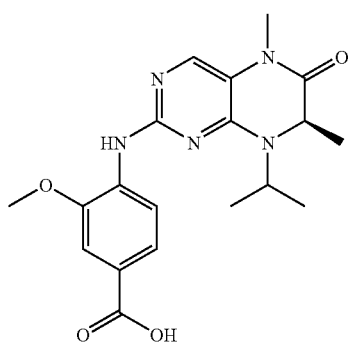

is prepared as described below.

50.0 g (0.36 mol) D-alanine methyl ester×HCl is suspended in 500 mL of dichloromethane and 35 mL of acetone and combined with 30.0 g (0.37 mol) of sodium acetate and 80.0 g (0.38 mol) of sodium triacetoxyborohydride. The mixture is stirred for 12 h and then poured onto 400 mL of 10% sodium hydrogen carbonate solution. The organic phase is dried over $Na_2SO_4$ and evaporated down.

Yield: 51.0 g of a compound Z7a (yellow oil)

A suspension of 51.0 g of the compound Z7a in 450 mL water is combined with 80.0 g (0.41 mol) of 2,4-dichloro-5-nitropyridine in 450 mL of diethyl ether. At −5° C. 100 mL of 10% potassium hydrogen carbonate solution are added dropwise. The reaction mixture is stirred for 3 h, the organic phase dried over $Na_2SO_4$ and evaporated down.

Yield: 74 g of a compound Z7b (yellow oil)

18.6 g of the compound Z7b are dissolved in 200 mL glacial acetic acid and at 60° C. combined batchwise with 20.0 g iron powder. The mixture is stirred for 2 h at 60° C. and then suction filtered through cellulose. The residue is dissolved in ethyl acetate and washed with water and concentrated ammonia. The organic phase is dried over Na$_2$SO$_4$ and evaporated down. The residue is crystallised from diethyl ether.

Yield: 9.8 g of a compound Z7c (colourless crystals)

17.0 g of the compound Z7c and 7 mL (0.1 mol) methyl iodide are dissolved in 200 mL dimethylacetamide and at −5° C. combined with 4.0 g (0.1 mol) of sodium hydride as a 60% dispersion in mineral oil. The reaction mixture is stirred for 30 min and then poured onto 300 mL ice water. The precipitate formed is suction filtered and stirred with petroleum ether.

Yield: 14.8 g of a compound Z7d (beige crystals)

0.9 g of the compound Z7d and 1.5 g (9 mmol) 4-amino-3-methoxybenzoic acid are heated to 210° C. for 30 min. After cooling the residue is stirred with ethyl acetate and the precipitate obtained is suction filtered.

Yield: 1.2 g of a compound Z7 (grey crystals)

The following acids can, for example, be prepared analogously to the methods of synthesis hereinbefore described.

Z8

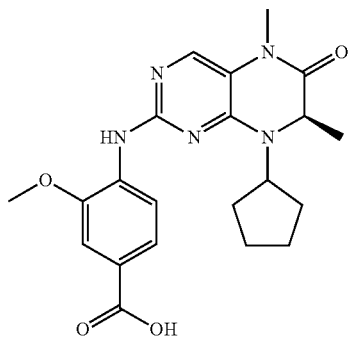

Z9

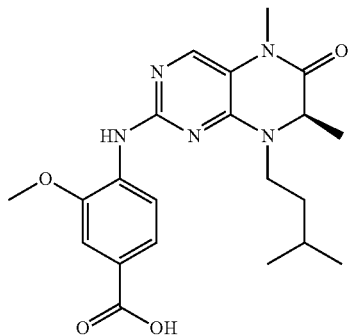

Z10

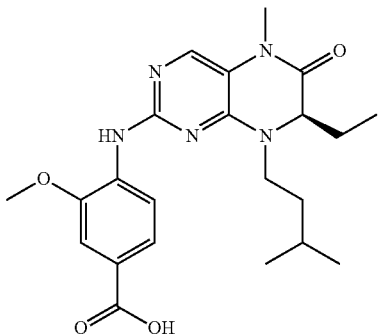

Z11

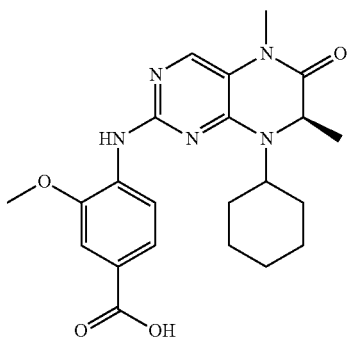

Synthesis of the Amino Components L-R5

The following amines, 1,1-dimethyl-2-dimethylamino-1-yl-ethylamine and
1,1-dimethyl-2-piperidin-1-yl-ethylamine,

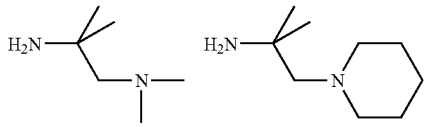

may be obtained as follows.

The compounds may be prepared according to the following references: (a) S. Schuetz et al. *Arzneimittel-Forschung* 1971, 21, 739-763, (b) V. M. Belikov et al. *Tetrahedron* 1970, 26, 1199-1216 and (c) E. B. Butler and McMillan *J. Amer. Chem. Soc.* 1950, 72, 2978.

Other amines can be prepared as follows, in a modified manner compared with the literature described above.

1,1-dimethyl-2-morpholin-1-yl-ethylamine

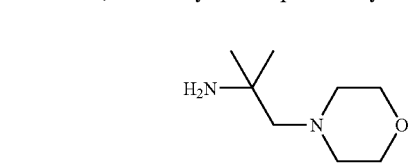

8.7 mL morpholine and 9.3 mL 2-nitropropane are prepared while cooling the reaction with ice, 7.5 mL formaldehyde (37%) and 4 mL of a 0.5 mol/L NaOH solution are slowly added dropwise (<10° C.). Then the mixture is stirred for 1 h at 25° C. and 1 h at 50° C. The solution is treated with water and ether and the aqueous phase is extracted 3× with ether. The combined organic phase is dried over NaSO4 and combined with HCl in dioxane (4 mol/l), the precipitate formed is suction filtered. Yield: 21.7 of white powder 5 g of the white powder are dissolved in 80 mL methanol and with the addition of 2 g RaNi treated with hydrogen at 35° C. and 50 psi for 40 minutes. This yields 3.6 g of 1,1-dimethyl-2-morpholin-1-yl-ethylamine.

The following amines can be prepared analogously.

1,1-dimethyl-N-methylpiperazin-1-yl-ethylamine

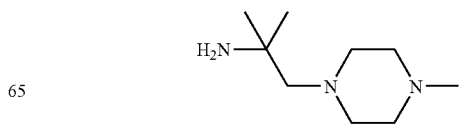

1,1-dimethyl-2-pyrrolidin-1-yl-ethylamine

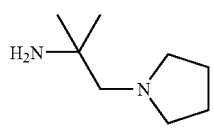

1,3-dimorpholin-2-amino-propane

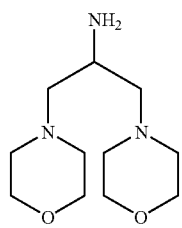

5 g of 1,3 Dimorpholine-2-nitropropane obtained from Messrs. Aldrich is dissolved in 80 mL methanol and treated with hydrogen for 5.5 h at 30° C. and 50 psi with the addition of 2 g RaNi. This yields 4.2 g of 1,3 dimorpholin-2-aminopropane.

4-Aminobenzylmorpholine

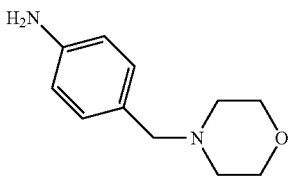

The preparation of this amine is described in the following reference:

S. Mitsuru et al. *J. Med. Chem.* 2000, 43, 2049-2063.

4-amino-1-tetrahydro-4H-pyran-4-yl-piperidine

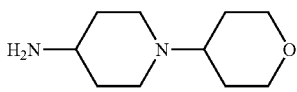

20 g (100 mmol) of 4-tert-butyloxycarbony-aminopiperidine are dissolved in 250 mL $CH_2Cl_2$ and stirred for 12 h at RT with 10 g (100 mmol) tetrahydro-4H-pyran-4-one and 42 g (200 mmol) $NaBH(OAc)_3$. Then water and potassium carbonate are added, the organic phase is separated off, dried and the solvent is eliminated in vacuo. The residue is dissolved in 200 mL $CH_2Cl_2$ and stirred for 12 h at RT with 100 mL trifluoroacetic acid. The solvent is eliminated in vacuo, the residue taken up with $CHCl_3$ and evaporated down again, then taken up in acetone and the hydrochloride is precipitated with ethereal HCl. Yield: 14.3 g (56%).

Cis- and trans-4-morpholino-cyclohexylamine

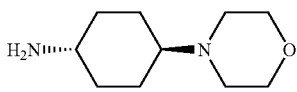

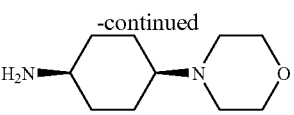

Dibenzyl-4-morpholino-cyclohexylamine 3.9 g (30 mmol) of 4-dibenzylcyclohexanone are dissolved in 100 mL of $CH_2Cl_2$ and stirred for 12 h at RT with 3.9 g (45 mmol) of morpholine and 9.5 g (45 mmol) $NaBH(OAc)_3$. Then water and potassium carbonate are added, the organic phase is separated off, dried and the solvent is eliminated in vacuo. The residue is purified through a silica gel column (about 20 mL silica gel; about 500 mL of ethyl acetate 90/methanol 10+1% concentrated ammonia). The appropriate fractions are evaporated down in vacuo. Yield: 6.6 g (60%) of cis-isomer and 2 g (18%) of trans-isomer.

Alternatively, the trans-dibenzyl-4-morpholino-cyclohexylamine may be prepared by the following method:

33 g (112 mmol) of 4-dibenzylcyclohexanone are dissolved in 300 mL MeOH, combined with 17.4 g (250 mmol) of hydroxylamine hydrochloride and stirred for 4 h at 60° C. The solvent is evaporated down in vacuo, combined with 500 mL water and 50 g potassium carbonate and extracted twice with 300 mL of dichloromethane. The organic phase is dried, evaporated down in vacuo, the residue is crystallised from petroleum ether, dissolved in 1.5 L of EtOH and heated to 70° C. 166 g of sodium are added batchwise and the mixture is refluxed until the sodium dissolves. The solvent is eliminated in vacuo, the residue combined with 100 mL water and extracted twice with 400 mL of ether. The organic phase is washed with water, dried, evaporated down in vacuo and the trans isomer is isolated using a column (about 1.5 L silica gel; about 2 L of ethyl acetate 80/methanol 20+2% concentrated ammonia). Yield: 12.6 g (41.2%).

6.8 g (23 mmol) of trans-1-amino-4-dibenzylaminocyclohexane is dissolved in 90 mL of DMF and stirred for 8 h at 100° C. with 5 mL (42 mmol) of 2,2'-dichloroethyl ether and 5 g of potassium carbonate. After cooling 30 mL of water is added, the precipitated crystals are suction filtered and purified through a short column (about 20 mL silica gel, about 100 mL ethyl acetate). The residue is crystallised from methanol and concentrated HCl as the dihydrochloride. Yield: 7.3 g (72.4%).

Trans-4-morpholino-cyclohexylamine 7.2 g (16.4 mmol) of trans-dibenzyl-4-morpholino-cyclohexylamine are dissolved in 100 mL of MeOH and hydrogenated on 1.4 g of Pd/C (10%) at 30-50° C. The solvent is eliminated in vacuo and the residue is crystallised from ethanol and concentrated HCl.

Yield: 3.9 g (93%).

The cis isomer may be prepared analogously.

Cis- and trans-4-piperidino-cyclohexylamine

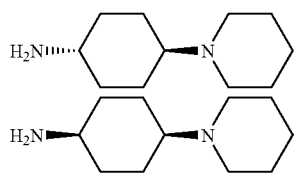

Trans-dibenzyl-4-piperidino-cyclohexylamine 2.0 g (6.8 mmol) of trans-1amino-4-dibenzylaminocyclohexane (see Example 2) is dissolved in 50 mL DMF and stirred for 48 h at RT with 1.6 g (7 mmol) of 1,5-dibromopentane and 2 g of potassium carbonate. The mixture is cooled, combined with water, extracted twice with 100 mL of dichloromethane, dried and the solvent is eliminated in vacuo. The residue is purified over a column (about 100 mL silica gel, about 500 mL ethyl acetate 80/methanol 20+1% concentrated ammonia). The desired fractions are evaporated down in vacuo and crystallised from petroleum ether. Yield: 1.2 g (49%).

Trans-4-piperidino-cyclohexylamine 1.7 g (4.8 mmol) of trans-dibenzyl-4-piperidino-cyclohexylamine are dissolved in 35 mL MeOH and hydrogenated on 350 mg of Pd/C (10%) at 20° C. The solvent is eliminated in vacuo and the residue crystallised from ethanol and concentrated HCl.
Yield: 1.1 g (78%).
The cis isomer may be prepared analogously.

Cis- and trans-4-(4-phenyl-piperazin-1-yl)-cyclohexylamine

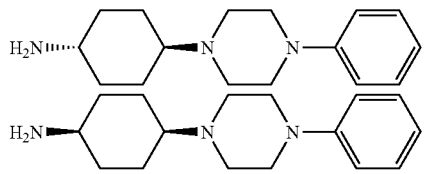

4.1 g (25.3 mmol) of 4-dibenzylcyclohexanone is dissolved in 50 mL of dichloromethane and stirred for 12 h at RT with 7.4 g (25.3 mmol) of N-phenylpyperazine and 7.4 g (35 mmol) of NaBH(OAc)$_3$. Then water and potassium carbonate are added, the organic phase is separated off, dried and the solvent is eliminated in vacuo. The residue is purified over a silica gel column (ethyl acetate 80/methanol 20+0.5% concentrated ammonia). Yield: 1.7 g (15.8%) of cis-isomer and 0.27 (2.5%) of trans-isomer.

Trans-4-(4-phenyl-piperazin-1-yl)-cyclohexylamine 270 mg (0.61 mmol) of trans-dibenzyl-[4-(4-phenyl-piperazin-1-yl)-cyclohexyl]-amine are dissolved in 5 mL MeOH and hydrogenated on 40 mg of Pd/C (10%) at 20-30° C. The solvent is eliminated in vacuo and the residue crystallised from ethanol and concentrated HCl. Yield: 110 mg (69%).
The cis isomer may be prepared analogously.

Cis- and trans-4-(4-cyclopropylmethyl-piperazin-1-yl)-cyclohexylamine

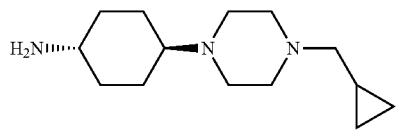

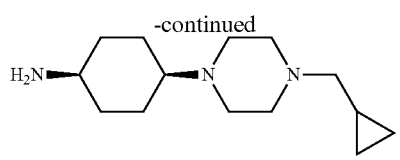

9.8 g (33.4 mmol) of 4-dibenzylcyclohexanone is dissolved in 100 mL dichloromethane and stirred for 12 h at RT with 5.6 g (40 mmol) of N-cyclopropylmethylpiperazine and 8.5 g (40 mmol) of NaBH(OAc)$_3$. Then water and potassium carbonate are added, the organic phase is separated off, dried and the solvent is eliminated in vacuo. The residue is purified over a silica gel column (about 50 mL silica gel, about 3 L ethyl acetate 95/methanol 5+0.25% concentrated ammonia. The appropriate fractions are evaporated down in vacuo. The faster eluting cis compound crystallised from ethyl acetate. The trans-compound is crystallised from ethanol+ concentrated HCl. Yield: 8.5 g (61%) cis-isomer and 2.2 (13%) trans-isomer.

cis-4-(4-cyclopropylmethyl-piperazin-1-yl)-cyclohexylamine 8.5 g (20 mmol) of cis-dibenzyl-[4-(4-cyclopropylmethyl-piperazin-1-yl)-cyclohexyl]-amine are dissolved in 170 mL MeOH and hydrogenated on 1.7 g Pd/C (10%) at 30-50° C. The solvent is eliminated in vacuo and the residue is crystallised from ethanol and concentrated HCl. Yield: 4.4 g (91%).
The trans-isomer may be prepared analogously.

SYNTHESIS OF THE EXAMPLES

Example 152

0.15 g of the compound Z10, 0.14 g TBTU, 0.13 mL DIPEA are dissolved in dichloromethane and stirred for 20 minutes at 25° C. Then 90 µL 1-(3-aminopropyl)-4-methylpiperazine is added and stirred for a further 2 hours at 25° C. The solution is then diluted with dichloromethane and extracted with water. The product is precipitated by the addition of petroleum ether, ether and ethyl acetate to the organic phase. Yield: 0.16 g of beige solid.

Example 164

0.10 g of the compound Z10, 0.1 g TBTU, 0.08 mL DIPEA are dissolved in 4 mL dichloromethane and stirred for 20 minutes at 25° C. Then 44 µL dimethylaminopropylamine are added and stirred for a further 2 hours at 25° C. The solution is then diluted with dichloromethane and extracted with water. The product is precipitated by the addition of petroleum ether, ether and acetone to the organic phase.
Yield: 0.08 g yellow solid.

Example 242

0.15 g of the compound Z10, 0.14 g TBTU, 0.13 mL DIPEA are dissolved in 5 mL dichloromethane and stirred for 20 minutes at 25° C. Then 75 µL 1-(2-aminoethyl)piperidine are added and stirred for a further 2 hours at 25° C. The solution is then diluted with dichloromethane and extracted with water. The product is precipitated by the addition of petroleum ether, ether and ethyl acetate to the organic phase.
Yield: 0.14 g yellow solid.

Example 188

0.1 g of the compound Z2, 0.09 g TBTU, 0.05 mL DIPEA are dissolved in 15 mL dichloromethane and stirred for 20 minutes at 25° C. Then 33 mg 1-methyl-4-aminopiperidin are added and the mixture is stirred for a further 3 hours at 25° C. The solution is extracted with 20 mL water, then evaporated down in vacuo. The product is crystallised using ether. Yield: 0.047 g of white crystals.

Example 203

0.1 g of the compound Z2, 0.09 g TBTU, 0.5 mL DIPEA are dissolved in 15 mL dichloromethane and stirred for 30 minutes at 25° C. Then 50 mg 4-amino-1-benzylpiperidin are added and the mixture is stirred for a further 3 hours at 25° C. The solution is extracted with 20 mL water, then evaporated down in vacuo. Then the residue is chromatographed over silica gel and the isolated product is crystallised with ether. Yield: 0.015 g of white crystals.

Example 94

0.17 g of the compound Z1, 0.19 g TBTU, 0.11 mL DIPEA are dissolved in 50 mL dichloromethane and stirred for 30 minutes at 25° C. Then 63 mg of 1-methyl-4-aminopiperidine are added and the mixture is stirred for a further 17 hours at 25° C. 50 mL of water and 1 g of potassium carbonate are added to the solution and the organic phase is separated off using a phase separation cartridge, then evaporated down in vacuo. Then the product is purified by silica gel chromatography and the purified product is crystallised with ether. Yield: 0.1 g of white crystals.

Example 95

0.17 g of the compound Z1, 0.19 g TBTU, 0.11 mL DIPEA are dissolved in 50 mL dichloromethane and stirred for 30 minutes at 25° C. Then 77 mg of exo-3-β-amino-tropane are added and the mixture is stirred for a further 17 hours at 25° C. 50 mL of water and 1 g of potassium carbonate are added to the solution and the organic phase is separated off using a phase separation cartridge, then evaporated down in vacuo. Then the product is purified by silica gel chromatography and the purified product is crystallised with ether. Yield: 0.03 g of white crystals.

Example 46

0.15 g of the compound Z3, 0.12 g TBTU, 0.12 mL DIPEA are dissolved in 5 mL dichloromethane and stirred for 30 minutes at 25° C. Then 50 mg 1-methyl-4-aminopiperidin are added and the mixture is stirred for a further 2.5 hours at 25° C. The solution is then extracted with water and then evaporated down. The residue is dissolved in warm ethyl acetate and crystallised from ether and petroleum ether. Yield: 0.025 g of white crystals.

Example 80

0.2 g of the compound Z8, 0.2 g of TBTU, 0.1 mL of DIPEA are dissolved in 10 mL dichloromethane and stirred for 30 minutes at 25° C. Then 100 mg of 1-methyl-4-aminopiperidine are added and the mixture is stirred for a further 17 hours at 25° C. The solution is then extracted with a dilute potassium carbonate solution and evaporated down. The residue is crystallised using ether. Yield: 0.12 g of white crystals.

Example 190

0.2 g of compound Z8, 0.2 g of TBTU, 0.3 mL of DIPEA are dissolved in 5 mL dichloromethane and stirred for 1 h at 25° C. Then 0.13 g of 4-amino-1-benzylpiperidine are added and the mixture is stirred for a further hour at 25° C. The solution is then diluted with 10 mL methylene chloride and extracted with 20 mL water. Then the product is purified over silica gel and crystallised from ethyl acetate and ether. Yield: 0.23 g of the compound Z8.

0.23 g of the benzylamine Z8 are dissolved in 10 mL methanol, combined with 50 mg of Pd/C and hydrogenated under 3 bar for 3 h at 25° C. By adding petroleum ether and ethyl acetate white crystals are produced. These are chromatographed over silica gel and crystallised from ethyl acetate and ether. Yield: 0.075 g of white crystals.

Example 196

0.1 g of compound Z10, 0.09 g of TBTU, 0.3 mL of DIPEA are dissolved in 4 mL of dichloromethane and stirred for 20 minutes at 25° C. Then 67 mg xx amine is added and stirred for a further 2 hours at 25° C. The solution is then diluted with dichloromethane and extracted with water. It is then chromatographed over silica gel and the residue is dissolved in acetone, combined with ethereal HCl and the precipitate formed is isolated.

Yield: 0.09 g light yellow solid.

Example 166

0.1 g of the compound Z10, 0.11 g of TBTU, 0.14 mL of DIPEA are dissolved in 2 mL dimethylformamide and stirred for 3 h at 50° C. Then 55 mg of 4-morpholinomethylphenylamine is added. The reaction mixture is then cooled to ambient temperature within 17 h. Then the dimethylformamide is eliminated in vacuo, the residue is taken up in dichloromethane and extracted with water. It is then chromatographed over silica gel and the product crystallised from ethyl acetate and ether. Yield: 0.06 g yellowish crystals.

Example 81

0.2 g of the compound Z4, 0.2 g of TBTU, 0.1 mL of DIPEA are dissolved in 10 mL dichloromethane and stirred for 30 minutes at 25° C. Then 0.1 g of 1-methyl-4-aminopiperidine are added and the mixture is stirred for a further 17 hours at 25° C. The solution is then extracted with aqueous potassium carbonate solution and then evaporated down. The product is crystallised using ether. Yield: 0.16 g of white crystals.

Example 162

0.1 g of the compound Z5, 0.07 g of TBTU, 0.15 mL of DIPEA are dissolved in 5 mL dichloromethane and stirred for 20 minutes at 25° C. Then 0.04 g 1-methyl-4-aminopiperidine are added and the mixture is stirred for a further 2 hours at 25° C. The solution is then diluted with 15 mL dichloromethane and extracted with 20 mL water. The residue is dissolved in MeOH and acetone, combined with 1 mL ethereal HCl and evaporated down. A crystalline product is produced using ether, ethyl acetate and a little MeOH. Yield: 0.1 g of white crystals.

Example 88

0.1 g of the compound Z6, 0.12 g of TBTU, 0.12 mL of DIPEA are in 10 mL dichloromethane dissolved and stirred for 30 minutes at 25° C. Then 0.04 g of 1-methyl-4-aminopiperidine are added and the mixture is stirred for a further 2 hours at 25° C. The solution is then diluted with 10 mL dichloromethane and extracted with 10 mL water. A crystalline product is produced using ether, ethyl acetate and petroleum ether. Yield: 0.6 g of white crystals.

Example 89

0.1 g of the compound Z6, 0.08 g of TBTU, 0.08 mL of DIPEA are dissolved in 10 mL dichloromethane and stirred for 30 minutes at 25° C. Then 37 µL g N,N-dimethylneopentanediamine are added and the mixture is stirred for a further 2 hours at 25° C. The solution is then diluted with 10 mL dichloromethane and extracted with 10 mL water. The product is then chromatographed over silica gel and crystallised from ethyl acetate, ether and petroleum ether. Yield: 0.005 g of white crystals.

Example 26

0.15 g of the compound Z7, 0.16 g of TBTU, 1 mL of DIPEA are dissolved in 5 mL dichloromethane and stirred for 30 minutes at 25° C. Then 0.1 g 4-morpholinocyclohexylamine are added and the mixture is stirred for a further 17 hours at 25° C. The residue is then combined with 10 mL of 10% potassium carbonate solution, the precipitate is isolated and washed with water. It is then dissolved in dichloromethane and evaporated down again. The product is crystallised from ethyl acetate. Yield: 0.1 g of white crystals.

Example 9

150 mg of the compound Z9 and 93 mg of amine are dissolved in 5 mL dichloromethane and stirred with 160 mg of TBTU and 1 mL of DIPEA for 12 h at RT. The solvent is eliminated in vacuo, the residue is combined with 10 mL of 10% potassium carbonate solution. The precipitate is suction filtered, washed with water, taken up in dichloromethane, dried and the solvent eliminated in vacuo. The residue is crystallised from ethyl acetate. Yield: 82.0 mg.

Example 16

150 mg of the compound Z8 and 73 mg of trans-4-piperidino-cyclohexylamine are dissolved in 5 mL dichloromethane and stirred with 160 mg (0.50 mmol) of TBTU and 1 mL of DIPEA for 12 h at RT. The solvent is eliminated in vacuo, the residue is combined with 10 mL of 10% potassium carbonate solution. The precipitate is suction filtered, washed with water, taken up in dichloromethane, dried and the solvent eliminated in vacuo. The residue is crystallised from ethyl acetate. Yield: 87.0 mg.

Example 37

100 mg of the compound Z9 and 42 mg of 3-amino-1-ethyl-pyrrolidine are dissolved in 10 mL dichloromethane and stirred with 90 mg of TBTU and 0.5 mL of DIPEA for 12 h at RT. The solvent is eliminated in vacuo, the residue is combined with 10 mL of 10% potassium carbonate solution. The precipitate is suction filtered, washed with water, taken up in dichloromethane, dried and the solvent is eliminated in vacuo. The residue is crystallised from ethyl acetate/petroleum ether. Yield: 24.0 mg.

Example 120

100 mg of the compound Z11 and 73 mg of 4-amino-1tetrahydro-4H-pyran-4-yl-piperidine are dissolved in 10 mL dichloromethane and stirred with 90 mg of TBTU and 0.5 mL of DIPEA for 1 h at RT. The solvent is eliminated in vacuo, the residue is combined with 10 mL of 10% potassium carbonate solution. The precipitate is suction filtered, washed with water, taken up in dichloromethane, dried and the solvent is eliminated in vacuo. The residue is crystallised from ethyl acetate/petroleum ether.
Yield: 89 mg.

Example 212

150 mg of the compound Z5 and 150 mg of trans-4-(4-cyclopropylmethyl-piperazin-1-yl)-cyclohexylamine (as the hydrochloride) are dissolved in 5 mL of dichloromethane and stirred with 160 mg of TBTU and 2 mL of DIPEA for 2 h at RT. The solvent is eliminated in vacuo, the residue is combined with 10 mL of 10% potassium carbonate solution. The precipitate is suction filtered, washed with water, taken up in dichloromethane, dried and the solvent eliminated in vacuo. The residue is purified over a column (20 mL silica gel, 300 mL ethyl acetate 90/methanol 10+2% concentrated ammonia). The appropriate fractions are evaporated down in vacuo and crystallised from ethyl acetate. Yield: 140 mg.

Example 232

390 mg of the compound Z11 and 240 mg of trans-4-(4-tbutyloxycarbonyl-piperazin-1-yl)-cyclohexylamine are dissolved in 2.5 mL of NMP and stirred with 482 mg of TBTU and 1 mL triethylamine for 2 h at RT. Then 100 mL of water and 200 mg of potassium carbonate are added, the precipitate is suction filtered, washed with water and purified through a silica gel column. The appropriate fractions are evaporated down in vacuo, dissolved in 2 mL dichloromethane, combined with 2 mL of trifluoroacetic acid and stirred for 2 h at RT, combined with another 100 mL of water and 200 mg potassium carbonate and the precipitate is suction filtered and washed with water. Then the precipitate is purified through a silica gel column. The appropriate fractions are evaporated down in vacuo and the residue is crystallised from ethanol and concentrated hydrochloric acid. Yield: 95 mg.

Example 213

60 mg of the compound of Example 232 is dissolved in 10 mL ethyl acetate and stirred with 1 mL of acetic anhydride and 1 mL of triethylamine for 30 min. at RT. The solvent is eliminated in vacuo, the residue combined with water and ammonia, the crystals precipitated are suction filtered and washed with water and a little cold acetone.
Yield: 40 mg.

Example 218

1.2 g of the compound Z9 and 0.5 g of 1,4-dioxaspiro[4.5]dec-8-ylamine were dissolved in 20 mL dichloromethane and stirred with 1.28 g of TBTU and 4 mL of triethylamine for 12 h at RT. Then 50 mL of water and 0.5 g of potassium carbonate are added, the organic phase is separated off, dried and evaporated down in vacuo. The residue is crystallised from ethyl acetate, combined with 25 mL of 1N hydrochloric acid and 20 mL of methanol and stirred for 30 min at 50° C. The methanol is eliminated in vacuo, the precipitate is suction filtered, washed with water and dried. The residue is taken up in 20 mL dichloromethane, stirred with 0.5 g of thiomorpholine and 0.5 g of NaBH(OAc)$_3$ for 12 h at RT. Then water and potassium carbonate are added, the organic phase is separated off, dried and the solvent is eliminated in vacuo. The residue is purified over a silica gel column. The appropriate fractions are evaporated down in vacuo and the hydrochloride is precipitated with ethereal HCl.

Yield: 86 mg of trans-isomer; amorphous powder.

Example 187

200 mg of the compound Z3 in 5 mL dichloromethane is combined with 0.1 mL of diisopropylethylamine and 180 mg of TBTU and stirred for 30 min. Then 191 mg of 4-(4-methyl-piperazin-1-yl)-phenylamine are added and the mixture is stirred overnight. The reaction mixture is combined with water and the aqueous phase extracted with dichloromethane. The combined organic phases are dried over $Na_2SO_4$ and evaporated down. The residue is purified by column chromatography (eluant: dichloromethane/methanol 100:7).

Yield: 128 mg (light yellow crystals).

The compounds of Formula (I) listed in Table 2, inter alia, are obtained analogously to the procedure described hereinbefore. The abbreviations $X_1$, $X_2$, $X_3$, $X_4$ and $X_5$ used in Table 2 in each case denote a link to a position in the general Formula shown under Table 2 instead of the corresponding groups $R^1$, $R^2$, $R^3$, $R^4$ and L-$R^5$.

TABLE 2

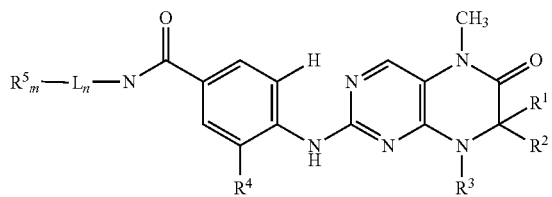

| Example | $R^1$ | $R^2$ | Config. $R^1$ or $R^2$ | $R^3$ | $R^4$ | $L_n$—$R^5_m$ |
|---|---|---|---|---|---|---|
| 1 | H | $X_2$—CH₃ | R | $X_3$—CH₂CH(CH₃)CH₃ | $X_4$—O—CH₃ | $X_5$-(2,2,6,6-tetramethyl-1-methyl-piperidin-4-yl) |
| 2 | H | $X_2$—CH₃ | R | $X_3$—CH₂CH(CH₃)CH₃ | $X_4$—O—CH₃ | $X_5$-(1-isopropyl-piperidin-4-yl) |
| 3 | H | $X_2$—CH₃ | R | $X_3$—CH₂CH(CH₃)CH₃ | H | $X_5$-(2,2,6,6-tetramethyl-1-methyl-piperidin-4-yl) |
| 4 | H | $X_2$—CH₃ | R | $X_3$—CH₂CH(CH₃)CH₃ | H | $X_5$-(1-ethyl-piperidin-4-yl) |
| 5 | H | $X_2$—CH₃ | R | $X_3$—CH₂C(CH₃)₂CH₃ | $X_4$—O—CH₃ | $X_5$-(2,2,6,6-tetramethyl-1-methyl-piperidin-4-yl) |

TABLE 2-continued

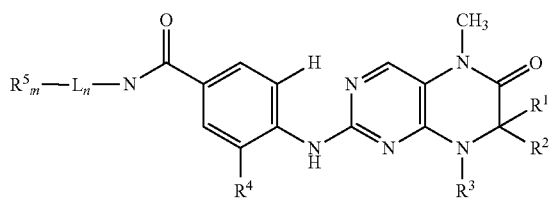

| Example | R¹ | R² | Config. R¹ or R² | R³ | R⁴ | $L_n-R^5_m$ |
|---|---|---|---|---|---|---|
| 6 | H | X₂—CH₃ | R | X₃—C(CH₃)₃ (neopentyl) | X₄—O—CH₃ | X₅—piperidine-N-ethyl |
| 7 | H | X₂—CH₃ | R | X₃—C(CH₃)₃ (neopentyl) | X₄—O—CH₃ | X₅—piperidine-N-isopropyl |
| 8 | H | X₂—CH₃ | R | X₃—C(CH₃)₃ (neopentyl) | H | X₅—2,2,6,6-tetramethyl-N-methylpiperidine |
| 9 | H | X₂—CH₃ | R | X₃—CH₂CH(CH₃)₂ (isobutyl) | X₄—O—CH₃ | X₅—cyclohexyl-morpholine (trans) |
| 10 | H | X₂—CH₃ | R | X₃—C(CH₃)₃ (neopentyl) | H | X₅—piperidine-N-benzyl |
| 11 | H | X₂—CH₃ | R | X₃—C(CH₃)₃ (neopentyl) | H | X₅—piperidine-N-ethyl |

US 8,058,270 B2
47 48
TABLE 2-continued
| Example | R¹ | R² | Config. R¹ or R² | R³ | R⁴ | Lₙ—R⁵ₘ |
|---|---|---|---|---|---|---|
| 12 | H | X₂—CH₃ | R | X₃—CH₂C(CH₃)₃ | H | X₅-(4-isopropylpiperidin-1-yl) |
| 13 | H | X₂—CH₃ | R | X₃-cyclopentyl | CH₃O—X₄ | X₅-(4-isopropylpiperidin-1-yl) |
| 14 | H | X₂—CH₃ | R | X₃-cyclopentyl | H | X₅-(4-isopropylpiperidin-1-yl) |
| 15 | H | X₂—CH₃ | R | X₃-cyclopentyl | X₄—OCH₃ | X₅-trans-(4-pyrrolidin-1-yl-cyclohexyl) |
| 16 | H | X₂—CH₃ | R | X₃-cyclopentyl | X₄—OCH₃ | X₅-trans-(4-piperidin-1-yl-cyclohexyl) |

TABLE 2-continued

| Example | R¹ | R² | Config. R¹ or R² | R³ | R⁴ | Lₙ—R⁵ₘ |
|---|---|---|---|---|---|---|
| 17 | H | X₂▰CH₃ | R | X₃-cyclopentyl | CH₃-O-X₄ | X₅-(1-ethylpiperidin-4-yl) |
| 18 | H | X₂▰CH₃ | R | X₃-cyclopentyl | H | X₅-(1-ethylpiperidin-4-yl) |
| 19 | H | X₂-CH₂CH₃ | R | X₃-cyclopentyl | X₄-O-CH₃ | X₅-(4-(pyrrolidin-1-yl)cyclohexyl) |
| 20 | H | X₂▰CH₃ | R | X₃-isopropyl | CH₃-O-X₄ | X₅-(1-ethylpiperidin-4-yl) |
| 21 | H | X₂-CH₂CH₃ | R | X₃-cyclopentyl | CH₃-O-X₄ | X₅-(1,2,2,6,6-pentamethylpiperidin-4-yl) |

TABLE 2-continued

| Example | R¹ | R² | Config. R¹ or R² | R³ | R⁴ | Lₙ—R⁵ₘ |
|---|---|---|---|---|---|---|
| 22 | H | X₂—CH₃ (wedge) | R | X₃-cyclopentyl | CH₃-O-X₄ | X₅-(4-piperidinyl), N-ethyl |
| 23 | H | X₂—CH₃ (wedge) | R | X₃-cyclopentyl | CH₃-O-X₄ | X₅-(4-piperidinyl), N-isopropyl |
| 24 | H | X₂—CH₃ (dashed) | R | X₃-cyclopentyl | X₄-O-CH₃ | X₅-(trans-4-cyclohexyl)-morpholine |
| 25 | H | X₂—CH₃ (dashed) | R | X₃-cyclopentyl | X₄-O-CH₃ | X₅-(trans-4-cyclohexyl)-piperidine |
| 26 | H | X₂—CH₃ (dashed) | R | X₃-CH(CH₃)₂ | X₄-O-CH₃ | X₅-(trans-4-cyclohexyl)-morpholine |

TABLE 2-continued

| Example | R¹ | R² | Config. R¹ or R² | R³ | R⁴ | Lₙ—R⁵ₘ |
|---|---|---|---|---|---|---|
| 27 | H | X₂–CH₂–CH₃ | R | X₃–CH(CH₃)₂ | X₄–O–CH₃ | X₅–cyclohexyl–morpholine |
| 28 | H | X₂–CH₂–CH₃ | R | X₃–CH(CH₃)₂ | X₄–O–CH₃ | X₅–cyclohexyl–morpholine |
| 29 | H | X₂–CH₃ | R | X₃–CH₂CH(CH₃)₂ | X₄–O–CH₃ | X₅–cyclohexyl–piperidine |
| 30 | H | X₂–CH₃ | R | X₃–cyclopentyl | CH₃–O–X₄ | X₅–2,2,6,6-tetramethyl-N-methylpiperidine |
| 31 | H | X₂–CH₃ | R | X₃–cyclopentyl | H | X₅–2,2,6,6-tetramethyl-N-methylpiperidine |

TABLE 2-continued
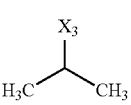
| Example | R¹ | R² | Config. R¹ or R² | R³ | R⁴ | Lₙ—R⁵ₘ |
|---|---|---|---|---|---|---|
| 32 | H | X₂—CH₃ | R | X₃ / H₃C-CH-CH₃ | CH₃-O-X₄ | 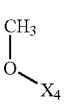 |
| 33 | H | X₂—CH₃ | R | X₃ / H₃C-CH-CH₃ | H | 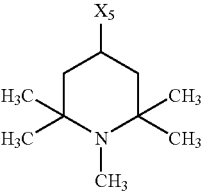 |
| 34 | H | X₂—CH₃ | R | X₃-CH₂-CH(CH₃)-CH₃ | X₄-O-CH₃ | 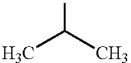 |
| 35 | H | X₂—CH₃ | R | X₃-CH₂-CH(CH₃)-CH₃ | X₄-O-CH₃ | 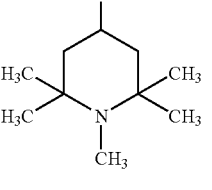 |
| 36 | H | X₂—CH₃ | R | X₃-cyclopentyl | X₄-O-CH₃ | 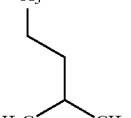 |

TABLE 2-continued

| Example | R¹ | R² | Config. R¹ or R² | R³ | R⁴ | Lₙ—R⁵ₘ |
|---|---|---|---|---|---|---|
| 37 | H | X₂—CH₃ | R | X₃—CH(CH₃)CH₂— (isobutyl with X₃) | X₄—O—CH₃ | X₃-pyrrolidine-N-ethyl |
| 38 | H | X₂—CH₃ | R | X₃—CH₂CH(CH₃)₂ | X₄—O—CH₃ | X₅-cyclohexyl-morpholine |
| 39 | H | X₂—CH₃ | R | X₃—CH₂CH(CH₃)₂ | H | X₅-pyrrolidine-N-ethyl |
| 40 | H | X₂—CH₃ | R | X₃-cyclopentyl | X₄—O—CH₃ | X₅-cyclohexyl-morpholine |
| 41 | H | X₂—CH₃ | R | X₃-phenyl | CH₃—O—X₄ | X₅-N-methylpiperidine |

TABLE 2-continued

| Example | R¹ | R² | Config. R¹ or R² | R³ | R⁴ | Lₙ—R⁵ₘ |
|---|---|---|---|---|---|---|
| 42 | H | X₂—CH₃ | R | X₃—CH(CH₃)—CH₂—(with H₃C, CH₃) | CH₃—O—X₄ | X₅-N-methyl azabicyclic |
| 43 | X₁—CH₃ | X₂—CH₃ |  | X₃—CH(CH₃)—CH₂—(with H₃C, CH₃) | H₃C—O—X₄ | X₅-N-methyl azabicyclic |
| 44 | H | X₂—CH₃ | R | X₃-cyclopentyl | H | X₅-N-methyl piperidine |
| 45 | H | X₂—CH₃ | R | X₃-cyclopentyl | H₃C—O—X₄ | X₅-N-methyl azabicyclic |
| 46 | H | X₂—CH₃ | R | X₃-cyclopentyl | H₃C—O—X₄ | X₅-N-methyl piperidine |
| 47 | H | X₂—CH₃ | R | X₃-cyclopentyl | H | X₅-N-methyl azabicyclic |

TABLE 2-continued

| Example | R¹ | R² | Config. R¹ or R² | R³ | R⁴ | Lₙ—R⁵ₘ |
|---|---|---|---|---|---|---|
| 48 | H | X₂—CH₃ | R | X₃-phenyl | H | X₅-(1-methylpiperidin-4-yl) |
| 49 | H | X₂—CH₃ | R | X₃-cyclopentyl | CH₃—O—X₄ | X₅-CH₂C(CH₃)₂CH₂-pyrrolidin-1-yl |
| 50 | H | X₂—CH₃ | R | X₃-CH₂C(CH₃)₃ | X₄—O—CH₃ | X₅-CH₂C(CH₃)₂CH₂-pyrrolidin-1-yl |
| 51 | H | X₂-cyclopropyl | R | X₃-cyclopentyl | CH₃—O—X₄ | X₅-CH₂C(CH₃)₂CH₂-N(CH₃)₂ |
| 52 | H | X₂—CH₃ | R | X₃-CH₂C(CH₃)₃ | CH₃—O—X₄ | X₅-CH₂C(CH₃)₂CH₂-N(CH₃)₂ |
| 53 | X₁—CH₃ | X₂—CH₃ |  | X₃-CH₂CH₂CH(CH₃)₂ | CH₃—O—X₄ | X₅-CH₂C(CH₃)₂CH₂-N(CH₃)₂ |

TABLE 2-continued

| Example | R¹ | R² | Config. R¹ or R² | R³ | R⁴ | Lₙ—R⁵ₘ |
|---|---|---|---|---|---|---|
| 54 | H | X₂—CH₃ (wedge) | R | X₃-CH(CH₃)₂ | CH₃-O-X₄ | H₃C-C(CH₃)(X₅)-CH₂-pyrrolidinyl |
| 55 | H | X₂—CH₃ (wedge) | R | X₃-cyclopentyl | CH₃-O-X₄ | H₃C-C(CH₃)(X₅)-CH₂-pyrrolidinyl |
| 56 | H | X₂—CH₃ (dash) | R | X₃-CH(CH₃)₂ | CH₃-O-X₄ | H₃C-C(CH₃)(X₅)-CH₂-pyrrolidinyl |
| 57 | H | X₂—CH₃ (wedge) | R | X₃-CH(CH₃)₂ | CH₃-O-X₄ | X₅-C(CH₃)(CH₂CH₃)-CH₂-N(CH₃)₂ |
| 58 | H | X₂—CH₃ (wedge) | R | X₃-cyclopentyl | CH₃-O-X₄ | X₅-C(CH₃)(CH₂CH₃)-CH₂-N(CH₃)₂ |
| 59 | H | X₂—CH₃ (dash) | R | X₃-phenyl | H₃C-O-X₄ | X₅-(1-methylpiperidin-4-yl) |

TABLE 2-continued

| Example | R¹ | R² | Config. R¹ or R² | R³ | R⁴ | Lₙ—R⁵ₘ |
|---|---|---|---|---|---|---|
| 60 | H | X₂—CH₃ | R | cyclopentyl-X₃ | CH₃-O-X₄ | X₅-CH₂-C(CH₃)₂-CH₂-N(CH₃)₂ |
| 61 | X₁—CH₃ | X₂—CH₃ | | X₃-CH₂-CH(CH₃)-CH₃ | H₃C-O-X₄ | X₅-(1-methylpiperidin-4-yl) |
| 62 | H | X₂—CH₃ | R | cyclopentyl-X₃ | CH₃-O-X₄ | (H₃C-CH₂)₂N-CH₂-CH₂-X₅ |
| 63 | H | X₂—CH₃ | R | cyclopentyl-X₃ | CH₃-O-X₄ | morpholino-CH₂CH₂CH₂-X₅ |
| 64 | H | X₂—CH₃ | R | cyclopentyl-X₃ | CH₃-O-X₄ | piperidin-1-yl-CH₂CH₂CH₂-X₅ |
| 65 | H | X₂—CH₃ | R | cyclopentyl-X₃ | CH₃-O-X₄ | morpholino-CH₂CH₂-X₅ |
| 66 | H | X₂—CH₃ | R | cyclopentyl-X₃ | CH₃-O-X₄ | piperidin-1-yl-CH₂CH₂-X₅ |
| 67 | H | X₂—CH₃ | R | cyclopentyl-X₃ | CH₃-O-X₄ | (H₃C)₂N-CH₂CH₂-X₅ |

TABLE 2-continued

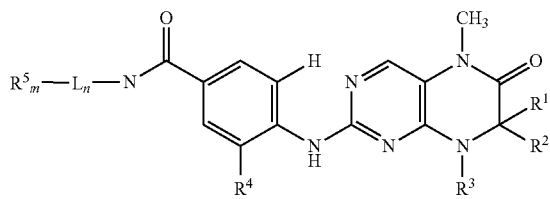

| Example | $R^1$ | $R^2$ | Config. $R^1$ or $R^2$ | $R^3$ | $R^4$ | $L_n$—$R^5_m$ |
|---|---|---|---|---|---|---|
| 68 | H | $X_2$⫽$CH_3$ | R | $X_3$–cyclopentyl | H | $H_3C$–N-bicyclic–$X_5$ |
| 69 | H | $X_2$⫽$CH_3$ | R | $X_3$–cyclopentyl | H | morpholine-propyl-$X_5$ |
| 70 | H | $X_2$⫽$CH_3$ | R | $X_3$–cyclopentyl | H | piperidine-ethyl-$X_5$ |
| 71 | H | $X_2$–$CH_3$ | R | $X_3$–CH($CH_3$)$_2$ | $H_3C$–O–$X_4$ | $X_5$-ethyl-morpholine |
| 72 | H | $X_2$–$CH_3$ | R | $X_3$–CH($CH_3$)$_2$ | $H_3C$–O–$X_4$ | $X_5$-ethyl-piperidine |
| 73 | H | $X_2$–$CH_3$ | R | $X_3$–CH($CH_3$)$_2$ | H | $X_5$-ethyl-N(CH$_2$CH$_3$)$_2$ |
| 74 | H | $X_2$–$CH_3$ | R | $X_3$–CH($CH_3$)$_2$ | $H_3C$–O–$X_4$ | $X_5$-ethyl-N(CH$_2$CH$_3$)$_2$ |
| 75 | H | $X_2$⫽$CH_3$ | R | $X_3$–cyclopentyl | $H_3C$–O–$X_4$ | $H_3C$–N(CH$_3$)-propyl-$X_5$ |

TABLE 2-continued

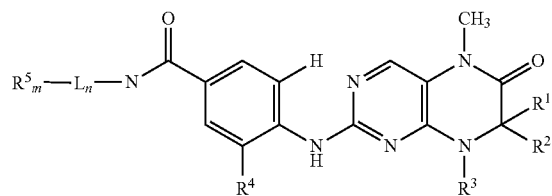

| Example | R¹ | R² | Config. R¹ or R² | R³ | R⁴ | Lₙ—R⁵ₘ |
|---|---|---|---|---|---|---|
| 76 | H | X₂◂CH₃ | R | cyclopentyl-X₃ | CH₃-O-X₄ | (H₃C)(H₃C)CH₂CH₂N-CH₂CH₂CH₂-X₅ (diethylaminopropyl) |
| 77 | H | X₂—CH₂CH₃ | R | (H₃C)₂CH-X₃ | H | X₅-CH₂CH₂-piperidinyl |
| 78 | H | X₂—CH₂CH₃ | R | (H₃C)₂CH-X₃ | H | X₅-CH₂CH₂-morpholinyl |
| 79 | H | X₂◂CH₃ | R | cyclopentyl-X₃ | H | H₃C-N(1-methylpiperidin-4-yl)-X₅ |
| 80 | H | X₂◂CH₃ | R | cyclopentyl-X₃ | CH₃-O-X₄ | H₃C-N(1-methylpiperidin-4-yl)-X₅ |
| 81 | H | X₂-cyclopropyl | R | cyclopentyl-X₃ | CH₃-O-X₄ | X₅-(1-methylpiperidin-4-yl) |
| 82 | H | X₂-cyclopropyl | R | cyclopentyl-X₃ | CH₃-O-X₄ | X₅-(N-methyltropane) |

TABLE 2-continued
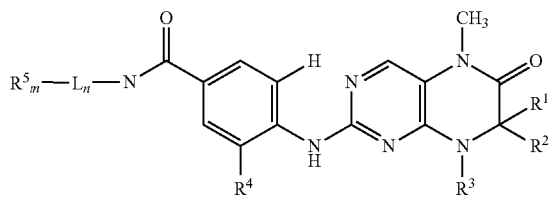
| Example | R¹ | R² | Config. R¹ or R² | R³ | R⁴ | Lₙ—R⁵ₘ |
|---|---|---|---|---|---|---|
| 83 | H | X₂◂CH₃ | R | X₃–cyclopentyl | H₃C–X₄ | H₃C–N-piperidine-4-X₅ |
| 84 | H | X₂◂CH₃ | R | X₃–cyclohexyl | CH₃O–X₄ | X₅–piperidine-N–CH₃ |
| 85 | H | X₂◂CH₃ | R | X₃–cyclohexyl | H | X₅–piperidine-N–CH₃ |
| 86 | H | X₂◂CH₃ | R | X₃–cyclohexyl | CH₃O–X₄ | X₅–C(CH₃)(H₃C)–CH₂–N(CH₃)₂ |
| 87 | H | X₂◂CH₃ | R | X₃–cyclohexyl | CH₃O–X₄ | X₅–C(CH₃)(H₃C)–CH₂–N-pyrrolidine |
| 88 | H | X₂–CH₃ | R | X₃–phenyl | H₃C–O–X₄ | X₅–piperidine-N–CH₃ |

TABLE 2-continued

| Example | R¹ | R² | Config. R¹ or R² | R³ | R⁴ | Lₙ—R⁵ₘ |
|---|---|---|---|---|---|---|
| 89 | H | X₂–CH₂CH₃ | R | X₃–phenyl | H₃C–O–X₄ | X₅–CH₂–C(CH₃)₂–CH₂–N(CH₃)₂ |
| 90 | H | X₂–CH₂CH₃ | R | X₃–CH₂CH₂CH(CH₃)₂ | CH₃–O–X₄ | X₅–C(CH₃)₂–CH₂–N(CH₃)₂ |
| 91 | H | X₂–CH₃ | R | X₃–cyclohexyl | CH₃–O–X₄ | X₅–(N-methyl-8-azabicyclo[3.2.1]) |
| 92 | H | X₂–CH₃ | R | X₃–cyclohexyl | H | X₅–(N-methyl-8-azabicyclo[3.2.1]) |
| 93 | H | X₂–cyclopropyl | R | X₃–cyclopentyl | H | H₃C–N(piperidin-4-yl)–X₅ |
| 94 | H | X₂–CH₃ | R | X₃–cyclohexyl | H₃C–X₄ | X₅–(N-methyl-piperidin-4-yl) |
| 95 | H | X₂–CH₃ | R | X₃–cyclohexyl | H₃C–X₄ | X₅–(N-methyl-8-azabicyclo[3.2.1]) |

TABLE 2-continued

| Example | R¹ | R² | Config. R¹ or R² | R³ | R⁴ | Lₙ—R⁵ₘ |
|---|---|---|---|---|---|---|
| 96 | H | X₂–CH₃ | R | X₃–cyclohexyl | H₃C–O–X₄ | X₅–(1-methylpiperidin-4-yl) |
| 97 | H | X₂–CH₃ | R | X₃–cyclohexyl | H₃C–O–X₄ | X₅–(trans-4-morpholinocyclohexyl) |
| 98 | H | X₂–CH₃ | R | X₃–cyclohexyl | X₄–O–CH₃ | X₅–(trans-4-pyrrolidin-1-ylcyclohexyl) |
| 99 | H | X₂–CH₃ | R | X₃–CH(CH₃)₂ | X₄–O–CH₃ | X₅–(trans-4-(4-(cyclopropylmethyl)piperazin-1-yl)cyclohexyl) |

TABLE 2-continued

| Example | R¹ | R² | Config. R¹ or R² | R³ | R⁴ | Lₙ—R⁵ₘ |
|---|---|---|---|---|---|---|
| 100 | H | X₂—CH₃ | R | X₃-CH(CH₂CH(CH₃)₂) (isobutyl-methylene) | X₄—O—CH₃ | X₅-trans-cyclohexyl-N-piperazinyl-CH₂-cyclopropyl |
| 101 | H | X₂—CH₃ | R | X₃-CH(CH₃)₂ | CH₃—O—X₄ | X₅-(1-benzylpiperidin-4-yl) |
| 102 | H | X₂—CH₂CH₃ | R | X₃-CH(CH₃)₂ | CH₃—O—X₄ | X₅-(1-benzylpiperidin-4-yl) |
| 103 | H | X₂—CH₃ | R | X₃-cyclopentyl | CH₃—O—X₄ | X₅-(1-benzylpiperidin-4-yl) |

TABLE 2-continued

| Example | R¹ | R² | Config. R¹ or R² | R³ | R⁴ | Lₙ—R⁵ₘ |
|---|---|---|---|---|---|---|
| 104 | H | X₂—CH₃ | R | X₃—phenyl | CH₃—O—X₄ | X₅—(1-benzylpiperidin-4-yl) |
| 105 | H | X₂—CH₃ | R | X₃—cyclopentyl | X₄—O—CH₃ | X₅—(trans-4-(4-(cyclopropylmethyl)piperazin-1-yl)cyclohexyl) |
| 106 | H | X₂—CH₃ | R | X₃—cyclopentyl | X₄—O—CH₃ | X₅—(trans-4-(4-methylpiperazin-1-yl)cyclohexyl) |
| 107 | H | X₂—CH₃ | R | X₃—cyclopentyl | X₄—O—CH₃ | X₅—(trans-4-(4-(cyclopropylmethyl)piperazin-1-yl)cyclohexyl) |

TABLE 2-continued

| Example | R¹ | R² | Config. R¹ or R² | R³ | R⁴ | Lₙ—R⁵ₘ |
|---|---|---|---|---|---|---|
| 108 | H | X₂—CH₂—CH₃ | R | X₃—CH(CH₃)₂ | CH₃—O—X₄ | X₅-piperidine-N-tetrahydropyran |
| 109 | H | X₂—CH₃ | R | X₃-cyclopentyl | CH₃—O—X₄ | X₅-piperidine-N-tetrahydropyran |
| 110 | H | X₂—CH₂—CH₃ | R | X₃—CH(CH₃)₂ | X₄—O—CH₃ | X₅-cyclohexyl-piperazine-N-CH₂-cyclopropyl |
| 111 | H | X₂—CH₃ | R | X₃—CH₂—CH(CH₃)₂ | CH₃—O—X₄ | X₅-piperidine-N-tetrahydropyran |

TABLE 2-continued

| Example | R¹ | R² | Config. R¹ or R² | R³ | R⁴ | Lₙ—R⁵ₘ |
|---|---|---|---|---|---|---|
| 112 | H | X₂◂CH₃ | R | X₃ CH(CH₃)₂ | X₄—O—CH₃ | X₅-cyclohexyl-piperazine-CH₂-cyclopropyl |
| 113 | H | X₂—CH₃ | R | X₃ CH(CH₃)₂ | X₄—O—CH₃ | X₅-cyclohexyl-N-methylpiperazine |
| 114 | H | X₂◂CH₃ | R | X₃-CH₂CH₂CH(CH₃)₂ | X₄—O—CH₃ | X₅-cyclohexyl-N(CH₃)₂ |
| 115 | H | X₂◂CH₃ | R | X₃-cyclohexyl | CH₃—O—X₄ | X₅-piperidine-N-CH₂-phenyl |

TABLE 2-continued

| Example | R¹ | R² | Config. R¹ or R² | R³ | R⁴ | Lₙ—R⁵ₘ |
|---|---|---|---|---|---|---|
| 116 | H | X₂—CH₃ (wedge) | R | X₃-cyclopentyl | CH₃—O—X₄ | X₅-piperidine-N-tetrahydropyran |
| 117 | H | X₂—CH₃ | R | X₃-cyclohexyl | CH₃—O—X₄ | X₅-2,2,6,6-tetramethyl-N-methylpiperidine |
| 118 | H | X₂—CH₃ | R | X₃-cyclohexyl | CH₃—O—X₄ | X₅-piperidine-N-isopropyl |
| 119 | H | X₂—CH₃ | R | X₃-cyclohexyl | CH₃—O—X₄ | X₅-piperidine-N-ethyl |
| 120 | H | X₂—CH₃ | R | X₃-cyclohexyl | CH₃—O—X₄ | X₅-piperidine-N-tetrahydropyran |

TABLE 2-continued

| Example | R¹ | R² | Config. R¹ or R² | R³ | R⁴ | Lₙ—R⁵ₘ |
|---|---|---|---|---|---|---|
| 121 | H | X₂—CH₃ | R | X₃-cyclohexyl | CH₃-O-X₄ | X₅-(3-pyrrolidinyl)-N-ethyl |
| 122 | H | X₂—CH₃ | R | X₃-cyclohexyl | CH₃-O-X₄ | X₅-(3-pyrrolidinyl)-N-isopropyl |
| 123 | H | X₂—CH₃ | R | X₃-cyclohexyl | CH₃-O-X₄ | X₅-(3-pyrrolidinyl)-N-ethyl |
| 124 | H | X₂—CH₃ | R | X₃-cyclohexyl | CH₃-O-X₄ | X₅-(3-pyrrolidinyl)-N-isopropyl |
| 125 | H | X₂—CH₃ | R | X₃-cyclohexyl | X₄-O-CH₃ | X₅-(4-cyclohexyl)-N-pyrrolidinyl |

TABLE 2-continued

| Example | R¹ | R² | Config. R¹ or R² | R³ | R⁴ | Lₙ—R⁵ₘ |
|---|---|---|---|---|---|---|
| 126 | H | X₂⋯CH₃ | R | X₃-cyclohexyl | X₄-O-CH₃ | X₅-cyclohexyl-N-piperidinyl |
| 127 | H | X₂⋯CH₃ | R | X₃-cyclohexyl | X₄-O-CH₃ | X₅-cyclohexyl-N-piperidinyl |
| 128 | H | X₂-CH₃ | R | X₃-cyclopentyl | X₄-O-CH₃ | X₅-cyclohexyl-N-piperidinyl |
| 129 | H | X₂-CH₃ | R | X₃-CH(CH₃)₂ | X₄-O-CH₃ | X₅-cyclohexyl-N-piperidinyl |

TABLE 2-continued

| Example | R¹ | R² | Config. R¹ or R² | R³ | R⁴ | Lₙ—R⁵ₘ |
|---|---|---|---|---|---|---|
| 130 | H | X₂—CH₃ (wedge) | R | X₃-cyclohexyl | X₄-O-CH₃ | X₅-cyclohexyl-morpholine |
| 131 | H | X₂-CH₂CH₃ | R | X₃-cyclopentyl | X₄-O-CH₃ | X₅-cyclohexyl-morpholine |
| 132 | H | X₂-CH₂CH₃ | R | X₃-CH(CH₃)₂ | X₄-O-CH₃ | X₅-cyclohexyl-pyrrolidine |
| 133 | H | X₂-CH₂CH₃ | R | X₃-cyclopentyl | X₄-O-CH₃ | X₅-cyclohexyl-morpholine |

TABLE 2-continued

| Example | R¹ | R² | Config. R¹ or R² | R³ | R⁴ | Lₙ—R⁵ₘ |
|---|---|---|---|---|---|---|
| 134 | H | X₂–CH₃ (ethyl) | R | X₃–cyclopentyl | X₄–O–CH₃ | X₅–cyclohexyl–N(piperazine)–phenyl |
| 135 | H | X₂–CH₃ (ethyl) | R | X₃–CH(CH₃)₂ | X₄–O–CH₃ | X₅–cyclohexyl–N(pyrrolidine) |
| 136 | H | X₂–CH₃ (ethyl) | R | X₃–cyclopentyl | X₄–O–CH₃ | X₅–cyclohexyl–N(piperidine) |
| 137 | H | X₂–CH₃ (methyl) | R | X₃–cyclohexyl | X₄–O–CH₃ | X₅–cyclohexyl–N(morpholine) |

TABLE 2-continued

| Example | R¹ | R² | Config. R¹ or R² | R³ | R⁴ | Lₙ—R⁵ₘ |
|---------|----|----|------------------|----|----|---------|
| 138 | H | X₂—CH₃ | R | X₃-cyclopentyl | X₄—O—CH₃ | X₅-cyclohexyl-pyrrolidine (trans) |
| 139 | H | X₂—CH₃ | R | X₃-CH(CH₃)₂ | H₃C—O—X₄ | X₅-N-methyl azabicyclic |
| 140 | H | X₂—CH₃ | R | X₃-CH(CH₃)₂ | H₃C—O—X₄ | X₅-(1-methylpiperidin-4-yl) |
| 141 | H | X₂—CH₃ | R | X₃-CH(CH₃)₂ | H₃C—O—X₄ | X₅-(CH₂)₃-morpholine |
| 142 | H | X₂—CH₃ | R | X₃-CH(CH₃)₂ | H₃C—O—X₄ | X₅-(CH₂)₃-piperidine |
| 143 | H | X₂—CH₃ | R | X₃-CH(CH₃)₂ | H | X₅-(CH₂)₃-morpholine |

TABLE 2-continued

| Example | R¹ | R² | Config. R¹ or R² | R³ | R⁴ | Lₙ—R⁵ₘ |
|---|---|---|---|---|---|---|
| 144 | H | X₂—CH₃ | R | X₃—CH(CH₃)₂ | H | X₅-(1-methylpiperidin-4-yl) |
| 145 | H | H₃C—X₂ | R | H₃C—C(CH₃)₂—CH₂—X₃ | X₄—O—CH₃ | X₅-(1-methylpiperidin-4-yl) |
| 146 | H | X₂—CH₃ | R | X₃—CH₂—CH₂—CH(CH₃)₂ | X₄—O—CH₃ | X₅-(1-methylpiperidin-4-yl) |
| 147 | H | H₃C—X₂ | R | H₃C—C(CH₃)₂—CH₂—X₃ | H | X₅-(2-methyl-2-azabicyclo) |
| 148 | H | X₂—CH₂—CH₃ | R | X₃—CH₂—CH₂—CH(CH₃)₂ | CH₃—O—X₄ | X₅—CH₂CH₂-piperidin-1-yl |
| 149 | H | X₂—CH₂—CH₃ | R | X₃—CH₂—CH₂—CH(CH₃)₂ | CH₃—O—X₄ | X₅—CH₂CH₂—N(CH₂CH₃)₂ |
| 150 | H | X₂—CH₂—CH₃ | R | X₃—CH₂—CH₂—CH(CH₃)₂ | H | X₅—CH₂CH₂-piperidin-1-yl |

TABLE 2-continued

| Example | R¹ | R² | Config. R¹ or R² | R³ | R⁴ | Lₙ—R⁵ₘ |
|---|---|---|---|---|---|---|
| 151 | H | X₂–CH₃ (ethyl) | R | X₃–CH₂CH(CH₃)₂ (isobutyl) | CH₃–O–X₄ | X₅–(CH₂)₃–morpholine |
| 152 | H | X₂–CH₃ (ethyl) | R | X₃–CH₂CH(CH₃)₂ (isobutyl) | CH₃–O–X₄ | X₅–(CH₂)₃–N-methylpiperazine |
| 153 | H | X₂–CH₃ (ethyl) | R | X₃–CH₂CH(CH₃)₂ (isobutyl) | CH₃–O–X₄ | X₅–(CH₂)₄–N(CH₂CH₃)₂ |
| 154 | H | X₂–CH₃ (ethyl) | R | X₃–CH₂CH(CH₃)₂ (isobutyl) | H | X₅–(CH₂)₃–N-methylpiperazine |
| 155 | H | X₂–CH₃ (ethyl) | R | X₃–CH₂CH(CH₃)₂ (isobutyl) | H | X₅–(CH₂)₃–morpholine |

TABLE 2-continued

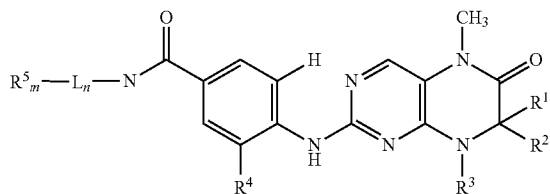

| Example | R¹ | R² | Config. R¹ or R² | R³ | R⁴ | $L_n$—$R^5{}_m$ |
|---|---|---|---|---|---|---|
| 156 | H | X₂—CH₂—CH₃ | R | X₃—CH₂CH₂CH(CH₃)CH₃ | CH₃—O—X₄ | X₅—CH₂CH₂—N(morpholine) |
| 157 | H | X₂—CH₂—CH₃ | R | X₃—CH₂CH₂CH(CH₃)CH₃ | CH₃—O—X₄ | X₅—CH₂CH₂CH₂—N(pyrrolidine) |
| 158 | H | X₂—CH₂—CH₃ | R | X₃—CH₂CH₂CH(CH₃)CH₃ | CH₃—O—X₄ | X₅—CH₂CH₂—N(CH₂CH₃)₂ |
| 159 | H | X₂—CH₂—CH₃ | R | X₃—CH₂CH₂CH(CH₃)CH₃ | CH₃—O—X₄ | X₅—CH₂CH₂—N(CH₃)₂ |
| 160 | H | X₂—CH₂—CH₃ | R | X₃—CH₂CH₂CH(CH₃)CH₃ | CH₃—O—X₄ | X₅—CH₂CH₂—N(CH(CH₃)₂)₂ |
| 161 | X₁—CH₃ | X₂—CH₃ | | X₃—CH₂CH₂CH(CH₃)CH₃ | H₃C—O—X₄ | X₅—CH₂CH₂—N(CH₂CH₃)₂ |

TABLE 2-continued

| Example | R¹ | R² | Config. R¹ or R² | R³ | R⁴ | Lₙ—R⁵ₘ |
|---|---|---|---|---|---|---|
| 162 | X₁—CH₃ | X₂—CH₃ | | X₃—CH(CH₂CH(CH₃)₂) | H₃C—O—X₄ | X₅-(1-methylpiperidin-4-yl) |
| 163 | H | X₂—CH₂CH₃ | R | X₃—CH(CH₂CH(CH₃)₂) | CH₃—O—X₄ | X₅-(quinuclidin-3-yl) |
| 164 | H | X₂—CH₂CH₃ | R | X₃—CH(CH₂CH(CH₃)₂) | CH₃—O—X₄ | X₅—(CH₂)₃—N(CH₃)₂ |
| 165 | H | X₂—CH₂CH₃ | R | X₃—CH(CH₂CH(CH₃)₂) | CH₃—O—X₄ | X₅—(CH₂)₃—N(CH₂CH₃)₂ |
| 166 | H | X₁—CH₂CH₃ | R | X₃-cyclopentyl | CH₃—O—X₄ | X₅-(4-(morpholinomethyl)phenyl) |
| 167 | H | X₂—CH₂CH₃ | R | X₃—CH(CH₂CH(CH₃)₂) | CH₃—O—X₄ | X₅—CH₂CH₂-(1-methylpyrrolidin-2-yl) |

TABLE 2-continued

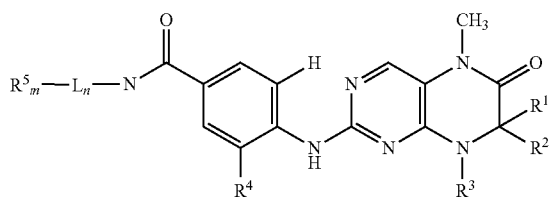

| Example | R¹ | R² | Config. R¹ or R² | R³ | R⁴ | Lₙ—R⁵ₘ |
|---|---|---|---|---|---|---|
| 168 | H | X₂—CH₃ | R | X₃—CH₂CH₂CH(CH₃)CH₃ | CH₃O—X₄ | X₅—CH₂C(CH₃)₂CH₂N(CH₃)CH₂CH₃ (with H₃C) |
| 169 | H | X₂—CH₃ | R | X₃—CH₂CH₂CH(CH₃)CH₃ | CH₃O—X₄ | X₅—(CH₂)₃-piperidinyl |
| 170 | H | X₂—CH₃ | R | X₃—CH₂CH₂CH(CH₃)CH₃ | CH₃O—X₄ | X₅—(CH₂)₂-pyrrolidinyl |
| 171 | H | X₂—CH₃ | R | X₃—CH₂CH₂CH(CH₃)CH₃ | CH₃O—X₄ | X₅—(1-methylpiperidin-4-yl) |
| 172 | H | X₂—CH₃ | R | X₃—CH₂CH₂CH(CH₃)CH₃ | CH₃O—X₄ | X₅—(1-methylazepan-4-yl) |
| 173 | H | X₂—CH₃ | R | X₃—CH₂CH₂CH(CH₃)CH₃ | CH₃O—X₄ | X₅—(N-methyl-tropanyl) |

TABLE 2-continued

| Example | R¹ | R² | Config. R¹ or R² | R³ | R⁴ | Lₙ—R⁵ₘ |
|---|---|---|---|---|---|---|
| 174 | H | X₂–CH₂–CH₃ | R | X₃–CH₂–CH(CH₃)₂ | CH₃–O–X₄ | X₅-(4-piperidinyl)-N-benzyl |
| 175 | H | X₂–CH₃ | R | X₃-cyclopentyl | CH₃–O–X₄ | X₅–C(CH₃)₂–CH₂–N(CH₃)₂ |
| 176 | H | X₂–CH₂CH₃ | R | X₃–CH(CH₃)₂ | CH₃–O–X₄ | X₅–C(CH₃)₂–CH₂–N(CH₃)₂ |
| 177 | H | X₂–CH₂CH₃ | R | X₃-cyclopentyl | CH₃–O–X₄ | X₅–C(CH₃)₂–CH₂–N(CH₃)₂ |
| 178 | H | X₂–CH₂–CH₃ | R | X₃–CH(CH₃)₂ | CH₃–O–X₄ | X₅-(4-piperidinyl) |
| 179 | H | X₂–CH₂–CH₃ | R | X₃–CH₂–CH(CH₃)₂ | CH₃–O–X₄ | X₅-(4-piperidinyl) |

TABLE 2-continued

| Example | R¹ | R² | Config. R¹ or R² | R³ | R⁴ | Lₙ—R⁵ₘ |
|---|---|---|---|---|---|---|
| 180 | H | X₂—CH₃ (ethyl) | R | X₃-cyclohexyl | H₃C—O—X₄ | X₅-(1-benzylpiperidin-4-yl) |
| 181 | H | X₂◂CH₃ | R | X₃-tetrahydropyran-4-yl | CH₃—O—X₄ | X₅-(1-benzylpiperidin-4-yl) |
| 182 | H | X₂◂CH₃ | R | X₃-cyclopentyl | CH₃—O—X₄ | H₃C-C(CH₃)(X₅)-CH₂-morpholino |
| 183 | H | X₂—CH₃ | R | X₃-CH(CH₃)₂ (isopropyl) | CH₃—O—X₄ | H₃C-C(CH₃)(X₅)-CH₂-morpholino |
| 184 | H | X₂—CH₃ | R | X₃-cyclopentyl | CH₃—O—X₄ | H₃C-C(CH₃)(X₅)-CH₂-morpholino |

TABLE 2-continued

| Example | R¹ | R² | Config. R¹ or R² | R³ | R⁴ | Lₙ—R⁵ₘ |
|---|---|---|---|---|---|---|
| 185 | H | X₂–CH₃ | R | 4-methoxyphenyl (X₃) | CH₃O–X₄ | H₃C-C(CH₃)₂-CH₂-morpholin-4-yl (X₅) |
| 186 | H | X₂–CH₃ | R | cyclohexyl (X₃) | CH₃O–X₄ | 4-(4-methylpiperazin-1-yl)phenyl (X₅) |
| 187 | H | X₂–CH₃ (ethyl) | R | cyclopentyl (X₃) | CH₃O–X₄ | 4-(4-methylpiperazin-1-yl)phenyl (X₅) |
| 188 | H | X₂–CH₃ | R | cyclopentyl (X₃) | Cl–X₄ | 1-methylpiperidin-4-yl (X₅) |

TABLE 2-continued

| Example | R¹ | R² | Config. R¹ or R² | R³ | R⁴ | Lₙ—R⁵ₘ |
|---|---|---|---|---|---|---|
| 189 | H | X₂—CH₃ (ethyl) | R | X₃-cyclohexyl | X₄—O—CH₃ | X₅-cyclohexyl-morpholine (trans) |
| 190 | H | X₂—CH₃ | R | X₃-cyclopentyl | CH₃—O—X₄ | X₅-piperidine |
| 191 | H | X₂-cyclopropyl | R | X₃-CH(CH₃)₂ | H₃C-CH₂-O—X₄ | X₅-N-methylpiperidine |
| 192 | H | X₂—CH₃ | R | X₃-cyclohexyl | CH₃—O—X₄ | X₅-C(CH₃)₂-CH₂-morpholine |
| 193 | H | X₂—CH₃ (ethyl) | R | X₃-cyclohexyl | CH₃—O—X₄ | X₅-C(CH₃)₂-CH₂-morpholine |
| 194 | H | X₂—CH₃ (ethyl) | R | X₃-phenyl | CH₃—O—X₄ | X₅-C(CH₃)₂-CH₂-morpholine |

TABLE 2-continued

| Example | R¹ | R² | Config. R¹ or R² | R³ | R⁴ | Lₙ—R⁵ₘ |
|---|---|---|---|---|---|---|
| 195 | H | X₂–CH₃ | R | X₃–CH₂CH(CH₃)CH₃ | CH₃O–X₄ | H₃C–C(CH₃)(X₅)–CH₂–N(morpholine) |
| 196 | H | X₂–CH₂CH₃ | R | X₃–CH₂CH₂CH(CH₃)CH₃ | CH₃O–X₄ | H₃C–C(CH₃)(X₅)–CH₂–N(4-methylpiperazine) |
| 197 | H | X₂–cyclopropyl | | X₃–CH₂CH₂CH(CH₃)CH₃ | CH₃O–X₄ | H₃C–C(CH₃)(X₅)–CH₂–N(4-methylpiperazine) |
| 198 | H | X₂,X₃-cyclopentyl (spiro) | R | | H₃C–O–X₄ | X₅–(1-methylpiperidin-4-yl) |
| 199 | H | X₂,X₃-cyclopentyl (spiro) | R | | H₃C–O–X₄ | X₅–(trans-4-morpholinocyclohexyl) |

TABLE 2-continued

| Example | R¹ | R² | Config. R¹ or R² | R³ | R⁴ | Lₙ—R⁵ₘ |
|---|---|---|---|---|---|---|
| 200 | H | X₂–[cyclopentyl-X₃] | R | | CH₃–O–X₄ | X₅–[4-(1-methylpiperidinyl)] |
| 201 | H | X₂–[cyclopentyl-X₃] | R | | CH₃–O–X₄ | X₅–[4-(1-benzylpiperidinyl)] |
| 202 | X₁–CH₃ | X₂–CH₃ | | X₃–CH₂CH(CH₃)₂ (isobutyl) | CH₃–O–X₄ | X₅–[4-(morpholinomethyl)phenyl] |
| 203 | H | X₂–CH₃ | R | X₃–cyclopentyl | Cl–X₄ | X₅–[4-(1-benzylpiperidinyl)] |
| 204 | H | X₂–CH₃ | R | X₃–CH₂CH(CH₃)₂ | CH₃–O–X₄ | X₅–[4-(1-benzylpiperidinyl)] |

TABLE 2-continued
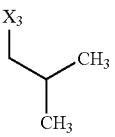
| Example | R¹ | R² | Config. R¹ or R² | R³ | R⁴ | L$_n$—R⁵$_m$ |
|---------|----|----|------------------|----|----|----|
| 205 | H | X₂◂CH₃ | R | X₃-CH₂CH(CH₃)₂ | X₄-O-CH₃ |  |
| 206 | H | X₂◂CH₃ | R | X₃-CH₂C(CH₃)₃ | X₄-O-CH₃ | 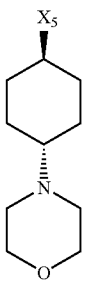 |
| 207 | H | X₂◂CH₃ | R | X₃-CH₂C(CH₃)₃ | X₄-O-CH₃ | 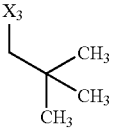 |
| 208 | H | X₂◂CH₃ | R | X₃-CH₂C(CH₃)₃ | X₄-O-CH₃ |  |

TABLE 2-continued

| Example | R¹ | R² | Config. R¹ or R² | R³ | R⁴ | Lₙ—R⁵ₘ |
|---|---|---|---|---|---|---|
| 209 | H | X₂—CH₃ | R | X₃ isobutyl | X₄—O—CH₃ | X₅-cyclohexyl-piperazinyl-N-CH₃ |
| 210 | H | X₂—CH₃ | R | X₃-cyclopentyl | X₄—O—CH₃ | X₅-cyclohexyl-piperazinyl-N-CH₃ |
| 211 | X₁—CH₃ | X₂—CH₃ | | X₃-isopentyl | X₄—O—CH₃ | X₅-cyclohexyl-morpholinyl |
| 212 | X₁—CH₃ | X₂—CH₃ | | X₃-isopentyl | X₄—O—CH₃ | X₅-cyclohexyl-piperazinyl-N-CH₂-cyclopropyl |

TABLE 2-continued

| Example | R¹ | R² | Config. R¹ or R² | R³ | R⁴ | Lₙ—R⁵ₘ |
|---------|----|----|------------------|----|----|--------|
| 213 | H | X₂—CH₃ | R | cyclohexyl (X₃) | X₄—O—CH₃ | X₅-cyclohexyl-piperazine-C(O)CH₃ |
| 214 | H | X₂—CH₂CH₃ | R | X₃—CH(CH₃)₂ | X₄—O—CH₃ | X₅-cyclohexyl-N-methylpiperazine |
| 215 | X₁—CH₃ | X₂—CH₃ | | X₃—CH₂CH(CH₃)₂ | X₄—O—CH₃ | X₅-cyclohexyl-N-methylpiperazine |
| 216 | H | X₂—CH₃ | R | cyclohexyl (X₃) | X₄—O—CH₃ | X₅-cyclohexyl-N-methylpiperazine |

TABLE 2-continued

| Example | R¹ | R² | Config. R¹ or R² | R³ | R⁴ | Lₙ—R⁵ₘ |
|---|---|---|---|---|---|---|
| 217 | H | X₂—CH₂CH₃ | R | X₃-cyclopentyl | X₄—O—CH₃ | X₅-cyclohexyl-N(4-methylpiperazine) |
| 218 | H | X₂—CH₃ | R | X₃—CH₂CH(CH₃)₂ | X₄—O—CH₃ | X₅-cyclohexyl-thiomorpholine |
| 219 | H | X₂—CH₂CH₃ | R | X₃—CH₂CH(CH₃)₂ | X₄—O—CH₃ | X₅-cyclohexyl-morpholine |
| 220 | H | X₂—CH₃ | R | X₃—CH₂C(CH₃)₃ | X₄—O—CH₃ | X₅-cyclohexyl-morpholine |

TABLE 2-continued

| Example | R¹ | R² | Config. R¹ or R² | R³ | R⁴ | Lₙ—R⁵ₘ |
|---|---|---|---|---|---|---|
| 221 | H | X₂—CH₃ | R | X₃–CH₂CH₂–CH(CH₃)₂ | X₄–O–CH₃ | X₅–cyclohexyl–N(piperazine)–N–CH₃ |
| 222 | H | X₂–CH₂CH₃ | R | X₃–CH₂CH₂–CH(CH₃)₂ | X₄–O–CH₃ | X₅–cyclohexyl–N(piperazine)–N–CH₃ |
| 223 | H | X₂—CH₃ | R | X₃–phenyl | X₄–O–CH₂CH₃ | X₅–piperidine–N–CH₃ |
| 224 | H | X₂—CH₃ | R | X₃–(3-methoxyphenyl) | X₄–O–CH₃ | X₅–piperidine–N–CH₃ |
| 225 | H | X₂—CH₃ | R | X₃–(3-methoxyphenyl) | H | X₅–piperidine–N–CH₃ |

TABLE 2-continued
| Example | R¹ | R² | Config. R¹ or R² | R³ | R⁴ | Lₙ—R⁵ₘ |
|---|---|---|---|---|---|---|
| 226 | H | X₂⬛CH₃ | R |  | H₃C—O—X₄ | 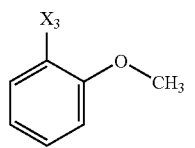 |
| 227 | H | X₂⬛CH₃ | R |  | CH₃—O—X₄ | 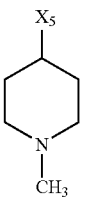 |
| 228 | H | X₂⬛CH₃ | R |  | X₄—O—CH₃ | 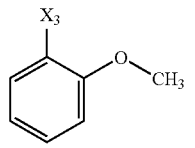 |
| 229 | H | X₂—CH₃ | R |  | CH₃—O—X₄ | 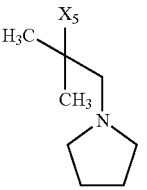 |
| 230 | H | X₂⬛CH₃ | R |  | CH₃—O—X₄ | 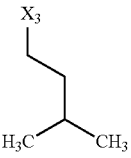 |

TABLE 2-continued

| Example | R¹ | R² | Config. R¹ or R² | R³ | R⁴ | Lₙ—R⁵ₘ |
|---|---|---|---|---|---|---|
| 231 | H | X₂—CH₃ | R | X₃-cyclopentyl | CH₃O—X₄ | X₅—CH₂—C(CH₃)₂—CH₂—N(piperidine) |
| 232 | H | X₂▬CH₃ | R | X₃-cyclohexyl | X₄—O—CH₃ | X₅-cyclohexyl-N(piperazine) |
| 233 | H | X₁▬CH₃ | R | X₃—CH₂—C(CH₃)₃ | X₄—O—CH₃ | X₅-cyclohexyl-N(2,6-dimethylmorpholine) |
| 234 | H | X₁—CH₃ | R | X₃—CH(CH₃)₂ | X₄—O—CH₃ | X₅-cyclohexyl-N(2,6-dimethylmorpholine) |

TABLE 2-continued

| Example | R¹ | R² | Config. R¹ or R² | R³ | R⁴ | Lₙ—R⁵ₘ |
|---|---|---|---|---|---|---|
| 235 | H | X₁▬CH₃ | R | X₃ (isobutyl) | X₄—O—CH₃ | X₅-cyclohexyl-N-thiomorpholine S-oxide |
| 236 | H | X₁▬CH₃ | R | X₃ (isobutyl) | X₄—O—CH₃ | X₅-cyclohexyl-N-thiomorpholine S-oxide |
| 237 | H | X₁—CH₂CH₃ | R | X₃ (isopropyl) | CH₃—O—X₄ | X₅-piperidine |
| 238 | H | X₁▬CH₃ | R | X₃-cyclopentyl | CH₃—O—X₄ | X₅-piperidine |

TABLE 2-continued

| Example | R¹ | R² | Config. R¹ or R² | R³ | R⁴ | $L_n$—$R^5_m$ |
|---|---|---|---|---|---|---|
| 239 | H | $X_1$—CH₃ | R | cyclopentyl-$X_3$ | CH₃—O—$X_4$ | neopentyl-morpholine with $X_5$ |
| 240 | H | $X_1$—CH₃ | R | cyclohexyl-$X_3$ | CH₃—O—$X_4$ | neopentyl-N(CH₃)₂ with $X_5$ |
| 241 | H | $X_1$—CH₃ | R | isopentyl-$X_3$ | CH₃—O—$X_4$ | neopentyl-(N-methylpiperazine) with $X_5$ |
| 242 | H | $X_1$—CH₃ | R | isopentyl-$X_3$ | CH₃—O—$X_4$ | ethyl-piperidine with $X_5$ |
| 243 | H | $X_1$—CH₃ | R | isopentyl-$X_3$ | CH₃—O—$X_4$ | propyl-N(CH₃)₂ with $X_5$ |
| 244 | H | $X_1$—CH₃ | R | isopentyl-$X_3$ | CH₃—O—$X_4$ | propyl-(N-methylpiperazine) with $X_5$ |

What is claimed is:

1. A method of treating cancer selected from the group consisting of carcinomas, sarcomas, melanomas, myeloma, hematologic neoplasias, lymphomas and childhood cancers said method comprises administering to a patient a therapeutically effective amount of a compound selected from the group consisting of the compounds of Formula shown in the following Table

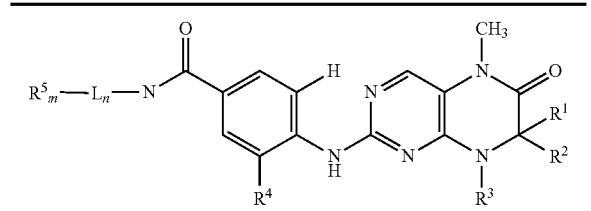

| Example | R¹ | R² | Config. R¹ or R² |
|---|---|---|---|
| 27 | H | X₂—CH₃ | R |
| 44 | H | X₂—CH₃ | R |
| 55 | H | X₂—CH₃ | R |
| 58 | H | X₂—CH₃ | R |
| 102 | H | X₂—CH₃ | R |
| 103 | H | X₂—CH₃ | R |
| 105 | H | X₂—CH₃ | R |
| 110 | H | X₂—CH₃ | R |
| 115 | H | X₂—CH₃ | R |
| 133 | H | X₂—CH₃ | R |
| 134 | H | X₂—CH₃ | R |
| 234 | H | X₁—CH₃ | R |
| 240 | H | X₁—CH₃ | R | and

| 46 | H | X₂—CH₃ | R |

-continued

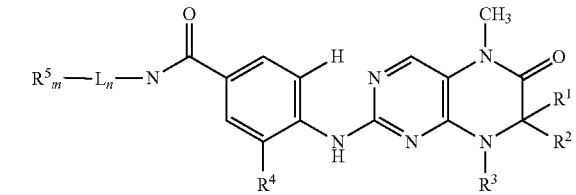

| Example | R³ | R⁴ | Lₙ—R⁵ₘ |
|---|---|---|---|
| 27 | 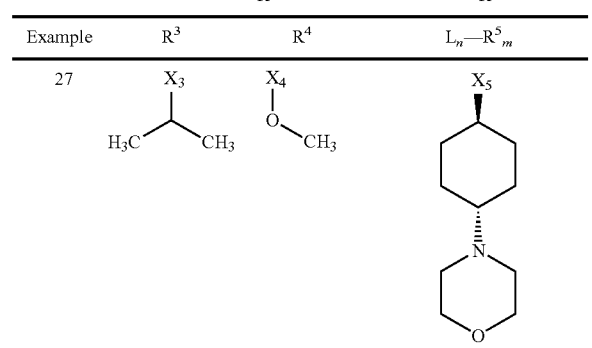 | | |
| 44 | | | |
| 55 | 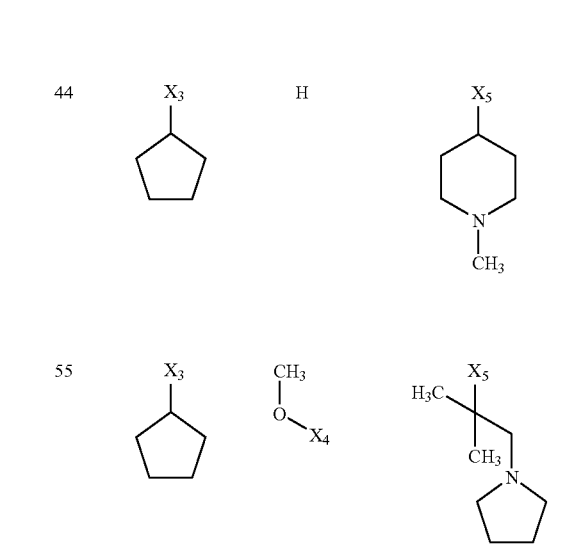 | | |
| 58 | | | |
| 102 | 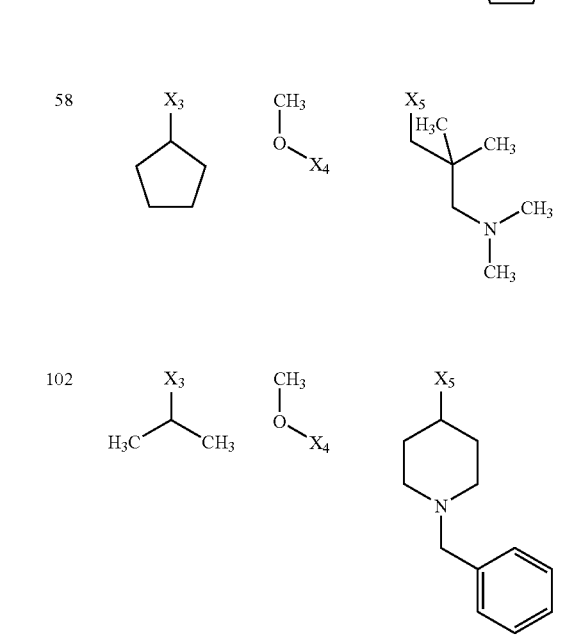 | | |

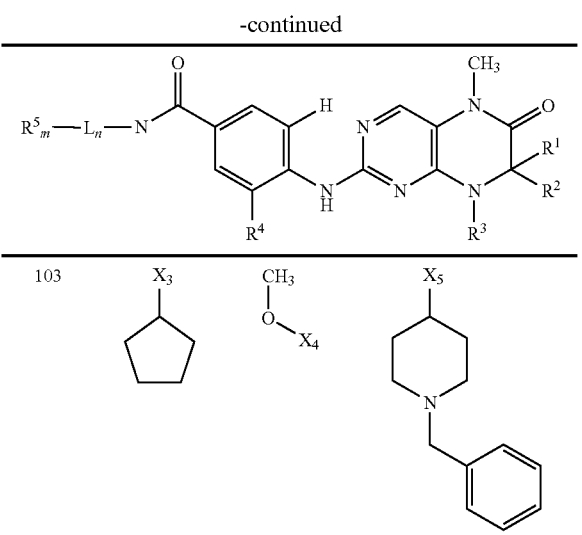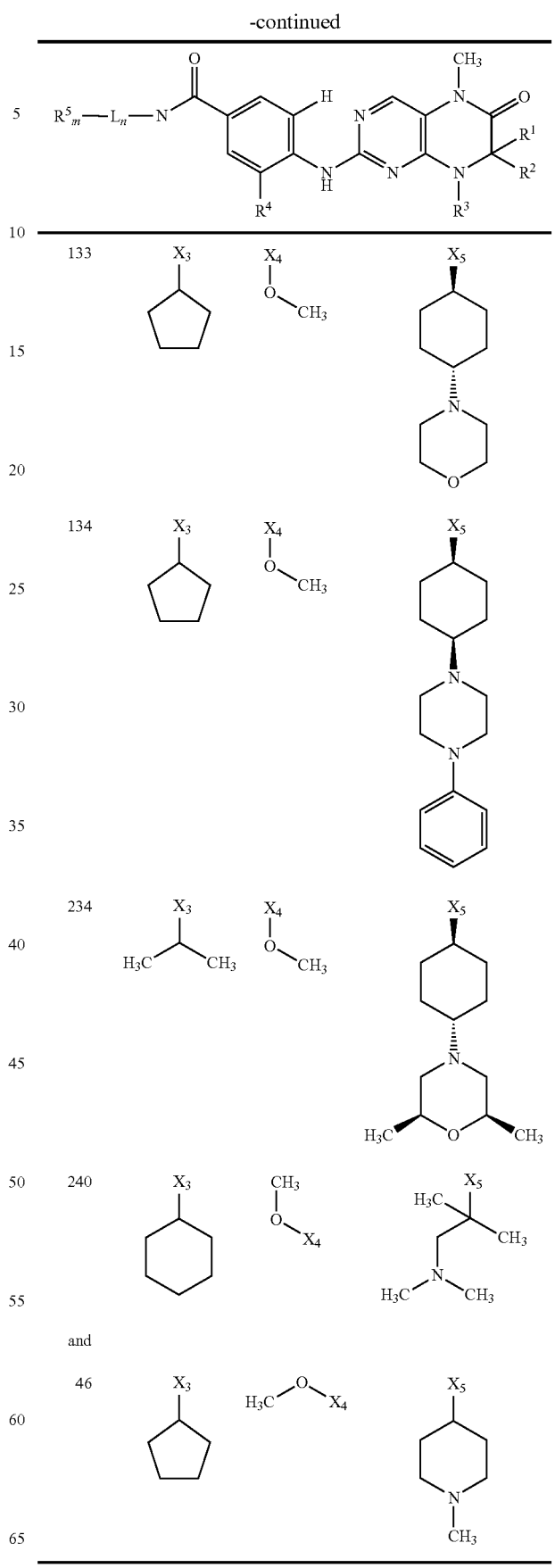

wherein the abbreviations $X_1$, $X_2$, $X_3$, $X_4$ and $X_5$ used in the Table in each case denote a link to a position in the general Formula shown in the Table instead of the corresponding groups $R^1$, $R^2$, $R^3$, $R^4$ and L-$R^5$, optionally in form of the pharmacologically acceptable acid addition salts thereof.

2. The method according to claim 1, wherein the cancer hematologic neoplasm is leukemia.

3. The method according to claim 1 wherein the compound is

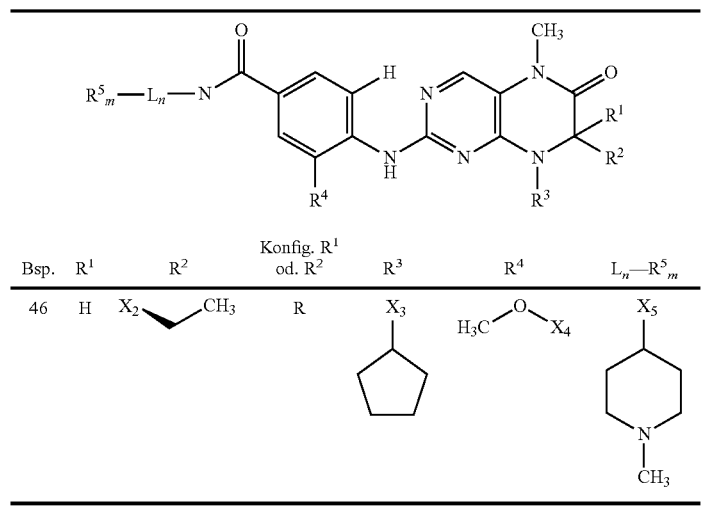

wherein the abbreviations $X_1$, $X_2$, $X_3$, $X_4$ and $X_5$ used in the Table denote a link to a position in the general Formula shown in the Table instead of the corresponding groups $R^1$, $R^2$, $R^3$, $R^4$ and L-$R^5$, optionally in form of the pharmacologically acceptable acid addition salts thereof.

4. The method according to claim 1 wherein the compound is

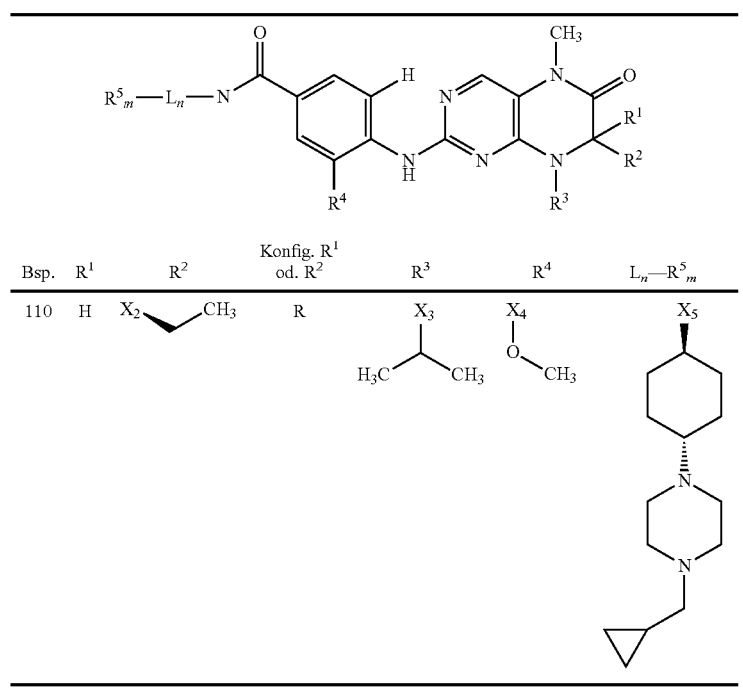

wherein the abbreviations $X_1$, $X_2$, $X_3$, $X_4$ and $X_5$ used in the Table denote a link to a position in the general Formula shown in the Table instead of the corresponding groups $R^1$, $R^2$, $R^3$, $R^4$ and L-$R^5$, optionally in form of the pharmacologically acceptable acid addition salts thereof.

5. The method of claim 1, wherein the carcinomas, sarcomas, melanomas, myeloma, hematologic neoplasias, lymphomas and childhood cancers are selected from the group consisting of central nervous system tumours, bronchial and mediastinal tumours, tumours of the gastrointestinal tract, gynaecological cancers, urinary tract and testicular cancers, tumours of endocrine tissue, Ewing-sarcoma, osteosarcoma, osteogenic sarcoma, chondrosarcoma, synovial sarcoma, leiomyosarcoma, rhabdomyosarcoma, mesothelial sarcoma, mesothelioma, fibrosarcoma, angiosarcoma, hemangioendothelioma, liposarcoma, glioma, astrocytoma, myxosarcoma, malignant fibrous histiocytoma, mesenchymous, mixed mesodermal tumour, neuroblastoma, melanoma, nodular and lentigo-maligna melanoma, immunocytoma myeloma, plasmocytoma myeloma, multiple myeloma, leukemia, acute or chronic leukemia of myeloid, Hodgkin-lymphoma or T- and B-cell non-Hodgkin-lymphomas.

* * * * *